US011209432B2

(12) United States Patent
Cartwright et al.

(10) Patent No.: US 11,209,432 B2
(45) Date of Patent: Dec. 28, 2021

(54) ASSAYS FOR ANTIMICROBIAL ACTIVITY AND APPLICATIONS THEREOF

(71) Applicant: PRESIDENT AND FELLOWS OF HARVARD COLLEGE, Cambridge, MA (US)

(72) Inventors: Mark J. Cartwright, West Newton, MA (US); Nazita Gamini, Somerville, MA (US); Donald E. Ingber, Boston, MA (US); Martin Rottman, La Celle-Saint-Cloud (FR); Michael Super, Lexington, MA (US); Julie A. Tomolonis, Houston, TX (US); Karen A. Sinclair, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 16/898,754

(22) Filed: Jun. 11, 2020

(65) Prior Publication Data

US 2020/0300854 A1 Sep. 24, 2020

Related U.S. Application Data

(63) Continuation of application No. 15/668,794, filed on Aug. 4, 2017, now Pat. No. 10,718,766, which is a continuation of application No. 14/904,583, filed as application No. PCT/US2014/046716 on Jul. 15, 2014, now Pat. No. 9,791,440.

(60) Provisional application No. 61/866,843, filed on Aug. 16, 2013, provisional application No. 61/846,438, filed on Jul. 15, 2013.

(51) Int. Cl.
*A61K 39/00* (2006.01)
*A61K 39/02* (2006.01)
*G01N 33/569* (2006.01)
*C12Q 1/18* (2006.01)

(52) U.S. Cl.
CPC ......... *G01N 33/56911* (2013.01); *C12Q 1/18* (2013.01); *G01N 33/5695* (2013.01); *G01N 33/56961* (2013.01); *G01N 2333/4724* (2013.01); *G01N 2400/00* (2013.01); *G01N 2800/26* (2013.01); *G01N 2800/52* (2013.01)

(58) Field of Classification Search
CPC ..... A61K 39/00; A61K 39/02; G01N 33/5005
USPC .................. 424/234.1; 435/4, 7.2
See application file for complete search history.

(56) References Cited

U.S. PATENT DOCUMENTS

| | | |
|---|---|---|
| 2004/0258664 A1 | 12/2004 | Pitcovski et al. |
| 2005/0272101 A1 | 12/2005 | Devarajan et al. |
| 2010/0292268 A1 | 11/2010 | Mosher et al. |
| 2010/0311052 A1 | 12/2010 | Bendtzen et al. |
| 2011/0306032 A1 | 12/2011 | Galiano et al. |
| 2012/0129197 A1 | 5/2012 | Banaei |
| 2013/0035283 A1 | 2/2013 | Super et al. |
| 2013/0334120 A1 | 12/2013 | Ingber et al. |

FOREIGN PATENT DOCUMENTS

| | | |
|---|---|---|
| EP | 2490021 A1 | 8/2012 |
| WO | 2007/092427 A2 | 8/2007 |
| WO | 2009/003905 A2 | 1/2009 |
| WO | 2011/090954 A2 | 7/2011 |
| WO | 2011/091037 A2 | 7/2011 |
| WO | 2011/116872 A1 | 9/2011 |
| WO | 2011/153226 A2 | 12/2011 |
| WO | 2012/103337 A2 | 8/2012 |
| WO | 2012/106396 A2 | 8/2012 |
| WO | 2012/135834 A2 | 10/2012 |
| WO | 2013/012924 A2 | 1/2013 |
| WO | 2013/130875 A1 | 9/2013 |
| WO | 2014/014788 A2 | 1/2014 |
| WO | 2014/144325 A1 | 9/2014 |

OTHER PUBLICATIONS

Boller et al., "A renaissance of elicitors: perception of microbe-associated molecular patterns and danger signals by pattern-recognition receptors", Annu Rev Plant Biol, 60:379-406 (2009).
Garnacho-Montero et al., "Timing of adequate antibiotic therapy is a greater determinant of outcome than are TNF and IL-10 polymorphisms in patients with sepsis", Critical Care 10(4):R111 (2006).
He et al., "Elicitation and suppression of microbe-associated molecular pattern-triggered immunity in plant-microbe interactions", Cell Microbiol, 9(6):1385-96 (2007).
Murray et al., "Current Approaches to the Diagnosis of Bacterial and Fungal Bloodstream Infections in the Intensive Care Unit", Crit Care Med. 40(12):3277-3282 (2012).
Neth et al., "Mannose-binding lectin binds to a range of clinically relevant microorganisms and promotes complement deposition." Infection and immunity 68.2 (2000): 688-693.
Schelenz et al., "Binding of host collectins to the pathogenic yeast Cryptococcus neoformans: human surfactant protein D acts as an agglutinin for acapsular yeast cells." Infection and Immunity 63.9 (1995): 3360-3366.
Van Emmerik et al., "Binding of mannan-binding protein to various bacterial pathogens of meningitis." Clinical & Experimental Immunology 97.3 (1994): 411-416.

*Primary Examiner* — Rodney P Swartz
(74) *Attorney, Agent, or Firm* — Nixon Peabody LLP; David S. Resnick; Nicole D. Kling

(57) ABSTRACT

The disclosure provides methods, compositions, and kits for enhanced detection of microbes in samples and monitoring of antimicrobial activity in a subject.

19 Claims, 25 Drawing Sheets

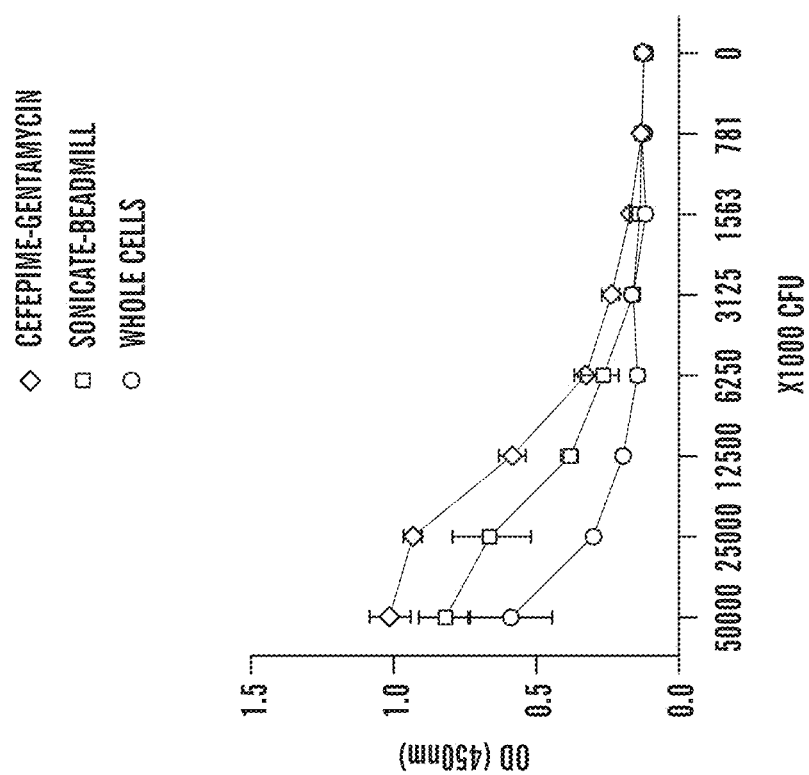
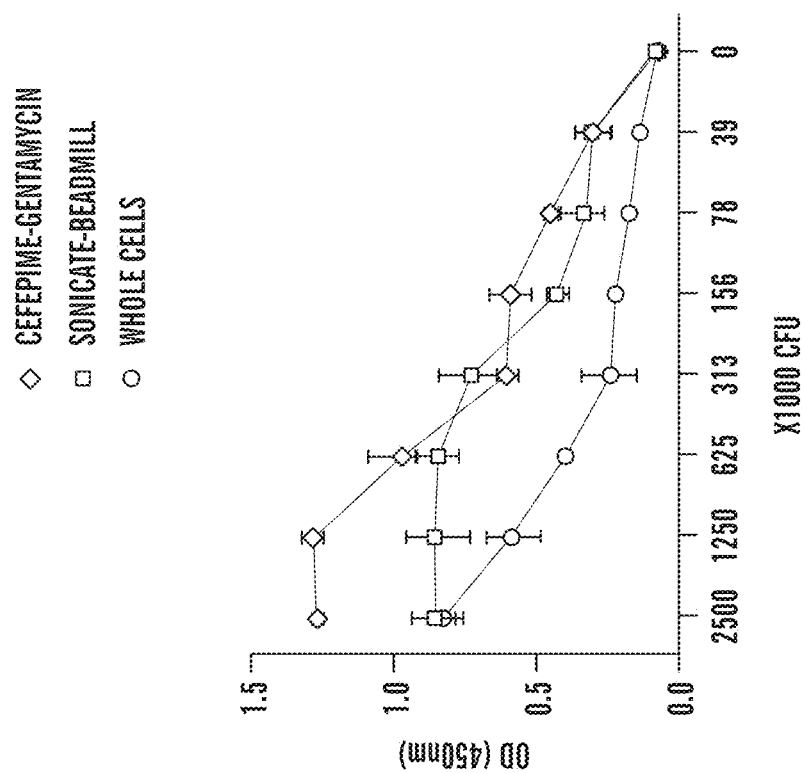
FIG. 4A
FIG. 4B

EndoSafe MEASUREMENTS

ADD 16 μg OF LPS

| LPS BUFFER | 12.4 EU/ml |
|---|---|
| LPS FBS | 11.1 EU/ml |
| LPS BLOOD | 4.71 EU/ml |

WITHOUT LPS

| BEAD BUFFER | <0.5 EU/ml |
|---|---|
| BEAD FBS | <0.5 EU/ml |
| BEAD BLOOD | <0.5 EU/ml |

ASSAYS FOR ANTIMICROBIAL ACTIVITY AND APPLICATIONS THEREOF

CROSS-REFERENCE TO RELATED APPLICATIONS

This application is a Continuation application that claims benefit under 35 USC § 120 of U.S. application Ser. No. 15/668,794 filed Aug. 4, 2017, which was issued as U.S. Pat. No. 10,718,766 on Jul. 21, 2020, which is a Continuation application that claims benefit under 35 USC § 120 of patented U.S. application Ser. No. 14/904,583 filed Jan. 12, 2016, which was issued as U.S. Pat. No. 9,791,440 on Oct. 17, 2017, which is a 35 U.S.C. § 371 National Phase Entry Application of International Application No. PCT/US14/46716 filed Jul. 15, 2014, which designates the U.S., and which claims benefit under 35 U.S.C. § 119(e) of the U.S. Provisional Application No. 61/846,438 filed Jul. 15, 2013, and the U.S. Provisional Application No. 61/866,843 filed Aug. 16, 2013, the contents of each of which are incorporated herein by reference in their entireties.

GOVERNMENT SUPPORT

This invention was made with government support under N66001-11-1-4180 awarded by U.S. Department of Defense, Space and Naval Warfare Systems Center and under HR0011-13-C-0025 awarded by the U.S. Department of Defense, Defense Advanced Research Projects Agency (DARPA). The government has certain rights in the invention.

TECHNICAL FIELD

Described herein relates generally to methods, compositions, and kits for enhanced detection of microbes in samples and monitoring of antimicrobial activity in a sample or subject.

BACKGROUND

Patients commonly suffer infections that go unrecognized and lead to sepsis because of the associated trauma, burns and invasive life support. Every hour between diagnosis and administration of the correct treatment decreases survival significantly. For example, in one study, the risk for in-hospital mortality increased by 9% for every hour of delay before the correct antibiotic regimen was administered. Garnacho-Montero, J. et al., Critical care 10, R111 (2006). Thus, the speed of pathogen diagnosis in a soldier with a blood-borne microbial infection can mean the difference between life and death. However, infections are challenging to diagnose in the field or in a hospital.

Sepsis is a clinical syndrome defined as the systemic response to infection. Although it is one of the leading causes of death in developed countries and is responsible for one in three to one in two deaths in hospitalized patients in the USA, no therapeutic nor diagnostic breakthrough has occurred since the discovery of antibiotics and the improvement in supportive measures. The diagnosis of sepsis is still highly empirical and is defined as a systemic inflammatory response syndrome (SIRS) caused by an infection.

In general, existing diagnostics of infection rely on two concepts: direct diagnosis and indirect diagnosis. Direct diagnosis is based on evidencing the presence of a pathogen in a clinical sample. For example, direct examination, which is specific but has a low sensitivity, can allow direct observation of the pathogen through specific coloration using differential dyes. Blood culture is the gold standard to prove infection. However, it is time consuming (e.g., about 1-7 days), and only 5% to 15% of the all cultures drawn for any reason are positive, and half of patients with septic shock have negative blood cultures and no microbiological documentation of the infection. Murray and Masur, Critical care medicine 40, 3277 (2012). Tuberculosis cultures can particularly be time consuming, ranging from 1-60 days.

Nucleic acid-based detection generally relies on polymerase chain reaction (PCR). However, it can be susceptible to false negatives from failure to extract bacterial DNA, competition from host DNA and inhibition by matrix components and/or to false positives due to its high sensitivity to contaminating DNA, and has failed to improve the management of sepsis patients. Microbial antigen based detection is generally based on the detection of microbe specific antigens by monoclonal antibodies. The existing microbial antigen-based assays can detect *Legionella pneumophila* serotype 1 in urine, *Streptococcus pneumoniae* in urine and fungal carbohydrates in blood.

Indirect diagnosis is generally based on the detection of the host response to infection. For example, serological assays are typically based on the detection of host antibodies directed against microbial determinants and allow specific identification of the agent when unique microbial epitopes can be used for the capture of unique host antibodies. Thus, diagnosis is often retrospective and can be used for the diagnosis of chronic infections (e.g., Lyme disease and syphilis, viral infections). Proteomic biomarkers are host proteins that can show marked variations in infected patients. Proteomic biomarkers can be sensitive but existing target markers (e.g., C-Reactive Protein, Procalcitonin, IL-1, IL-6, THF) are not specific for infection and general stresses such as recent surgery, trauma, neoplastic diseases or autoimmune disorders can also affect the same markers used to detect infection. Thus, there is currently no test allowing the diagnosis of infection in the SIRS patient population.

Sepsis diagnosis is therefore dependent on the combination of a clinical suspicion of infection and general clinical and biological criteria such as heart and respiratory rates, temperature, hyperglycemia or white blood cells counts. Patient stratification schemes distinguish severe sepsis based on acute organ failure documented by simple clinical and biological variables (lactates, platelets, bilirubin, creatinine, capillary refill or urine output) and septic shock associated with refractory hypotension (BP<90/60) despite adequate fluid resuscitation and/or a serum lactate level ≥4.0 mmol/L. Multiple biomarkers have been evaluated to document sepsis and predict patient evolution to enhance medical care but are not integrated in the diagnosis or staging of sepsis. Most of these biomarkers are host proteins involved in the inflammatory response or associated with SIRS. No marker unquestionably distinguishes sepsis from SIRS caused by burn, trauma or surgery.

Severe sepsis and septic shock are rapidly evolving conditions in which delayed administration of empiric antimicrobial therapy is recognized to increase mortality by the hour. The multiple days required to obtain microbiological documentation makes empirical treatment an absolute necessity. The emergence of extensively drug resistant (XDR) bacteria challenges current therapeutic protocols for sepsis patients since a stereotyped empirical antimicrobial agents protocol is less likely to provide effective coverage of all the pathogens commonly encountered in any given clinical setting. Most concerning is the spread of carbapenem resistant Gram negative bacteria that commonly require the association of up to three molecules, the resistance to any agent being likely to generate resistance to the other molecules. As the requirement for antimicrobial documentation becomes more pressing, the current laboratory practices cannot provide microbiological documentation or antimicrobial susceptibility in the clinically relevant timeframes. It has been the clinical practice to document some infections by a "therapeutic trial". When suspecting an infection without microbiological documentation, physicians have been testing the hypothesis of the bacterial etiology of a clinical disorder by providing antibiotics and monitoring the clinical improvement of the patient under the treatment. A clinical improvement equated to a diagnosis of infection. In the absence of improvement over the duration of the "trial", the treatment was changed to encompass different pathogens or the infectious etiology was ruled out.

Moreover, while guidelines advise the revision of the antimicrobial regimen every 24 hours, the adequacy of the antimicrobial regimen is not necessarily apparent before several days and the use of biomarkers such as procalcitonin (PCT) do not yield the expected improvement in patient care. To this day, microbiology laboratory tests have had little impact on the management of sepsis patients.

The diagnosis of sepsis is currently purely clinical and the definition of sepsis is "SIRS in the context of infection." However, the generic symptoms of systemic inflammatory response syndrome (SIRS) (e.g., fever, chills, rigor, high heart/respiratory rates) are generally observed regardless of infection. Thus it is difficult to diagnose infections because local infections and blood-borne infections that can result in, e.g., sepsis, often produce similar generic symptoms (e.g., fever, chills, rigor, high heart/respiratory rates). Accordingly, there is an unmet need to develop an extremely rapid (<1 hr) sepsis diagnostic that can detect the presence of systemic infections in blood samples from patients even when blood cultures are negative and the ability to monitor the efficacy of antimicrobial treatment is key for further antibiotic susceptibility testing development.

SUMMARY

Embodiments of various aspects described herein are based on, at least in part, inventors' surprising and unexpected discovery that detection of a microbe in a sample can be enhanced by lysing or killing the cells before assaying with a pattern recognition receptor (PRR) (e.g., a lectin such as a mannose binding lectin, e.g., FcMBL) based detection method. In contrast to art known methods, e.g., blood cultures, which seek to increase the number of living or viable cells in a sample before assaying for presence or absence of microbes in the sample, the embodiments of the various aspects described herein do not rely on expansion of the living or viable cells in a sample, but are rather based on lysing or killing the cells to expose microbe-associated molecular patterns (MAMPs) for a subsequent PRR-based detection method in order to determine the presence or absence of microbes and/or MAMPs in the sample. By detecting levels of MAMPs in a sample, the sensitivity of the PRR-based detection method can be increased, which can allow for early diagnosis of a microbial infection.

The inventors have shown, in some embodiments, that lysing or killing microbes in a sample by mechanical treatment (e.g., beadmilling, sonication, or other functionally equivalent method to disrupt cell wall), and/or chemical treatment (e.g., antibiotics or other antimicrobial agents) can allow detection of encapsulated microbes such as *Klebsiella sp* that would not be otherwise detected. Thus, a simple pre-treatment of a sample to lyse or kill microbes can be performed prior to binding of the PRRs to exposed MAMPs. Therefore, this will not only increase the sensitivity of a PRR-based detection method, but can also surprisingly and significantly increase the spectrum of microbes that can be detected by a PRR-based detection method.

Additionally, the inventors have also applied the concept of a significant increase in detection signals from MAMPs released by lysed microbes to more effectively screen for antimicrobial agents and/or monitor antimicrobial activity of a treatment in a subject in need thereof. For example, the inventors have shown that detecting a reduced number of intact microbes (e.g., even by a three order of magnitude difference) is much less sensitive than detecting a significant increase in MAMPs due to lysis of microbes by an effective antibiotic within a specified time frame.

Accordingly, embodiments of various aspects described herein provide more sensitive assays and methods for detection of microbes and/or microbe-derived materials, e.g., MAMPs. Not only can the assays and methods described herein be used for early diagnosis of an infection, and/or diagnosis of infection caused by encapsulated or non-encapsulated pathogens that would be generally difficult to be detected, they can also be used for determining antimicrobial efficacy to identify a novel antimicrobial agent or composition, or for monitoring the efficacy of an antimicrobial treatment administered to a subject.

In one aspect, provided herein relates to a method of enhancing microbial detection in a sample by a PRR based MAMP capture/detection assay. Generally, the method comprises pre-treating the sample to lyse and/or kill the microbe before assaying for the microbe or components, or secretions thereof with a PRR based assay. In some embodiments, the method can further comprise detecting the presence or absence of components of microbes (e.g., MAMPs) with a PRR based assay such as a lectin based assay.

This method can also be used for detecting microbes that can generally escape detection with PRR based assays. Without wishing to be bound by theory, some microbes can escape detection by producing masking capsules or modifications of the exposed sugars (e.g., terminal sugars). The inventors have discovered that these microbes can be detected using the PRR based assay by first disrupting their architectural integrity by physical or chemical means. In one example, the inventors were able to detect *Klebsiella oxytoca* isolates, which were initially undetected by FcMBL enzyme linked lectin sorbent assay (ELLecSA), by using an embodiment of the assay or method described herein. Thus, provided herein is also a method of detecting microbes which are undetectable by a PRR based assay. The sample suspected of having a microbe can be pre-treated to lyse or kill the suspected microbe assaying for the components or secretions of the microbe (e.g., MAMPs). Accordingly, a method of expanding the microbial detection spectrum of a PRR based assay by pretreating a sample to lyse or kill microbes present in a sample prior to subjecting the sample to a PRR based assay for the presence or absence of microbes in the sample.

In another aspect, a method of determining efficacy of an antimicrobial treatment regimen in a subject is also provided herein. Generally, the method comprises providing a biological sample from a subject undergoing an antimicrobial treatment and assaying the biological sample with a PRR based assay. A treatment related change (e.g., increase or decrease or spike) in a detectable signal in the assay relative to a baseline level indicates that the antimicrobial treatment regimen is effective. Thus, in some embodiments, the method can further comprise (a) determining the antimicrobial treatment to be effective if a treatment related change (e.g., increase or decrease or spike) in a detectable signal relative to a baseline level is detected by the PRR based assay; or (b) determining the antimicrobial treatment to be ineffective if the treatment related change (e.g., increase or decrease or spike) relative to the baseline level is absent. When the antimicrobial treatment is determined to be ineffective, the subject can be administered with a different antimicrobial treatment regimen and the efficacy of the new treatment can be determined by repeating the method described herein.

In yet another aspect, a method of diagnosing an infection in a subject is provided herein. The method comprises providing a biological sample from a subject with or without having undergone an antimicrobial treatment, and assaying the biological sample with a PRR based assay. When the detectable signal level as determined by the PRR based assay is higher than a reference level, the subject is likely infected with at least one microbe. In some embodiments, when the detectable signal level as determined by the PRR based assay is higher than a reference level, e.g., by at least about 50%, at least about 60%, at least about 70%, at least about 80%, at least about 90%, at least about 95% or more, the subject is likely infected with at least one microbe. In some embodiments, when the detectable signal level as determined by the PRR based assay is higher than a reference level, e.g., by at least about 1.1-fold, at least about 1.2-fold, at least about 1.3-fold, at least about 1.4-fold, at least about 1.5-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold or more, the subject is likely infected with at least one microbe. In some embodiments, the reference level can correspond to a MAMP level in a non-infected subject.

In some embodiments, the detectable signal level as determined by the PRR based assay is not induced by trauma.

In some embodiments, the method can further comprise administering an antimicrobial treatment to the subject. A treatment related change or rate of change (e.g., increase or decrease or spike) in a detectable signal in the assay relative to a baseline level indicates infection with a pathogen susceptible to the antimicrobial treatment. Thus, in some embodiments, the method can further comprise (a) identifying the pathogen species or genus that is susceptible to the administered antimicrobial treatment if a treatment related change or rate of change (e.g., increase or decrease or spike) in a detectable signal relative to a baseline level is detected by the PRR based assay; or (b) performing additional assay and/or administering to the subject with a different antimicrobial treatment if the treatment related change or rate of change (e.g., increase or decrease or spike) relative to the baseline level is absent.

In one aspect, provided herein relates to a method of determining efficacy of an antimicrobial treatment regimen in a subject. The method comprise (a) assaying at least one biological sample with a pattern recognition receptor (PRR)-based assay for the presence of microbe associated molecular patterns (MAMPs), wherein the biological sample is collected from the subject who has been administered the antimicrobial treatment for no longer than a pre-determined period of time; (b) comparing the detectable signal level of MAMPs obtained from (i) to a baseline level; and (c) identifying the antimicrobial treatment to be effective if a treatment related change in the detectable signal level relative to the baseline level is present; or identifying the antimicrobial treatment to be ineffective if the treatment related change in the detectable signal level relative to the baseline level is absent.

In some embodiments, the pre-determined period of time is selected based on, e.g., the kinectics of the expected microbe proliferation and/or pharmacokinetics/pharmacodynamics (PK/PD) of an antimicrobial agent, e.g., kinetics of MAMPs released by the microbes upon contact with the antimicrobial agent. In some embodiments, the pre-determined period of time can be selected such that the treatment-related effect of MAMP release dominates over the microbe proliferation and shedding. In some embodiments, the pre-determined period of time can be no longer than 3 days, no longer than 2 days, no longer than 1 day. In some embodiments, the pre-determined period of time can be no longer than 24 hours, no longer than 18 hours, no longer than 12 hours, no longer than 9 hours, no longer than 6 hours, no longer than 5 hours, no longer than 4 hours, no longer than 3 hours, no longer than 2 hours, no longer than 1 hour, no longer than 30 minutes or less. For example, fast-acting antibiotics (e.g., but not limited to Amikacin) can produce a treatment-related effect of MAMP release in less than 4 hours, less than 2 hours, or less than 1 hour. In contrast, slow-acting antibiotics would require longer time to produce a treatment-related effect of MAMP release, a longer pre-determined period of time can be selected.

In some embodiments, the baseline can correspond to the level of MAMPs before the administration of the antimicrobial treatment.

In some embodiments, the treatment related change can be at least about 50%, at least about 60%, at least about 70%, at least about 80%, at least about 90%, or more relative to the baseline. In some embodiments, the treatment related change can be at least about 1.1-fold, at least about 1.2-fold, at least about 1.3-fold, at least about 1.4-fold, at least about 1.5 fold, at least about 2-fold, at least about 3-fold, at least about 4-fold, at least about 5-fold, at least about 6-fold or more from the baseline level.

In some embodiments when the subject has a high baseline of MAMP level, the antimicrobial treatment can be identified to be effective if a treatment related decrease in the detectable signal level relative to the baseline level is present. In some embodiments, the subject previously underwent an ineffective antimicrobial treatment before the onset of a different antimicrobial treatment. In these embodiments the subject's infection can progress such that microbes proliferate and shed high levels of MAMPs, resulting in a high MAMP baseline. When a different antimicrobial treatment administered to a subject is effective, the MAMP detectable signal level can decrease relative to the high MAMP baseline (e.g., due to the MAMPs being cleared and no new MAMPs are generated). In some embodiments where an antimicrobial treatment is effective, the MAMP detectable signal level can increase relative to the high MAMP baseline for a period of time before the decrease (e.g., due to lysis and/or killing of microbes followed by MAMPs being cleared and no new MAMPs are generated). Accordingly, depending on when a sample is taken from a subject during the course of an antimicrobial treatment, the direction of change in MAMP detectable signal level can change accordingly.

In some embodiments when the subject has a low baseline of MAMP level, the antimicrobial treatment can be identified to be effective if a treatment related increase in the detectable signal level related to the baseline level is present. Without wishing to be bound by theory, the treatment related increase in the detectable signal level can be induced by MAMPs released or exposed by microbes after contact with the antimicrobial treatment. In some embodiments, the subject, who initially shows a low MAMP baseline, is diagnosed for having an infection at the early stage, or having a risk of developing an infection.

In still another aspect, provided herein relates to a method of adapting or optimizing an antimicrobial treatment regimen for a subject in need thereof. The method comprises providing a biological sample from a subject, who is administered a broad spectrum antimicrobial treatment, and assaying the biological sample with a PRR based assay. A first different spectrum antimicrobial treatment can be administered to the subject if a treatment related change (e.g., increase, decrease, or spike) in a detectable signal relative to a baseline level is detected with the PRR based assay upon treatment with the broad spectrum antimicrobial treatment. If little or no treatment related change (e.g., increase, decrease, or spike) in the detectable signal relative to a baseline level is detected after administration of the first different spectrum antimicrobial treatment, a second different spectrum antimicrobial treatment can be administered to the subject. Administering with different spectrum antimicrobial treatments and subjecting a sample to a PRR-based assay can be repeated until a treatment related change (e.g., increase, decrease, or spike) in the detectable signal relative to a baseline level is detected by the PRR based assay.

In still yet another aspect, a method of monitoring in vivo activity of an antimicrobial agent in a subject suspected of having a microbe infection is provided herein. The method comprises providing a biological sample from a subject undergoing an antimicrobial treatment with the antimicrobial agent and assaying the biological sample with a PRR based assay. A treatment related change (e.g., increase, decrease, or spike) in a detectable signal in an assay relative to a baseline level indicates that the antimicrobial agent is active against the suspected pathogen infection.

A method of screening for an effective antimicrobial agent is also provided herein. The method comprises: contacting a sample comprising microbes to be treated, with a candidate antimicrobial agent for varying amount of times; subjecting the sample treated for the varying amount of times to a PRR based assay for detecting release of microbe-associated molecular patterns (MAMPs) induced by the candidate antimicrobial agent; and either (a) identifying the candidate antimicrobial agent to be effective if the kinetics of the MAMP release indicates an change (e.g., increase, decrease, or spike) in a detectable signal relative to a baseline level; or (b) identifying the candidate antimicrobial agent to be ineffective if the kinetics of the MAMP release does not indicate a change, e.g., no significant increase or decrease or spike, relative to the baseline level.

Depending on applications and/or when the baseline is determined over the course of infection and/or over the course of an antimicrobial treatment, the baseline level can vary in the methods of various aspects described herein. In some embodiments of some aspects described herein, a baseline level can correspond to a signal (e.g., MAMP signal level) resulted from assaying the same sample with a PRR based assay without pre-treating the sample to lyse or kill microbes. In some embodiments of some aspects described herein, a baseline level can correspond to a signal (e.g., MAMP signal level) resulted from assaying a sample collected from a subject prior to administration of an antimicrobial treatment, with a PRR based assay. In some embodiments of some aspects described herein, a baseline level can correspond to a signal (e.g., MAMP signal level) resulted from assaying a sample collected from a subject at a first time point after administration of an antimicrobial treatment, with a PRR based assay. In some embodiments of some aspects described herein, a baseline level can correspond to a signal (e.g., MAMP signal level) resulted from a PRR based assay of a sample that was collected from a subject prior to administration of an antimicrobial treatment and has subsequently been cultured in vitro under a physiological condition for substantially the same amount of time after the subject has been given the antimicrobial treatment. In some embodiments of various aspects described herein, a baseline level can correspond to an infection baseline as defined herein.

In some embodiments of various aspects described herein involving an antimicrobial treatment, the method can further comprise generating a time course profile that indicates the amount of microbes or microbial matter (e.g., MAMPs) present in the sample before and after administration of the antimicrobial treatment. In some embodiments, the time course profile can comprise at least 2 time points, including a time point before the antimicrobial treatment and a time point taken after the antimicrobial treatment. In some embodiments, the time course profile can comprise at least 3 time points, including a time point before the antimicrobial treatment and a plurality of time points taken after the antimicrobial treatment.

Depending on types of the microbes, antibiotic treatment and/or patients, the change in the detectable signal level (e.g., corresponding to the change in MAMP level) before and after the administration of the antimicrobial treatment can correspond to an increase in MAMP level or a decrease in MAMP level.

In some embodiments, a time course profile that displays an increase (e.g., a sharp increase) in the PRR-based assay signal corresponding to a time point after the antimicrobial treatment, relative to a baseline, can indicate an effective antimicrobial treatment. For example, a patient is diagnosed early for an infection (e.g., using the methods described herein) and thus administered with an antimicrobial treatment. An effective treatment can induce an increase in MAMP level (e.g., due to lysis and/or killing of the microbes in a subject) in a sample collected from a subject after the treatment. In some embodiments, a time coure profile indicating an effective antimicrobial treatment can further display a decrease and/or a plateau in signal at later time points. Without wishing to be bound by theory, in some embodiments, the decrease and/or a plateau in signal can correspond to clearance of the MAMPs in the subject.

In other embodiments, a time course profile that displays a decrease (e.g., a sharp decrease) in the PRR-based assay signal corresponding to a time point after the antimicrobial treatment, relative to a baseline, can indicate an effective antimicrobial treatment. For example, a patient was previously administered with an antimicrobial treatment but it was not effective. Thus, the baseline of the PRR-based assay can be initially high (e.g., due to microbe proliferation and shedding MAMPs). If this subject is now administered with a different antimicrobial treatment which is effective for treating the infection, the PRR based assay can show a decrease in the detectable MAMP signal level. In some embodiments, the decrease in the detectable MAMP signal level can be due to treatment-induced suppression of the infection and/or clearance of the MAMPs in the subject.

As used interchangeably herein and throughout the specification, the terms "PRR based assay," "PRR based MAMP capture/detection assay" and variants thereof refer to a method/assay and/or composition used to bind a microbe and/or microbial matter (e.g., MAMPs) comprising use of at least one pattern recognition receptor (PRR), e.g., CRP, MBL (including FcMBL) or lectin, etc. In some embodiments, a PRR based assay can refer to capture of a microbe and/or microbial matter (e.g., MAMPs) comprising use of at least one PRR. In some embodiments, a PRR based assay can refer to use of at least one PRR to provide a detectable signal in the presence of a microbe and/or microbial matter (e.g., MAMPs). In some embodiments, a PRR based assay can refer to use of at least two PRRs to capture a microbe and/or microbial matter (e.g., MAMPs) and also to provide a detectable signal in the presence of the microbe and/or microbial matter (e.g., MAMPs). In these embodiments, the same PRRs or different PRRs can be used in both the capture and signal detection steps. The PRR can be a naturally occurring or a recombinant molecule. The molecule can also be fusion protein comprising at least a part of a PRR and at least a part of a second protein or peptide, e.g., but not limited to an Fc portion of an immunoglobulin or another microbe-binding molecule. An exemplary PRR can be mannan binding lectin (MBL) or other mannan binding molecules. Another exemplary PRR can be C-reactive protein (CRP). By way of example only, in a PRR-based assay where the PRR is a lectin (including, e.g., MBL and/or FcMBL), the PRR-based assay is also called a lectin-based assay (e.g., MBL-based assay or FcMBL-based assay). Similarly, in a PRR based assay where the PRR comprises a CRP, the PRR-based assay can be called a CRP based assay.

In some embodiments, the PRR based assay can comprise use of at least one PRR (e.g., a lectin such as a mannan binding lectin or molecule, or C-reactive protein) bound to a solid substrate for capturing or isolating the microbe or microbial matter from the sample for subsequent detection. Examples of solid substrate can include, but are not limited to, beads or particles (including nanoparticles, microparticles, polymer microbeads, magnetic microbeads, and the like), filters, fibers, screens, mesh, tubes, hollow fibers, scaffolds, plates, channels, gold particles, magnetic materials, medical apparatuses (e.g., needles or catheters) or implants, dipsticks or test strips, filtration devices or membranes, hollow fiber cartridges, microfluidic devices, mixing elements (e.g., spiral mixers), extracorporeal devices, and other substrates commonly utilized in assay formats, and any combinations thereof. In some embodiments, the solid substrate can be a magnetic particle or bead.

In some embodiments, the PRR based assay can comprise use of at least one PRR (e.g., a lectin such as mannan binding lectin or molecule) conjugated with a detectable label for detecting the microbe or microbial matter in the sample or isolated from the sample.

In some embodiments of various aspects described herein, the PRR based assay can be based on enzyme linked lectin sorbent assay (ELLecSA). As used interchangeably herein, the term "enzyme linked lectin sorbent assay" or "ELLecSA" refers to an assay that uses at least one lectin and color change to detect or determine the presence of a microbe or microbial matter, e.g., MAMPs, in a sample. By extension, and because ELLecSA relies on the same concept of binding a microbe associated molecular pattern (MAMP) with a surface-tethered or coated pattern recognition receptor (PRR) and/or detecting the MAMP using a labeled PRR without using antibodies, other PRR that are not lectins (e.g., but not limited to the pentraxin family C-Reactive Protein) used to capture and/or detect non-carbohydrate MAMPs (e.g., Phosphocholine) are also encompassed in the term "enzyme linked lectin sorbant assay" or "ELLecSA." The working principle of ELLecSA is similar to art known enzyme-linked immunosorbent assay (ELISA), except that lectins (or other PRRs) are used in ELLecSA, while antibodies are used in ELISA. Thus, in some embodiments, an ELLecSA assay can be a dual PRR sandwich ELLecSA, in which a PRR-based molecule is used to capture a microbe or microbial matter (e.g., MAMPs), and an enzyme-linked PRR-based molecule is used as a detection PRR that also binds to the captured microbe or microbial matter, wherein the enzyme converts a chemical substrate to be added into a color or fluorescent or electrochemical signal.

In some embodiments of various aspects described herein, the treatment related change in detectable MAMP signal level can refer to degree or extent of change in detectable MAMP signal level relative to a baseline level. For example, the treatment related change in detectable MAMP signal level can refer to a degree or extent of increase or decrease in detectable MAMP relative to a baseline level.

In some embodiments of various aspects described herein, the treatment related change in detectable MAMP signal level can also refer to the rate of change in detectable MAMP signal level relative to a baseline level. In some embodiments, the treatment related change in detectable MAMP signal level can refer to the rate of increase in detectable MAMP signal level being higher than the rate of increase in a control sample (e.g., a sample without an antimicrobial treatment or a sample with an ineffective antimicrobial treatment). In some embodiments, the treatment related change in detectable MAMP signal level can refer to the rate of decrease in detectable MAMP signal level being higher than the rate of decrease in a control sample (e.g., a sample without an antimicrobial treatment or a sample with an ineffective antimicrobial treatment).

FIGS. 4A-4B show that FcMBL detection of bacteria is significantly enhanced by mechanical and antibiotic killing of *Enterobacter aerogenes*. (FIG. 4A) Detection in serum of a 2 hr culture. (FIG. 4B) Detection in blood of a 4 hr culture. In some embodiments, sonication at 125 W for 10 min could be further followed by 10 min beadmill (30 Hz) with 0.1 mm zirconium beads.

Figure 5A:
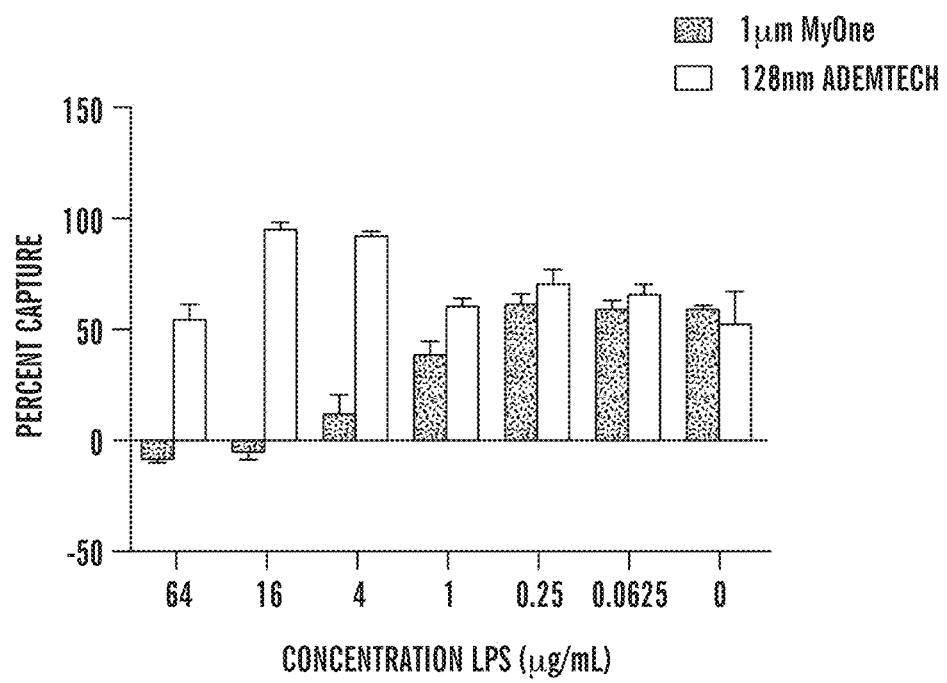
Figure 5B:
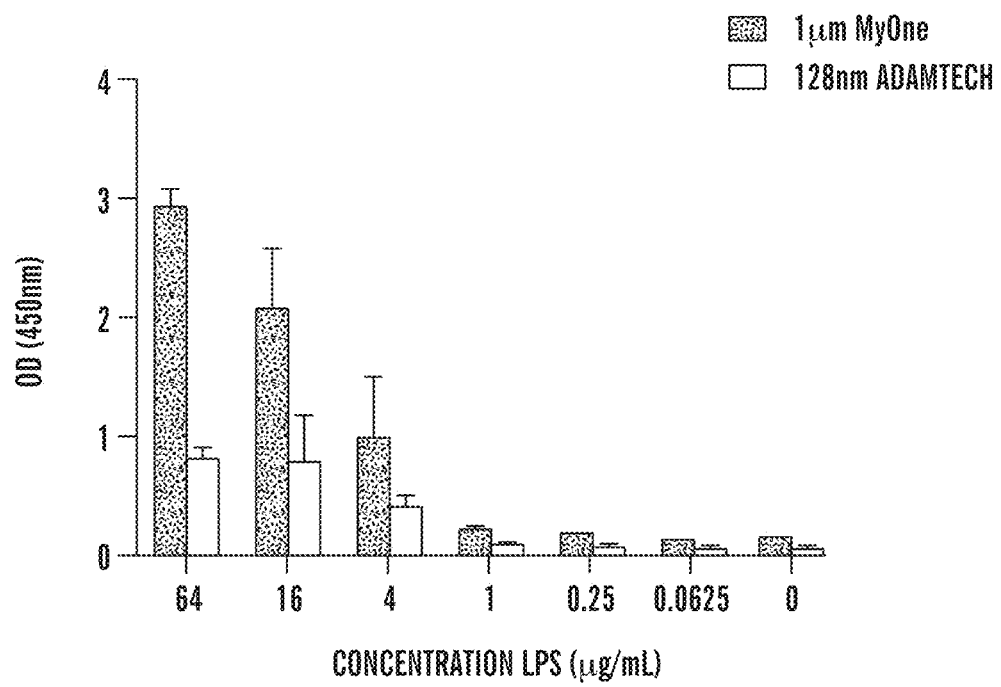

FIG. 5A-5B show that disrupted versus whole bacteria capture is bead size dependent. (FIG. 5A) LPS titers were used to determine capture capabilities of 10e5 *E. coli*. Capture was quantified by culturing of unbound bacteria. (FIG. 5B) FcMBL ELLecSA was used to quantify the capture of LPS titers versus 10e5 *E. coli*.

Figure 6:
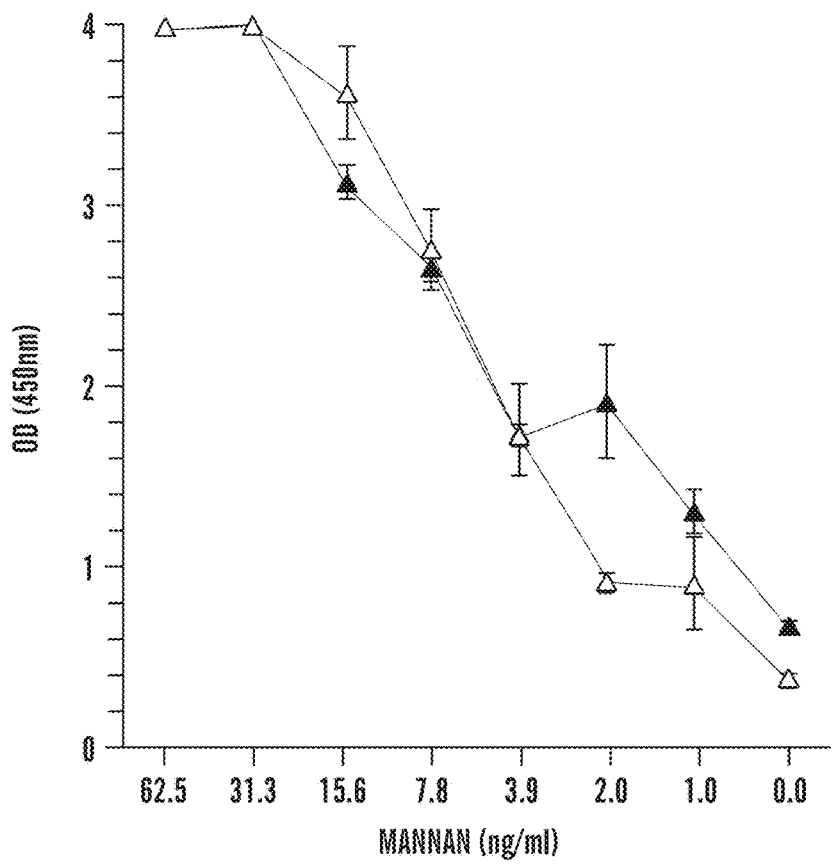

FIG. 6 shows that FcMBL bead capture—recombinant MBL-HRP detection increases the sensitivity of mannan detection in buffer and whole blood: FcMBL beads were used to capture serial titers of mannan in either TBST Ca++ buffer, or EDTA blood.

Figure 7:
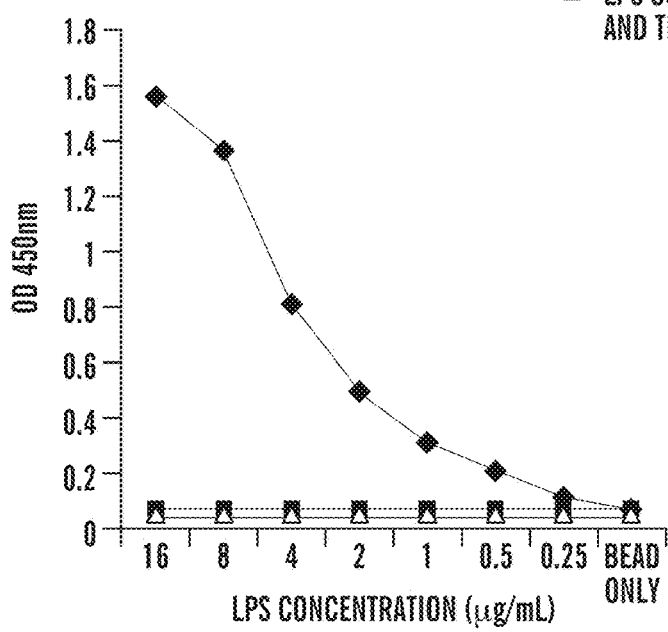

FIG. 7 shows specific capture of LPS by FcMBL beads is Ca++ dependent. Capture of LPS titers in TBST Ca++ was performed in the presence or absence of EDTA. Capture of LPS titer in blood was performed in the presence of EDTA.

Figure 8A:
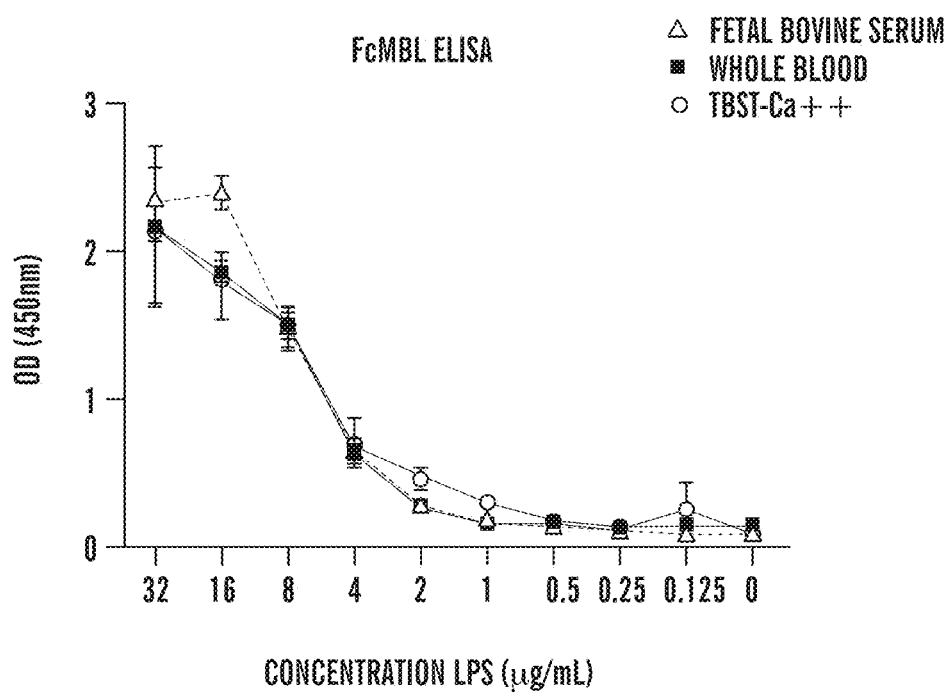
Figure 8B:
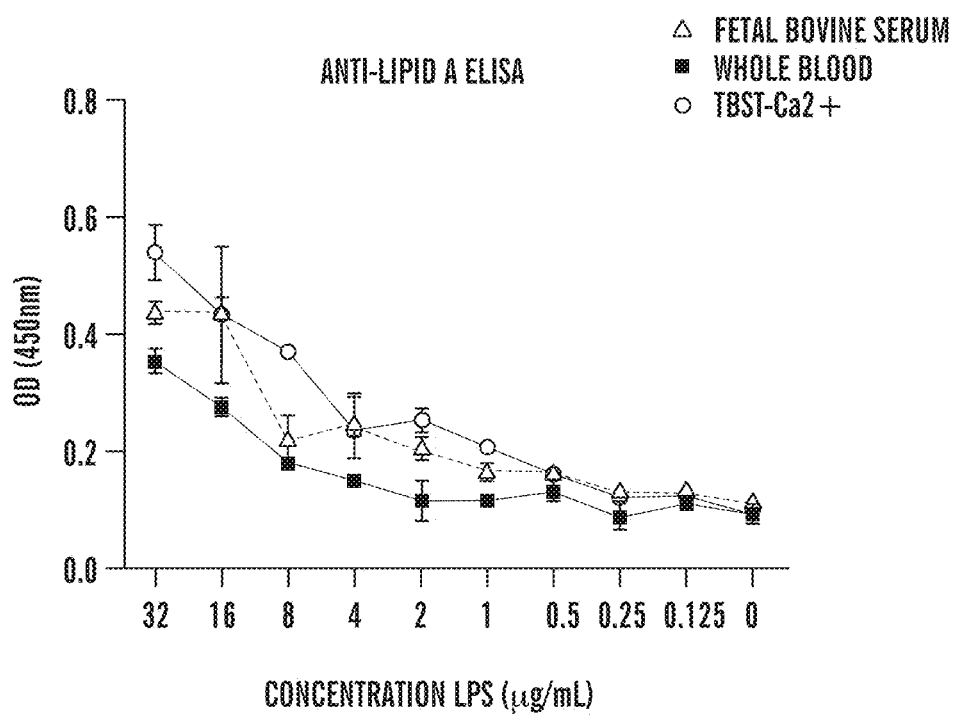

FIGS. 8A-8B show that FcMBL beads capture LPS. FcMBL beads were used to capture serial titers of LPS in eitherTBST Ca++ buffer, FBS TBST Ca++, buffer, or EDTA blood. (FIG. 8A) LPS capture as measured by FcMBL ELLecSA. (FIG. 8B) LPS capture as measured by anti-LPS ELISA (NOVUS).

Figures 9A, 9B:
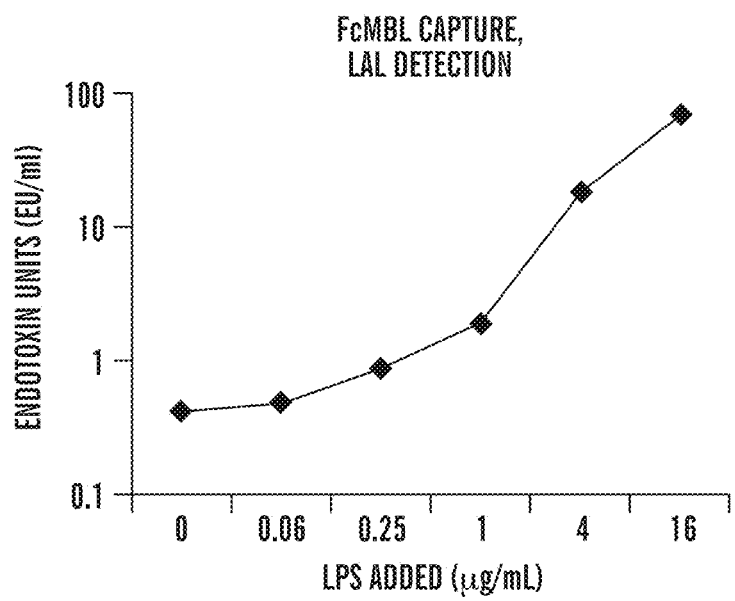

FIGS. 9A-9B present Limulus Amebocyte Assay measurement of LPS capture by FcMBL beads. (FIG. 9A) Limulus Amebocyte Assay was used to quantify LPS titer capture by FcMBL beads from TBST Ca++ (FIG. 9B) Quantification of LPS capture by FcMBL beads added to either TBST Ca++, FBS TBST Ca++, of EDTA blood.

Figure 10:
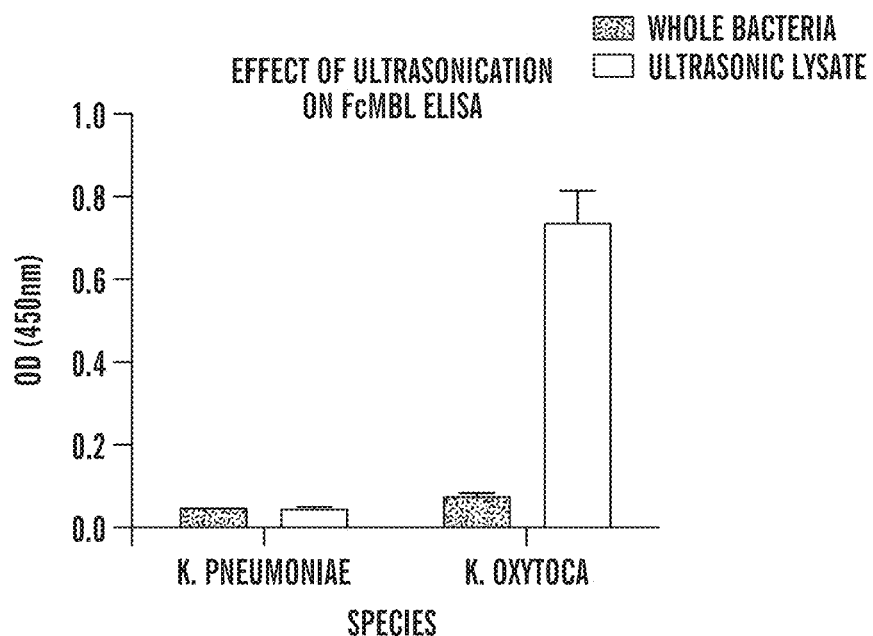

FIG. 10 shows ultrasonic release of binding moieties—detection of FcMBL-negative *K. oxytoca*. An overnight culture of *K. oxytoca* (Koxy) and *K. pneumoniae* (Kpn) was diluted 10 fold, sonicated or not for 15 minutes at 125 watts and submitted to the FcMBL ELLecSA.

Figure 11:
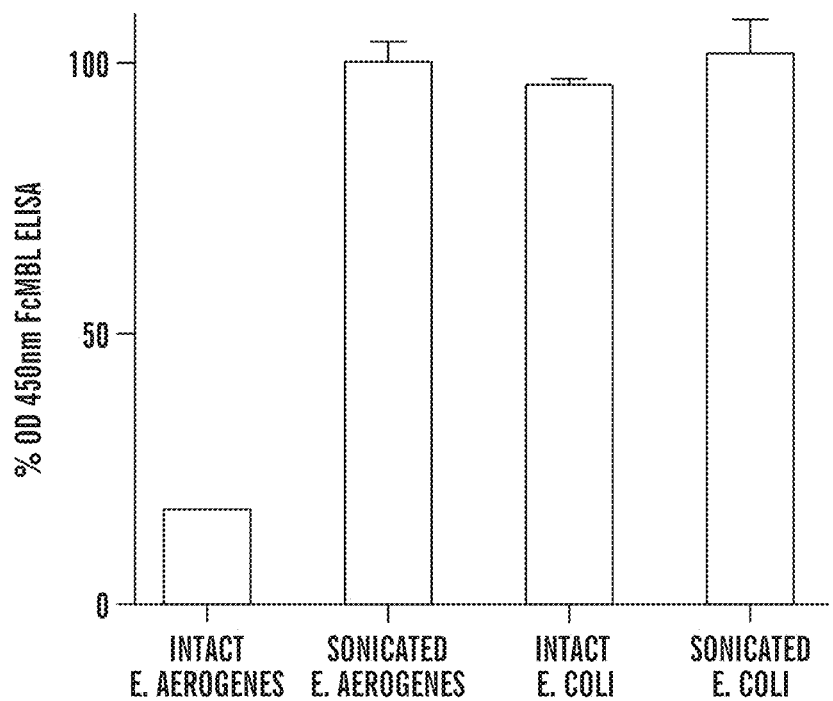

FIG. 11 shows that detection of bacteria by FcMBL ELLecSA is enhanced by mechanical disruption. For example, sonication/bead mill treatment of bacteria can improve FcMBL ELLecSA detection of pathogens. Intact *Enterobacter aerogenes* whole and disrupted, were assayed for FcMBL capture (1 μM FcMBL beads) and detection by FcMBL ELLecSA. For fragment generation bacteria were beadmilled and sonicated. The results were compared with *E. coli* capture (sonicated and whole). *E. coli* are used as positive FcMBL ELLecSA control as they bind FcMBL efficiently both intact and disrupted/lysed compared to many pathogenic species that encapsulate themselves to evade immune responses.

Figure 12A:
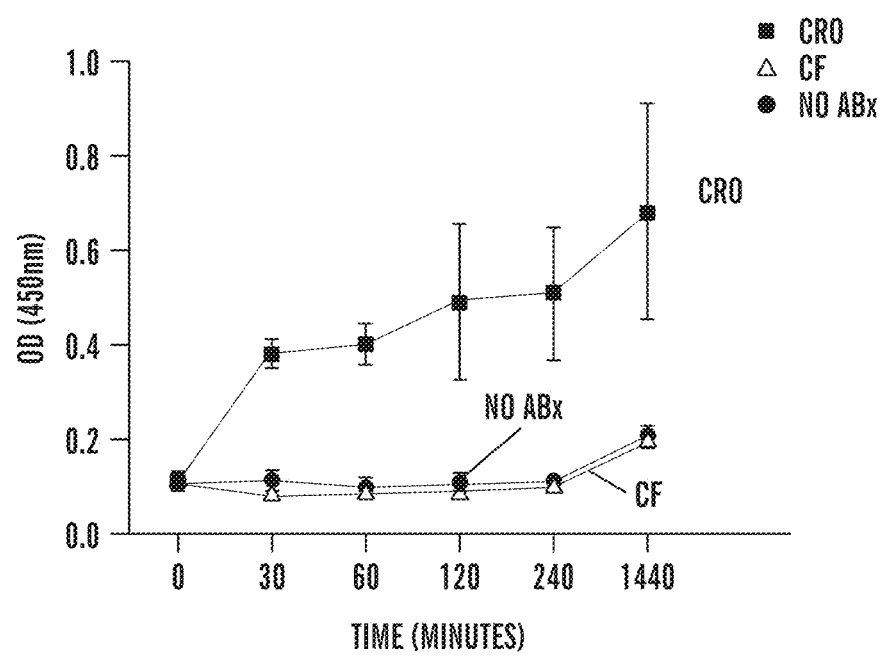
Figure 12B:
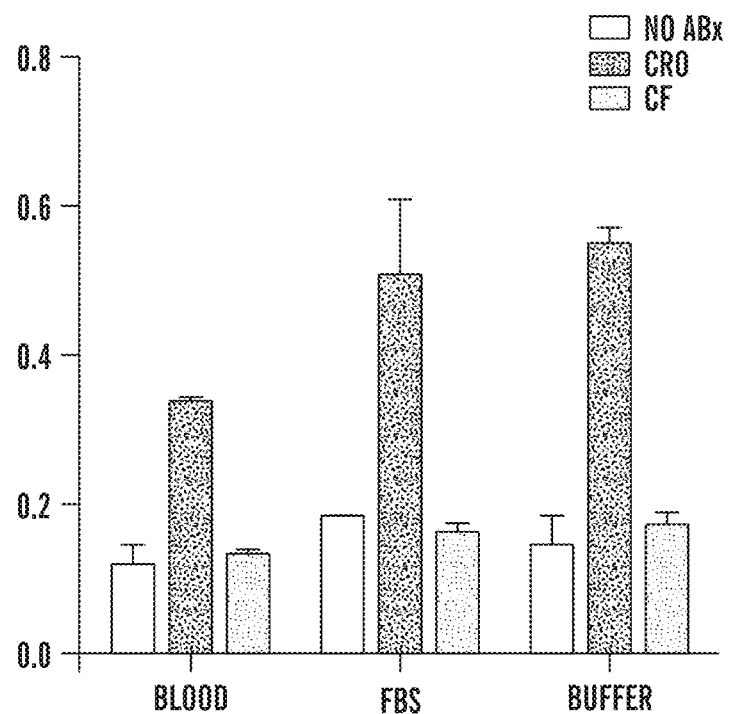

FIGS. 12A-12B show that efficacy of antibiotic treatment can be tracked by FcMBL ELLecSA detection of *E. cloacae* MAMPs. In FIG. 12A, FcMBL ELLecSA determination of Ceftriaxone (CRO) and Cefazoline (CF) treatment efficacy. *E. cloacae* (whole bacteria are not detected by FcMBL) were chosen as a test pathogen because 1$^{st}$ generation *E. cloacae* are Ceftriaxone susceptible/Cefazoline resistant. *E. cloacae* (10e8 CFU/ml) were treated with 1 mg/ml antibiotic and aliquots assayed by FcMBL ELLecSA at the indicated time points. FIG. 12B shows that antibiotic efficacy can be determined in complex media including FBS and whole blood. *E. cloacae* were added to each medium with or without antibiotic and assayed by FcMBL ELLecSA at 2 hours post treatment.

Figure 13A:
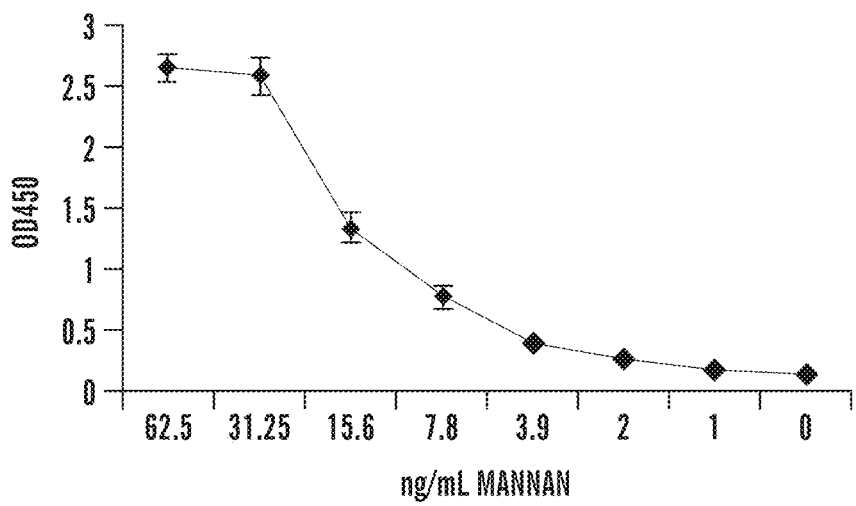
Figure 13B:
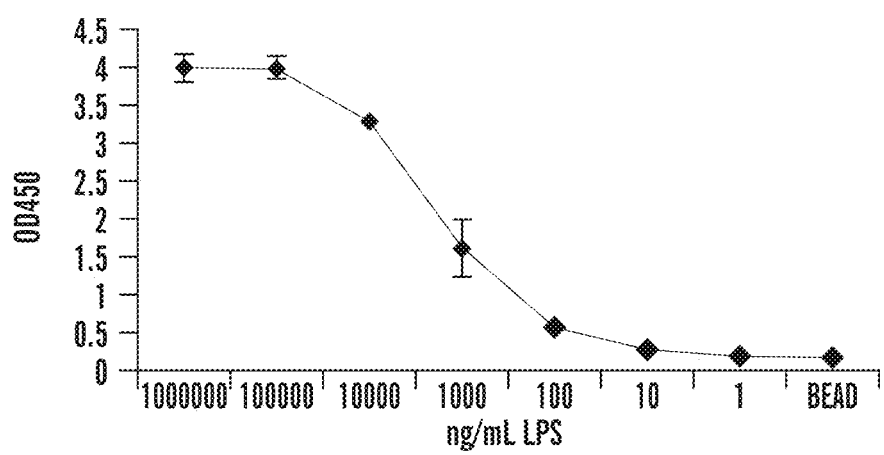
Figure 13C:
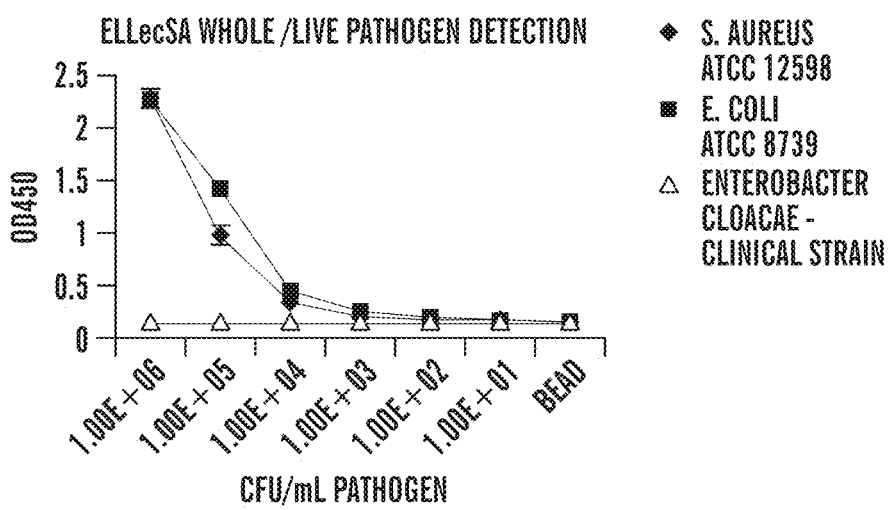
Figure 13D:
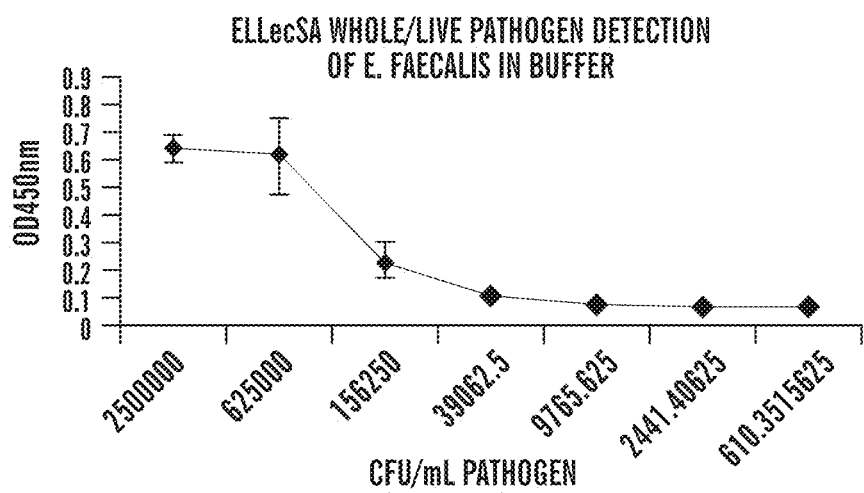
Figure 13E:
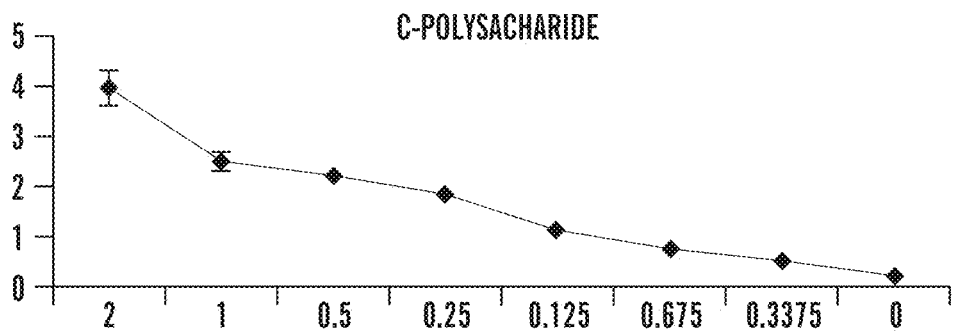

FIGS. 13A-13E show ELLecSA detection of microbe associated molecular patterns (MAMPs) in buffer. FIG. 13A shows ELLecSA detection of mannan in TBST-5 mM Ca++. FcMBL coated beads were used to detect serial dilutions of mannan using the ELLecSA. 1:5000 rhMBL-HRP was used as a detection agent. Quantification was determined at OD450 nm. FIG. 13B shows ELLecSA detection of LPS in TBST-5 mM Ca++. FcMBL coated beads were used to detect serial dilutions of LPS using the ELLecSA. 1:5000 rhMBL-HRP was used as a detection agent. Quantification was determined at OD450 nm. FIG. 13C shows ELLecSA detection of whole live pathogens in TBST-5 mM Ca++. FcMBL coated were used to capture pathogens grown to 0.5 McFarland and serially diluted and detected using the ELLecSA. 1:5000 rhMBL-HRP was used as a detection agent. Quantification was determined at OD450 nm. FIG. 13D shows ELLecSA detection of whole live pathogens in TBST-5 mM Ca++. CRP coated beads were used to capture pathogens grown to 0.5 McFarland and serially diluted and detected using the ELLecSA. 1:5000 CRP-HRP was used as a detection agent. Quantification was determined at OD450 nm. FIG. 13E shows ELLecSA detection of C-polysaccharide in TBST-5 mM Ca++. CRP coated beads were used to bind to C-polysaccharide that was serially diluted and detected using the ELLecSA. 1:5000 CRP-HRP was used as a detection agent. Quantification was determined at OD450 nm.

Figure 14:
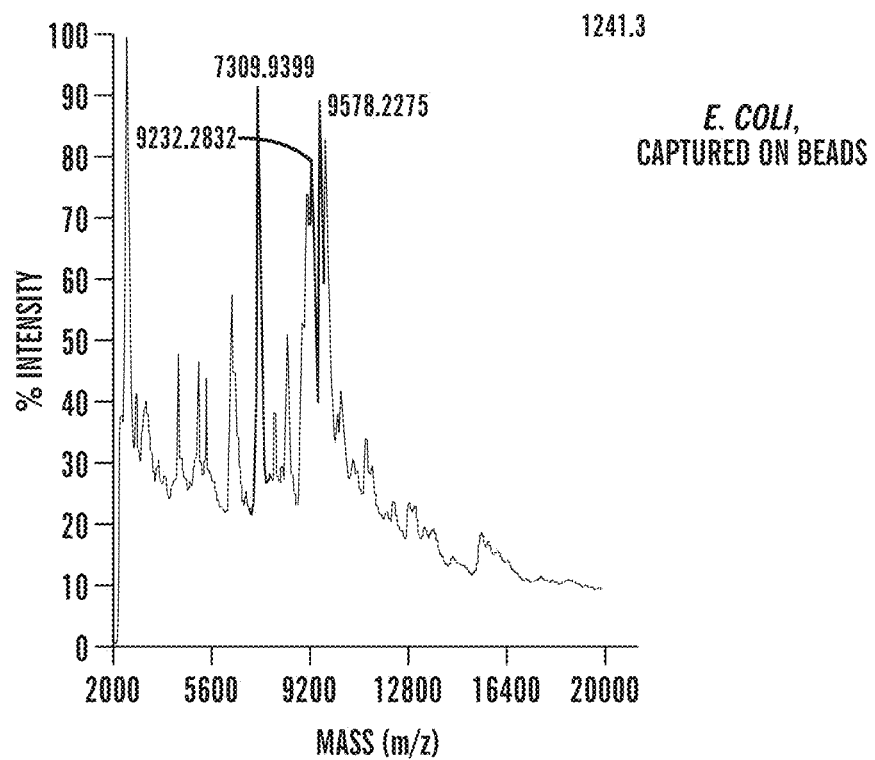
Figure 14:
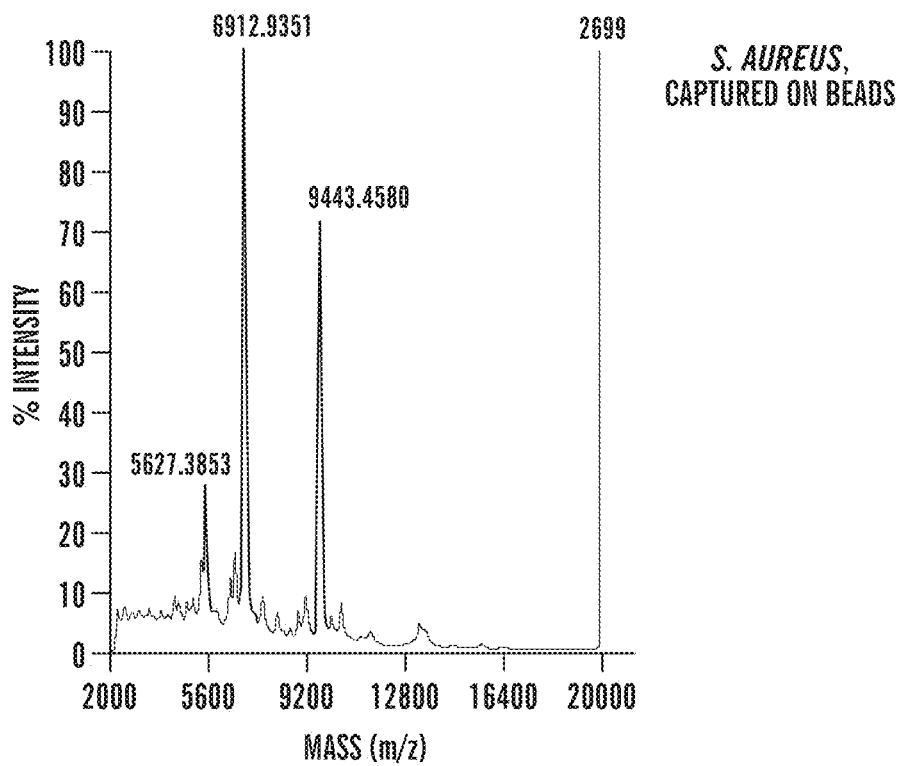
Figure 14:
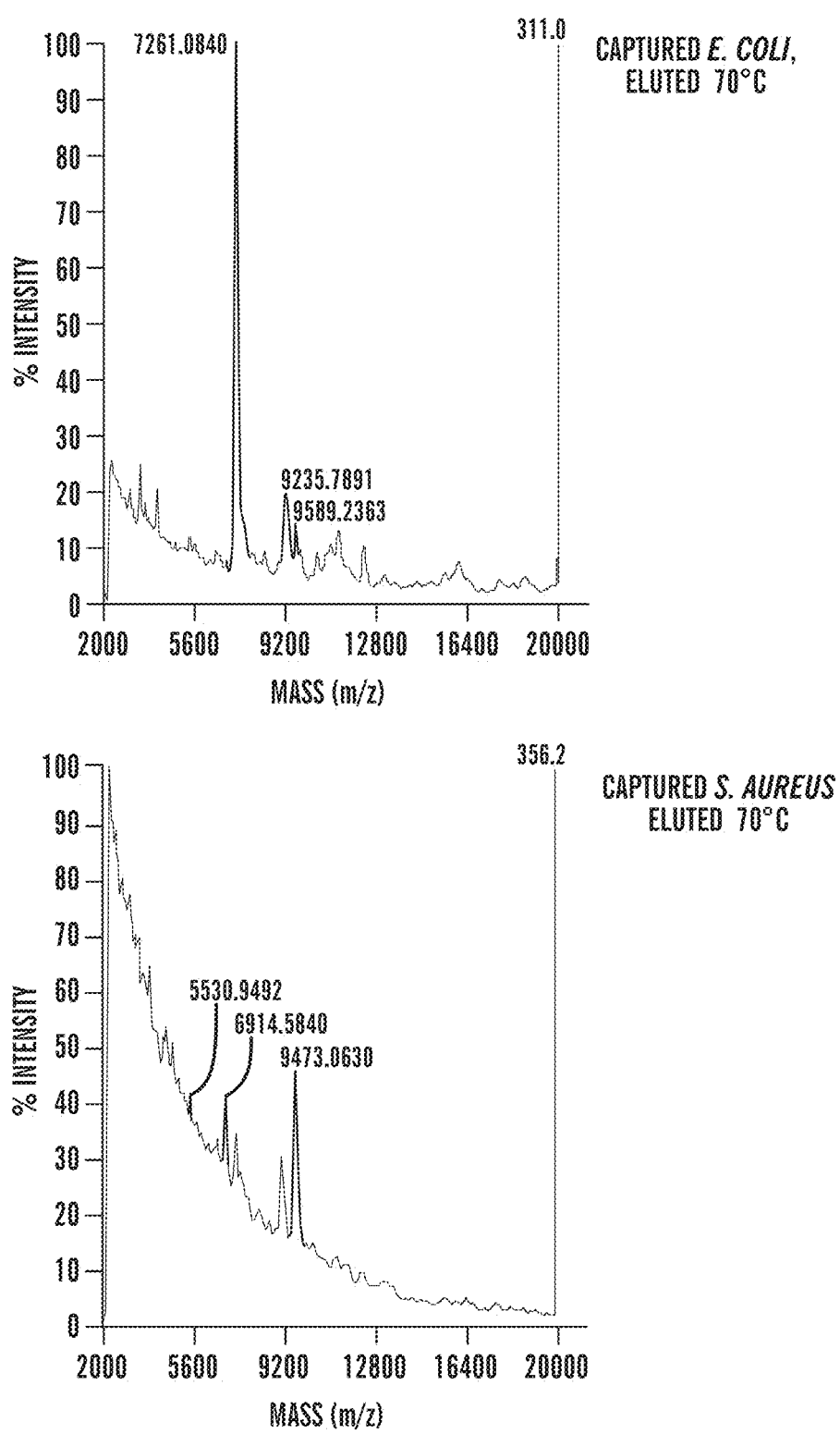

FIG. 14 shows identification of microbes captured by FcMBL beads using MALDI-TOF MS. FcMBL beads were used to capture material from late log phase cultures of *E. coli, S. aureus*. The beads were subjected to positive and negative voltage MALD-TOF MS using DHB as a matrix. Native beads or 70 degrees distilled water eluted material was analyzed and species specific peaks detected.

Figure 15A:
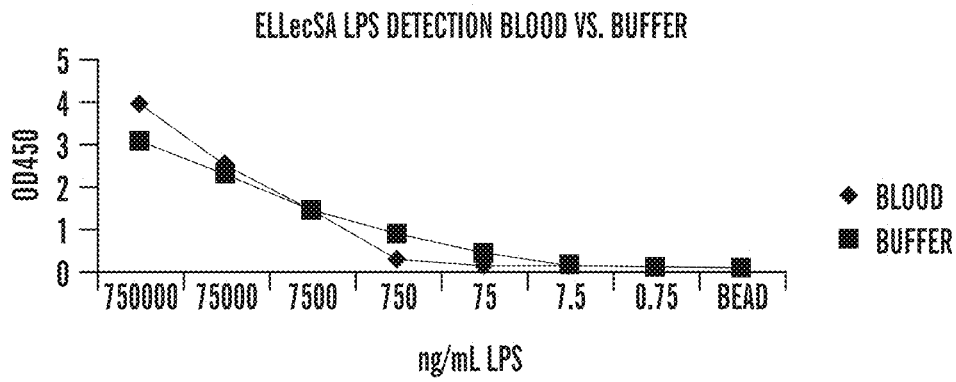
Figure 15B:
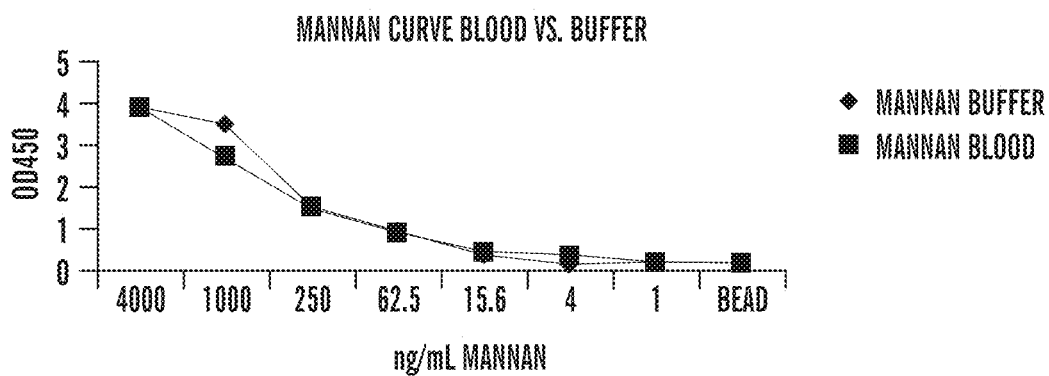
Figure 15C:
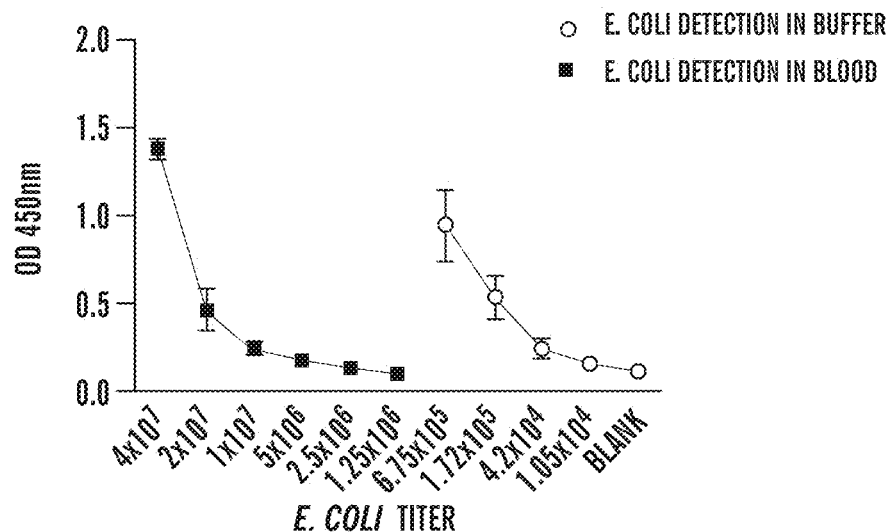

FIGS. 15A-15C show ELLecSA detection of MAMPs in blood. FIG. 15A shows ELLecSA detection of LPS in both human donor blood and TBST-5 mM Ca++. FcMBL coated beads were used to detect serial dilutions of LPS from *E. coli* 011:B4 using the ELLecSA. 1:5000 rhMBL-HRP was used as a detection agent. Quantification was determined at OD450 nm. FIG. 15B shows ELLecSA detection of Mannan in both human donor blood and TBST-5 mM Ca++. FcMBL coated beads were used to detect serial dilutions of Mannan using the ELLecSA. 1:5000 rhMBL-HRP was used as a detection agent. Quantification was determined at OD450 nm. FIG. 15C shows detection of *E. coli* ATCC 8739 whole cells in blood and buffer.

Figure 16A:
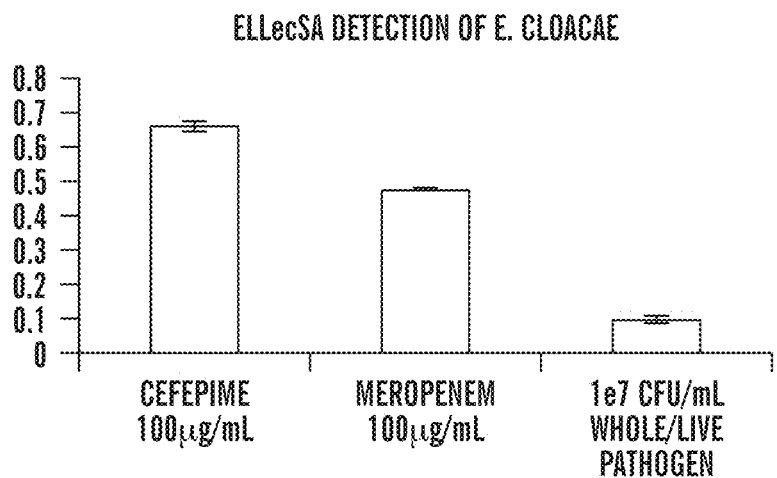
Figure 16B:
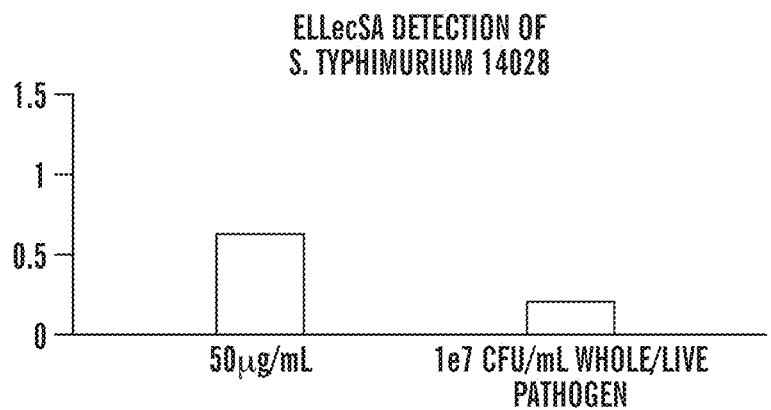
Figure 16C:
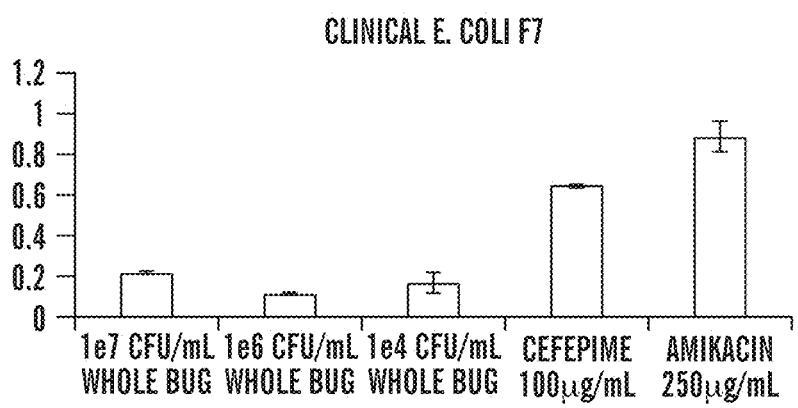
Figure 16D:
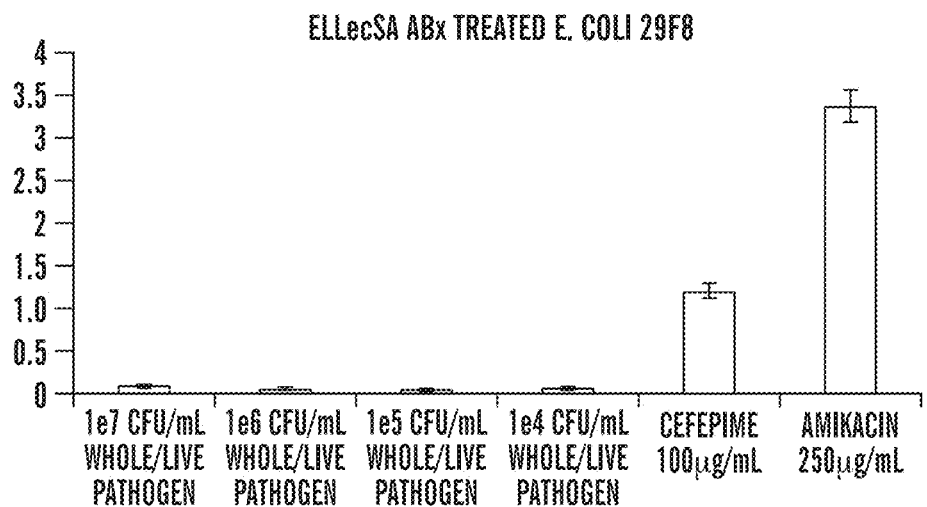
Figure 16E:
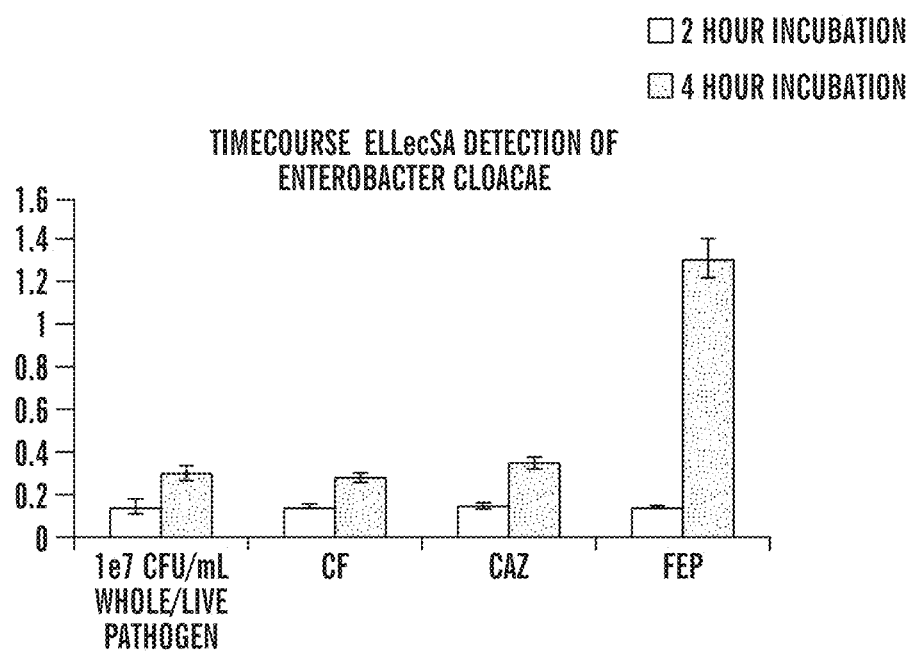

FIGS. 16A-16E show lysing microbes by antibiotic treatment to increase MAMPs for FcMBL-coated bead capture and ELLecSA detection. In FIG. 16A, FcMBL coated beads were used to detect the presence of MAMPs from a clinical isolate of *Enterobacter cloacae* after 4 hour treatments of cefepime and meropenem. Detection of MAMPs was done by ELLecSA using rhMBL-hrp. In FIG. 16B, FcMBL coated beads were used to detect the presence of MAMPs from a clinical isolate of *Salmonella typhimurium* after 4 hour treatments of cefepime. Detection of MAMPs was done by ELLecSA using rhMBL-hrp. In FIG. 16C, FcMBL coated beads were used to detect the presence of MAMPs from a clinical isolate of *E. coli* after 4 hour treatment of cefepime and amikacin. Detection of MAMPs was done by ELLecSA using rhMBL-hrp. In FIG. 16D, FcMBL coated beads were used to detect the presence of MAMPs from a clinical isolate of E. coli after 4 hour treatment of cefepime and amikacin. Detection of MAMP's was done by ELLecSA using rhMBL-hrp. This strain of E. coli was sensitive to amikacin but only showed an intermediate susceptibility to cefepime (MIC of 2 mg), which correlates to the shedding of less MAMPs and therefore a lower detection by ELLecSA. In FIG. 16E, MAMPs from an amp-C mutant Enterobacter cloacae which hyperexpressed AMP-c was detected by ELLecSA using FcMBL coated beads and rhMBL-HRP. This strain was resistant to 100 ug/mL of both cefazolin (CF) and ceftazidime (CAZ) but susceptible to 100 ug/mL cefepime (FEP). Time course antibiotics were administered. Optimal MAMP detection occurred at 4 hours with 100 ug/mL cefepime.

Figure 17A:
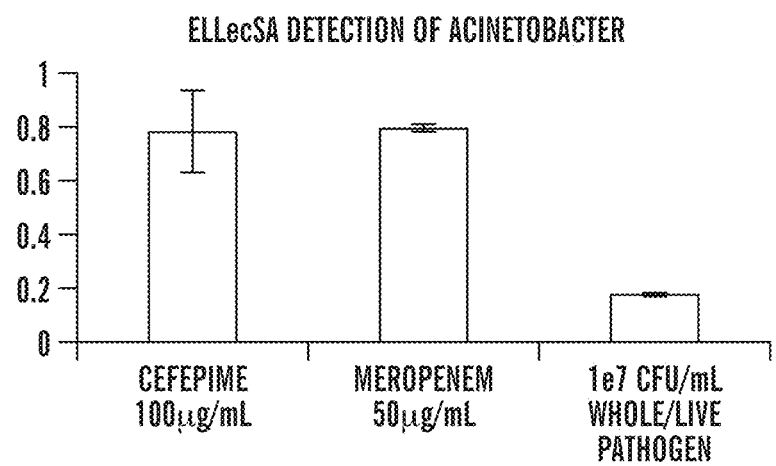
Figure 17B:
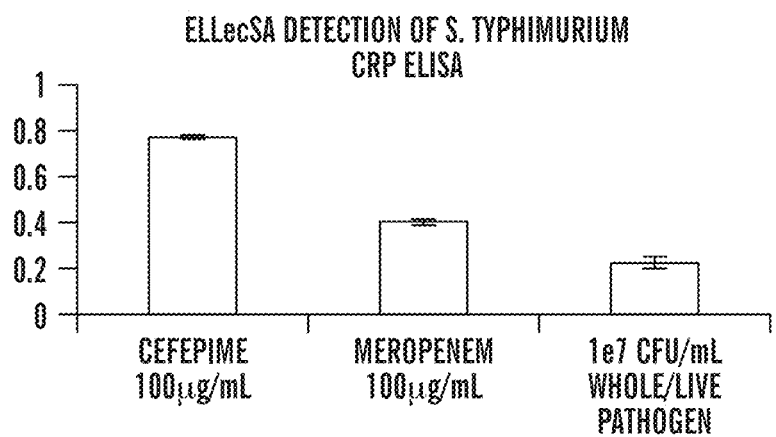
Figure 17C:
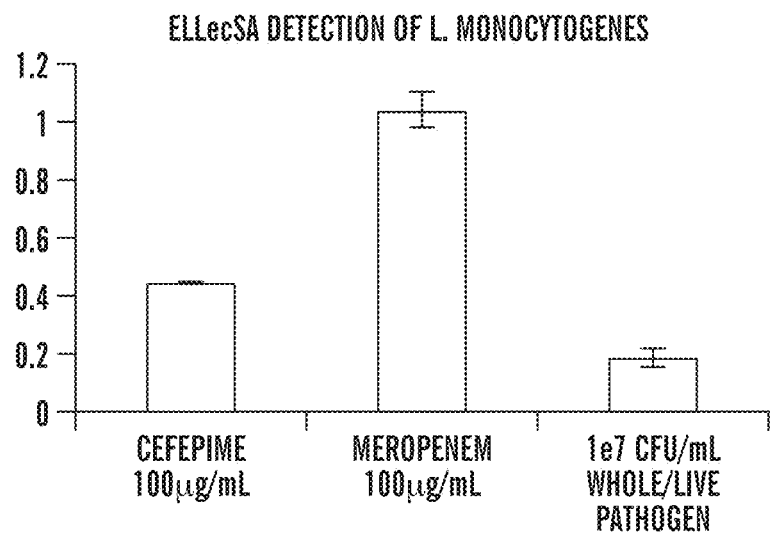
Figure 17D:
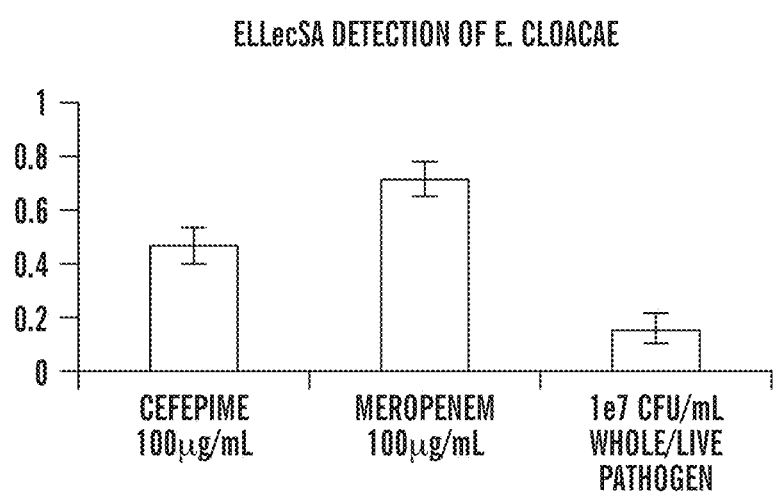

FIGS. 17A-17D show lysing microbes by antibiotic treatment to increase MAMPs for wild-type (wt) CRP-coated bead capture and ELLecSA detection. In FIG. 17A, CRP coated beads were used to detect the presence of MAMPs from a clinical isolate of Acinetobacter after 4 hour treatments of cefepime. Detection of MAMPs was done by ELLecSA using CRP-hrp. In FIG. 17B, CRP coated beads were used to detect the presence of MAMPs from a clinical isolate of Salmonella typhimurium after 4 hour treatment of cefepime and meropenem. Detection of MAMPs was done by ELLecSA using CRP-hrp. In FIG. 17C, CRP-coated beads were used to detect the presence of MAMPs from a clinical isolate of Listeria monocytogenes after 4 hour treatment of cefepime and meropenem. Detection of MAMPs was done by ELLecSA using CRP-hrp. In FIG. 17D, CRP-coated beads were used to detect the presence of MAMPs from a clinical isolate of Enterobacter cloacae after 4 hour treatment of cefepime and meropenem. Detection of MAMPs was done by ELLecSA using CRP-hrp.

Figure 18A:
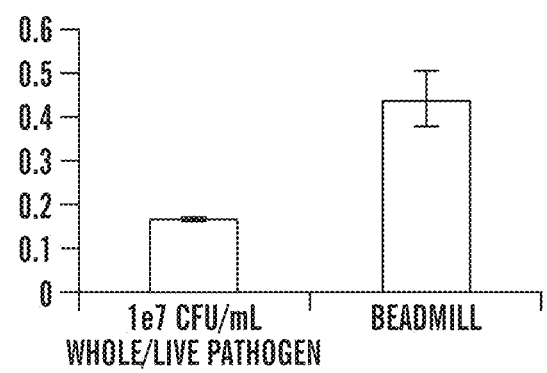
Figure 18B:
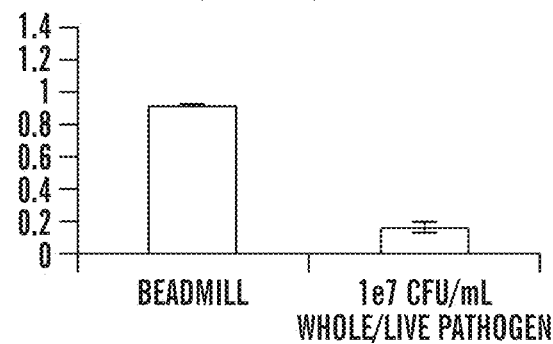

FIGS. 18A-18B show lysing microbes by mechanical treatment to increase MAMPs for FcMBL-coated bead capture and ELLecSA detection. In FIG. 18A, FcMBL coated beads were used to detect the presence of MAMPs from a clinical isolate of Klebsiella pneumoniae after 10 minute mechanical treatment using the beadmill. Detection of MAMPs was done by ELLecSA using rhMBL-hrp. In FIG. 18B, FcMBL coated beads were used to detect the presence of MAMPs from a clinical isolate of Salmonella typhimurium after a 10 minute mechanical treatment using the beadmill. Detection of MAMPs was done by ELLecSA using rhMBL-hrp.

Figure 19A:
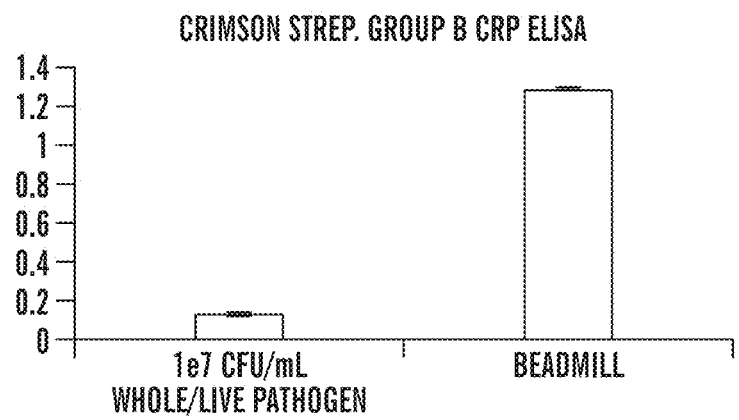
Figure 19B:
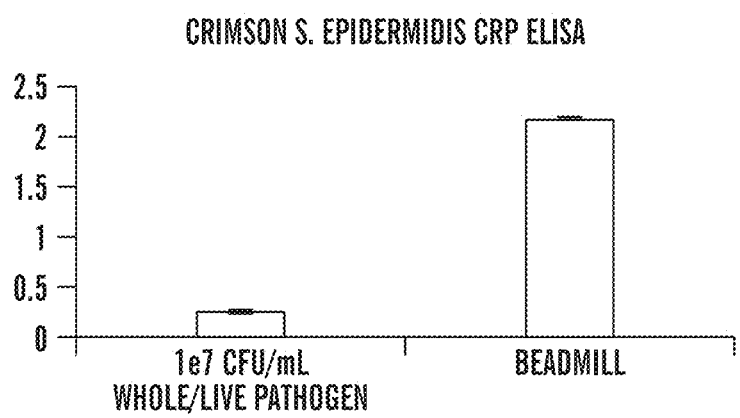
Figure 19C:
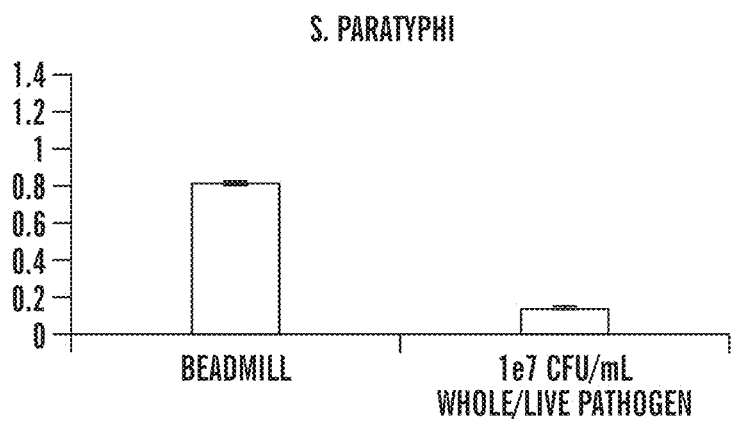

FIGS. 19A-19C show lysing microbes by mechanical treatment to increase MAMPs for CRP-coated bead capture and ELLecSA detection. In FIG. 19A, CRP coated beads were used to detect the presence of MAMPs from a clinical isolate of Strep. Group B after a 10 minute mechanical treatment using the beadmill. Detection of MAMPs was done by ELLecSA using CRP-hrp. In FIG. 19B, CRP coated beads were used to detect the presence of MAMPs from a clinical isolate of S. epidermidis after a 10 minute mechanical treatment using the beadmill. Detection of MAMPs was done by ELLecSA using CRP-hrp. In FIG. 19C, CRP coated beads were used to detect the presence of MAMPs from a clinical isolate of Salmonella paratyphi after a 10 minute mechanical treatment using the beadmill. Detection of MAMPs was done by ELLecSA using rhMBL-hrp.

Figure 20:
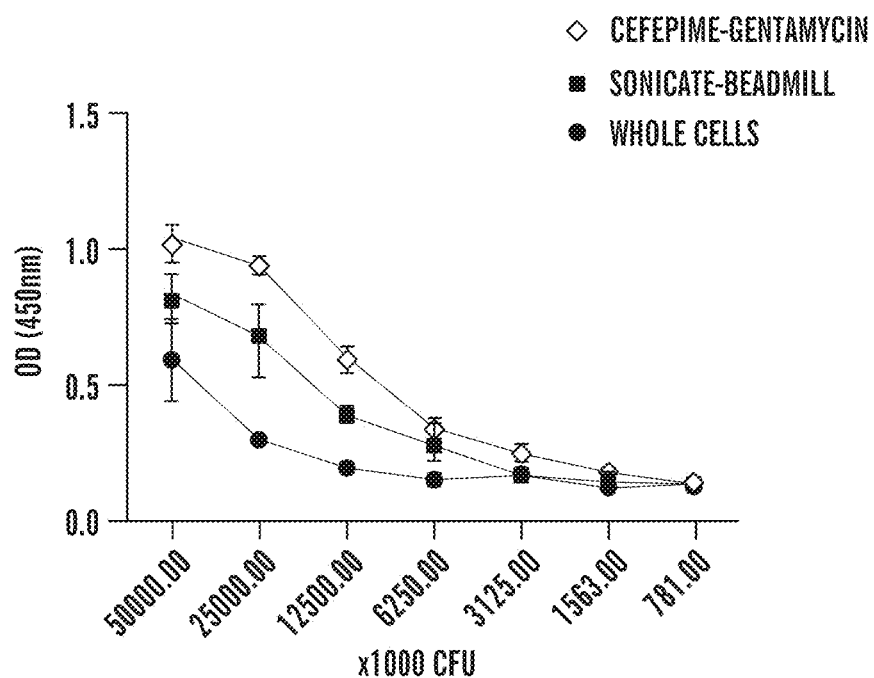

FIG. 20 shows ELLecSA detection of E. aerogenes in whole blood. Beadmill alters the surface of the cell wall by scraping off non-covalently bound capsular material loosely adsorbed to the surface. Antibiotics release MAMPs deeply embedded within the cell wall. By disrupting the covalent linkage of the cell wall and the peptidoglycan it releases determinants otherwise not exposed to microbe-binding molecules or pattern recognition receptors (PRRs) described herein. For example, heptose is a strong binder of MBL and a major constituent of LPS inner core. The inner core is deeply buried within the outer membrane of the gram negative bacteria and not accessible to PRRs until released by antibiotics and/or mechanical disruption.

Figure 21:
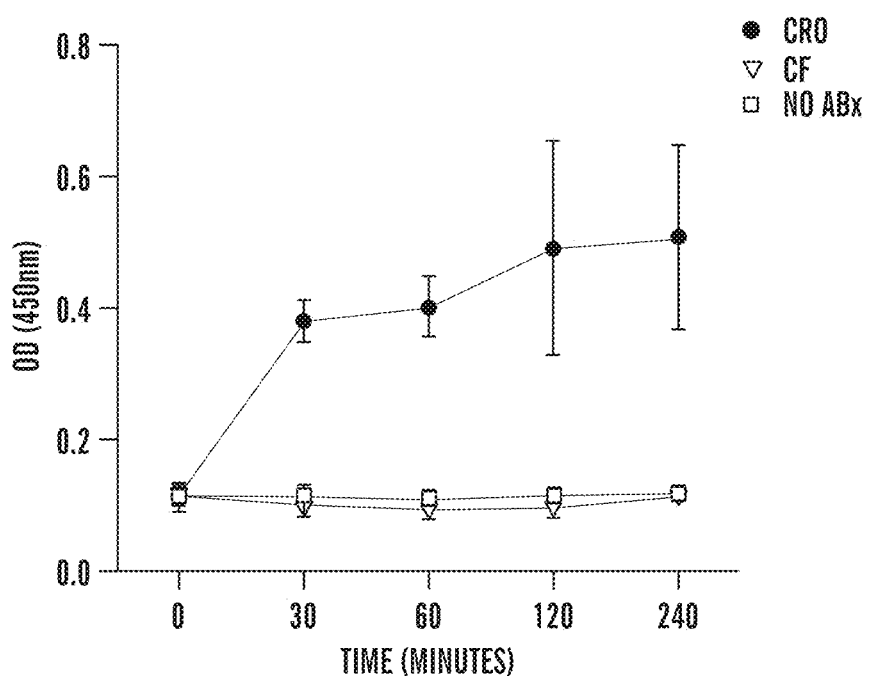

FIG. 21 shows in vitro data of ELLecSA detection of Enterobacter cloacae in the presence of active antibiotics. About 5e7 CFU of Enterobacter cloacae were incubated with active antimicrobial ceftriaxone (CRO), Cefalotin (CF) to which it is naturally resistant, or saline. MAMPs were released within 30 min after addition of the active antibiotic as detected by ELLecSA.

Figure 22A:
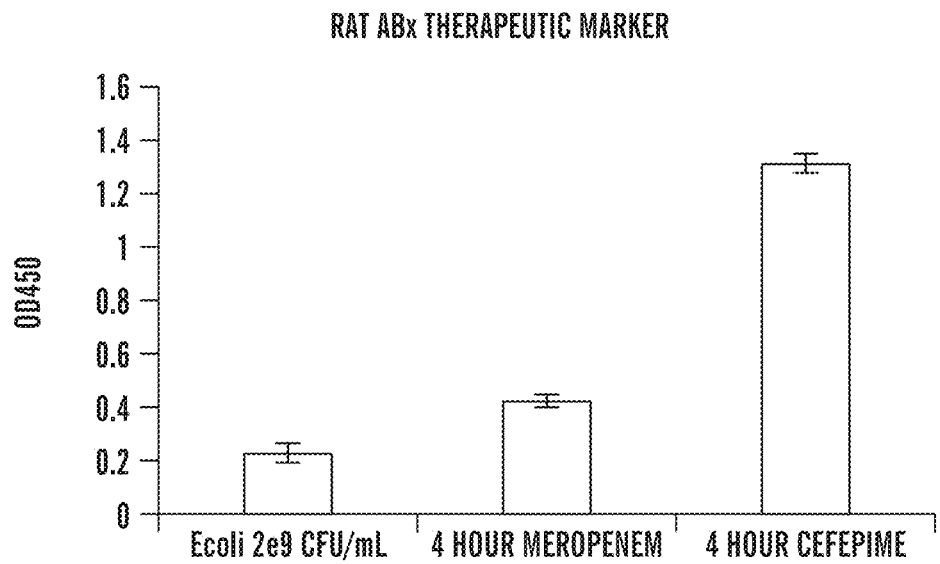
Figure 22B:
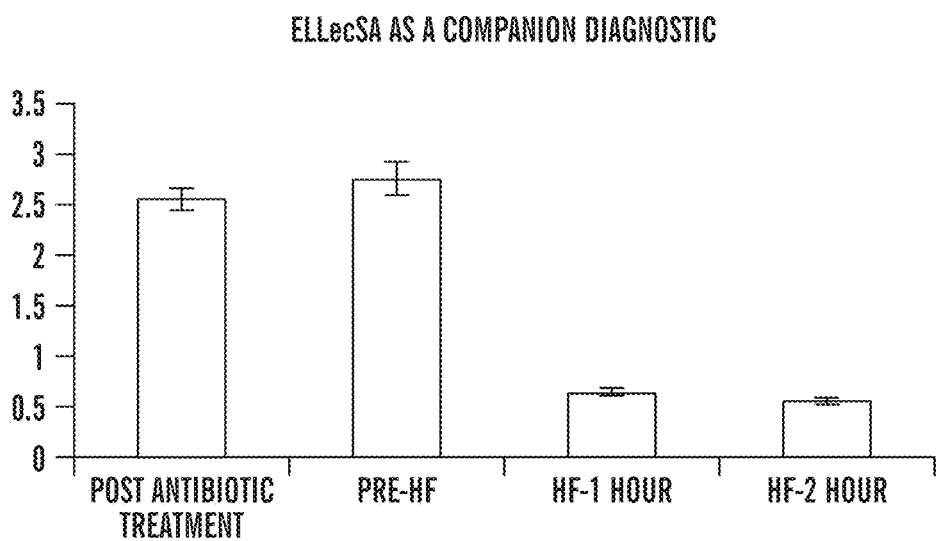

FIGS. 22A-22B show in vivo data for determining antibiotic efficacy. In FIG. 22A, six rats were infected with 2e9 CFU E. coli ATCC 8739 intraperitoneally. Infection proceeded for 4 hours before injection with cefepime at 100 ug/kg, meropenem at 100 ug/kg or saline (control). Animals were killed after 8 hours after infection and a terminal blood draw was performed. ELLecSA levels showed that meropenem (slow acting) generated a 2-fold increase over baseline (e.g., no antibiotic) whereas cefepime (fast acting) generated a six-fold increase over baseline (e.g., no antibiotic). Similar methods can be used to determine background microbial growth vs. antibiotic efficacy. In FIG. 22B, ELLecSA was used to detect the presence of MAMPs in vivo in Cefepime-treated rats with a $10^9$ CFU E. coli infection. Rats were anesthetized and their blood was run through an FcMBL coated blood cleansing device (BCD). Time points were collected at 4 hours post E. coli injection, 4 hours post cefepime injection, and 1 hour post FcMBL-coated blood cleansing device treatment.

Figure 23:
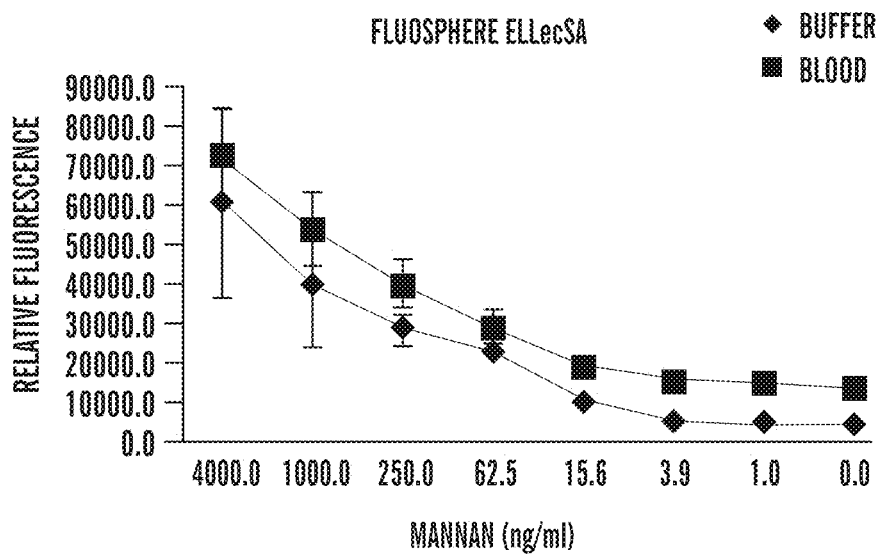

FIG. 23 shows an exemplary readout method for MAMP detection using ELLecSA, particularly, ELLecSA detection of mannan by fluorescence. Serial dilutions of mannan were incubated with FcMBL coated superparamagnetic beads. Mannan capture was determined by relative fluorescence using FcMBL coated yellow/green 0.04 uM streptavidin Fluospheres™ (Life Technologies) as per manufacturer's specifications.

Figure 24:
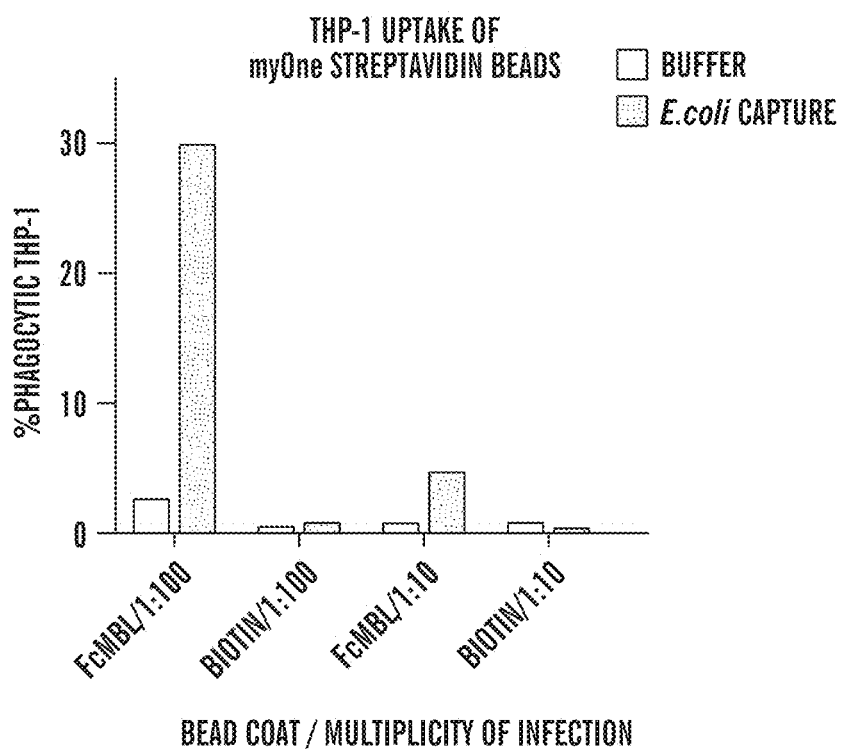

FIG. 24 shows that FcMBL beads coated in MAMPs can be phagocytized. FcMBL-coated beads incubated in MAMPs (e.g., E. coli) were phagocytized whereas biotin blocked beads and FcMBL beads alone were not phagocytized.

DETAILED DESCRIPTION OF THE INVENTION

As discussed herein, art known methods for detection of microbes in a sample generally seek to increase the number of living cells in the sample, for example by culturing the sample, before assaying for the presence of the microbes in the sample. In contrast, embodiments of the various aspects described herein are based on lysing and/or killing the cells in the sample to expose or release microbe-associated molecular patterns (MAMPs) before assaying for the presence of the microbes in the sample. Without wishing to be bound by a theory, the inventors' have discovered inter alia that detection of a microbe in a sample can be enhanced by lysing and/or killing the microbe before assaying with a pattern recognition receptor (PRR)-based assay (e.g., a lectin-based assay) for the presence or absence of microbes in the sample. By pre-treating a sample to lyse or kill microbes in a sample prior to a PRR-based assay (e.g., a lectin-based assay), the sensitivity of the PRR-based assay (e.g., a lectin-based assay) can be increased, which can allow for early diagnosis of a microbial infection and/or can also reduce false-negatives due to low concentration of microbes in a sample.

Without wishing to be bound by theory, some microbes can escape from detection by a PRR-based based assay (e.g., a lectin-based assay) via producing masking capsules or modifications of the exposed sugars (e.g., terminal sugars). The inventors have discovered that these microbes can be detected using a PRR-based assay (e.g., a lectin-based assay) by disrupting their architectural integrity with physical or chemical means to expose or dislodge microbe associated molecular patterns (MAMPS), prior to performing the PRR-based assay (e.g., a lectin based assay). In one example, the inventors were able to detect *Klebsiella oxytoca* isolates, which were otherwise undetectable as live or intact microbes by FcMBL Sandwich ELLecSA, by using an embodiment of the method disclosed herein. Thus, a simple pre-treatment of a sample to lyse or kill microbes therein can not only increase the sensitivity of a PRR-based assay (e.g., a lectin based assay), but can also unexpectedly expand the binding profile/spectrum of microbes that can be detected by a PRR-based assay (e.g., a lectin based assay).

Additionally, the inventors have also developed a method to screen for antimicrobial agents and/or monitor antimicrobial activity of a treatment in a subject in need thereof, based on a significant increase in detection signals from or derived from MAMPs released by lysed microbes. Thus, the methods described herein do not rely on detecting the biological response or the number of intact or viable microbes remained in the sample after the treatment. For example, the inventors have shown that detecting a significant increase in MAMPs due to lysis of microbes by an effective antibiotic within a specified time frame is far more sensitive than detecting a reduced number of intact microbes (e.g., even by a three order of magnitude difference).

Accordingly, embodiments of various aspects described herein provide more sensitive assays and methods for detection of microbes and/or microbial matter, e.g., MAMPs. Not only can the assays and methods described herein be used for early diagnosis of an infection, and/or diagnosis of infection caused by encapsulated pathogens that would be generally escape from detection by a pattern recognition receptor (PRR)-based assay (e.g., but not limited to a lectin-based assay), they can also be used for determining antimicrobial efficacy to identify a novel antimicrobial agent or composition, or for monitoring the efficacy of an antimicrobial treatment administered to a subject.

Methods for Enhancing or Increasing Microbial Detection by a Pattern Recognition Receptor (PRR)-Based Assay Described Herein In one aspect, provided herein relates to a method of enhancing or increasing microbial detection by a pattern recognition receptor (PRR)-based assay. Generally, the method comprises pre-treating a sample to expose, release and/or generate microbe associated molecular patterns (MAMPs) from at least a portion of microbes in the sample. The pre-treated sample can then be subjected to a PRR-based assay, which is described in detail in the section "Pattern recognition receptor (PRR)-based assay (e.g., a lectin based assay)" below. In some embodiments, the method can further comprise detecting the presence or absence of MAMPs with a PRR-based based assay. The exposure, release and/or generation of MAMPs can amplify signals from a PRR-based assay, thus enhancing or increasing microbial detection by PRR-based assay.

As used herein and throughout the specification, the term "microbe associated molecular patterns" or "MAMPs" refers to molecules, components or motifs associated with or secreted or released by microbes or groups of microbes (whole and/or lysed and/or disrupted) that are generally recognized by corresponding pattern recognition receptors (PRRs). In some embodiments, the MAMPs can also encompass molecules associated with cell components released during cell damage or lysis. Examples of MAMPs include, but are not limited to, microbial carbohydrates (e.g., lipopolysaccharide or LPS, mannose), endotoxins, microbial nucleic acids (e.g., bacterial or viral DNA or RNA), microbial peptides (e.g., flagellin), peptidoglycans, lipoteichoic acids, N-formylmethionine, lipoproteins, lipids, phospholipids or their precursors (e.g., phosphochloline), and fungal glucans.

In some embodiments, MAMPs include carbohydrate recognition domain (CRD)-binding motifs. As used herein, the term "carbohydrate recognition domain (CRD)-binding motifs" refers to molecules or motifs that bind to a molecule or composition comprising a CRD. As used herein, the term "carbohydrate recognition domain" or "CRD" refers to one or more regions, at least a portion of which, can bind to carbohydrates on a surface of microbes or pathogens. In some embodiments, the CRD can be derived from a lectin described herein. In some embodiments, the CRD can be derived from a mannan-binding lectin (MBL). Accordingly, in some embodiments, MAMPs are molecules, components or motifs associated with microbes or groups of microbes that are recognized by lectin-based PRRs described herein. In one embodiment, MAMPs are molecules, components, or motifs associated with microbes or groups of microbes that are recognized by mannan-binding lectin (MBL).

In some embodiments, MAMPs are molecules, components or motifs associated with microbes or groups of microbes that are recognized by a C-reactive protein (CRP)-based PRR.

As used herein and throughout the specification, the term "pattern recognition receptors" or "PRRs" refer to microbe-binding domains, molecules, proteins or peptides that bind to at least one or more (including, at least two, at least three, at least four, at least five, or more) MAMPs described herein. In some embodiments, a PRR can be a naturally occurring or synthetic molecule. In some embodiments, a PRR can be a recombinant molecule. In some embodiments, a PRR can be a fusion protein. For example, PRR can also be fusion protein comprising at least a part of a lectin and at least a part of a second protein or peptide, e.g., but not limited to an Fc portion of an immunoglobulin or another microbe-binding molecule. An exemplary lectin can be mannan binding lectin (MBL) or other mannan binding molecules. Non-limiting examples of PRR include at least a microbe-binding domain selected from lectins (e.g., C-type lectins such as mannan binding lectin (MBL)), toll-like receptors, NODs, complement receptors, collectins, ficolins, pentraxins such as serum amyloid and C-reactive protein, lipid transferases, peptidoglycan recognition proteins (PGRs), and any combinations thereof. In some embodiments, PRRs can be microbe-binding molecules described in the International Patent Application No. WO 2013/012924, the content of which is incorporated by reference in its entirety.

The MAMPs can be exposed, released or generated from microbes in a sample by various sample pretreatment methods. In some embodiments, the MAMPs can be exposed, released or generated by lysing or killing at least a portion of the microbes in the sample. Without limitations, any means known or available to the practitioner for lysing or killing microbe cells can be used. Exemplary methods for lysing or killing the cells include, but are not limited to, physical, mechanical, chemical, radiation, biological, and the like. Accordingly, pre-treatment for lysing and/or killing the microbe cells can include application of one or more of ultrasound waves, vortexing, centrifugation, vibration, magnetic field, radiation (e.g., light, UV, Vis, IR, X-ray, and the like), change in temperature, flash-freezing, change in ionic strength, change in pH, incubation with chemicals (e.g. antimicrobial agents), enzymatic degradation, and the like.

In some embodiments, the pre-treatment for lysing and/or killing the microbe cells can comprise subjecting the sample to sonication or ultrasound waves.

In some embodiments, the pre-treatment can comprise lysing cells by mechanical means. For example, the sample can be subjected to homogenization, agitation, shaking, vortexing, centrifugation, milling (including beadmilling, grinding, french press, cryofracture, and the like) and the like. In one embodiment, the pre-treatment can comprise subjecting the sample to homogenization with a beadmill.

Inventors discovered that, in some embodiments, treating microbes in a sample for about 1 to 4 hours with a broad spectrum antibiotic (e.g., beta-lactam targeting PBP3) can cause the microbes to shed large amounts of LPS, transferring the active fraction to the supernatant. Accordingly, in some embodiments, the pre-treatment can comprise incubating the sample with at least one or more antimicrobial agents. In some embodiments, a combination of two or more antimicrobial agents (including, e.g., two, three, four, or more antimicrobial agents) can be used.

As used herein, the term "antimicrobial agent" refers to a molecule or composition which destroys microbes (i.e., bacteria, fungi, viruses, parasites and microbial spores) or prevents or inhibits their development, proliferation and/or pathogenic action. Exemplary antimicrobial agents include, but are not limited to, small organic or inorganic molecules; peptides; proteins; peptide analogs and derivatives; peptidomimetics; antibodies (polyclonal or monoclonal); antigen binding fragments of antibodies; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the antimicrobial agent can be selected from aminoglycosides, ansamycins, beta-lactams, bis-biguanides, carbacephems, carbapenems, cationic polypeptides, cephalosporins, fluoroquinolones, glycopeptides, iron-sequestering glycoproteins, linosamides, lipopeptides, macrolides, monobactams, nitrofurans, oxazolidinones, oxazolidonones, penicillins, polypeptides, quaternary ammonium compounds, quinolones, silver compounds, sulfonamides, tetracyclines, and any combinations thereof. In some embodiments, the antimicrobial agent can comprise an antibiotic.

Some exemplary specific antimicrobial agents include broads senicillins amoxicillin (e.g., Ampicillin, Bacampicillin, Carbenicillin Indanyl, Mezlocillin, Piperacillin, Ticarcillin), Penicillins and Beta Lactamase Inhibitors (e.g., Amoxicillin-Clavulanic Acid, Ampicillin-Sulbactam, Benzylpenicillin, Cloxacillin, Dicloxacillin, Methicillin, Oxacillin, Penicillin G, Penicillin V, Piperacillin Tazobactam, Ticarcillin Clavulanic Acid, Nafcillin), Cephalosporins (e.g., Cephalosporin I Generation, Cefadroxil, Cefazolin, Cephalexin, Cephalothin, Cephapirin, Cephradine), Cephalosporin II Generation (e.g., Cefaclor, Cefamandol, Cefonicid, Cefotetan, Cefoxitin, Cefprozil, Ceftmetazole, Cefuroxime, Loracarbef), Cephalosporin III Generation (e.g., Cefdinir, Ceftibuten, Cefoperazone, Cefixime, Cefotaxime, Cefpodoxime proxetil, Ceftazidime, Ceftizoxime, Ceftriaxone), Cephalosporin IV Generation (e.g., Cefepime), Macrolides and Lincosamines (e.g., Azithromycin, Clarithromycin, Clindamycin, Dirithromycin, Erythromycin, Lincomycin, Troleandomycin), Quinolones and Fluoroquinolones (e.g., Cinoxacin, Ciprofloxacin, Enoxacin, Gatifloxacin, Grepafloxacin, Levofloxacin, Lomefloxacin, Moxifloxacin, Nalidixic acid, Norfloxacin, Ofloxacin, Sparfloxacin, Trovafloxacin, Oxolinic acid, Gemifloxacin, Perfloxacin), Carbepenems (e.g., Imipenem-Cilastatin, Meropenem), Monobactams (e.g., Aztreonam), Aminoglycosides (e.g., Amikacin, Gentamicin, Kanamycin, Neomycin, Netilmicin, Streptomycin, Tobramycin, Paromomycin), Glycopeptides (e.g., Teicoplanin, Vancomycin), Tetracyclines (e.g., Demeclocycline, Doxycycline, Methacycline, Minocycline, Oxytetracycline, Tetracycline, Chlortetracycline), Sulfonamides (e.g., Mafenide, Silver Sulfadiazine, Sulfacetamide, Sulfadiazine, Sulfamethoxazole, Sulfasalazine, Sulfisoxazole, Trimethoprim-Sulfamethoxazole, Sulfamethizole), Rifampin (e.g., Rifabutin, Rifampin, Rifapentine), Oxazolidonones (e.g., Linezolid, Streptogramins, Quinopristin Dalfopristin), Bacitracin, Chloramphenicol, Fosfomycin, Isoniazid, Methenamine, Metronidazol, Mupirocin, Nitrofurantoin, Nitrofurazone, Novobiocin, Polymyxin, Spectinomycin, Trimethoprim, Colistin, Cycloserine, Capreomycin, Ethionamide, Pyrazinamide, Para-aminosalicyclic acid, Erythromycin ethylsuccinate, and the like.

Without limitations, incubation of microbes present in the sample with one or more antimicrobial agents can be at any desired temperature and for any desired duration. In some embodiments, the incubation can be performed at room temperature or at an elevated temperature. In some embodiments, incubation can be performed at a temperature of about 30° C. to about 45° C. In one embodiment, incubation can be performed at a temperature of about 37° C.

As indicated above, incubation of microbes present in a sample can be performed for any desired time period, which can vary with a number of factors, including but not limited to, temperature of incubation, concentration of microbes in the sample, and/or potency and/or concentrations of antimicrobial agents used. In some embodiments, incubation can be for about at least one minute (e.g. one, five, ten, fifteen, twenty, twenty-five, thirty, thirty-five, forty, forty-five, fifty-five, sixty, ninety minutes or more). In some embodiments, incubation can be for at least about one hour, at least about two hours, at least about three hours, at least about four hours, at least about five hours, at least about six hours, at least about seven hours, at least about eight hours, at least about nine hours, at least about ten hours or more. In some embodiments, incubation can be for a period of about fifteen minutes to about ninety minutes. In one embodiment, incubation can be for a period of about thirty minutes to about sixty minutes. In another embodiment, incubation can be for a period of about thirty minutes to about twenty-four hours. In one embodiment, incubation can be for a period of at least about four hours.

Amount of one or more antimicrobial agent added to a sample can be any desired amount and vary with a number of factors, including but not limited to, types of microbes in the sample, and/or potency of antimicrobial agents used. For example, one or more antimicrobial agents added to sample can have a concentration ranging from nanomolars to millimolars. In some embodiments, one or more antimicrobial agents added to a sample can have a concentration ranging from 0.01 nM to about 100 mM, from about 0.01 nM to about 10 mM, or from about 0.1 nM to about 1 mM.

In some embodiments, one or more antimicrobial agents added to a sample can have a concentration ranging from nanograms per milliliters to micrograms per milliliters. In some embodiments, one or more antimicrobial agents added to a sample can have a concentration ranging from about 1 ng/mL to about 1000 µg/mL, from about 10 ng/mL to about 750 µg/mL, or from about 100 ng/mL to about 500 µg/mL. In some embodiments, one or more antimicrobial agents added to a sample can have a concentration ranging from about 10 µg/mL to about 500 µg/mL or from about 100 µg/mL to about 500 µg/mL.

In some embodiments, the pre-treatment can comprise incubating the sample with at least one or more degradative enzymes. For example, in some embodiments, a degradative enzyme can be selected to cleave at least some of the cell wall carbohydrates, thus restoring detection of carbohydrates that are otherwise not recognized by PRRs. In some embodiments, a degradative enzyme can be selected to cause call wall degradation and thus release or expose MAMPs that are otherwise unable bind to the PRRs. Other examples of degradative enzymes include, but are not limited to, proteases, lipases such as phospholipases, neuraminidase, and/or sialidase, or any other enzyme modifying the presentation of any MAMP to any PRR leveraged for detection of the MAMP. For instance, an exemplary PRR can comprise MBL or recombinant human MBL or engineered FcMBL, which binds mannose containing carbohydrates such as the core of LPS, the Wall Teichoic Acid from *Staphylococcus aureus*, PIM6 or Mannose-capped LipoAraboMannan from *M. tuberculosis* whereas CRP binds phosphocholine found in *Streptococcus pneumonia* (Brundish and Baddiley, "Pneumococcal C-substance, a ribitol teichoic acid containing choline phosphate" Biochem J. 1968 December, 110(3): 573-82), *Haemophilus influenzae* (Weiser et al., Decoration of lipopolysaccharide with phosphorylcholine: a phase-variable characteristic of *Haemophilus influenzae*" Infect Immun. 1997 March; 65(3): 943-950), *Pseudomonas aeruginosa, Neisseria meningitides, Neisseria gonorrhoeae* (Serino and Virji, "Phosphorylcholine decoration of lipopolysaccharide differentiates commensal Neisseriae from pathogenic strains: identification of licA-type genes in commensal Neisseriae" Mol Microbiol. 2000 March, 35(6): 1550-9), *Morganella morganii* (Potter, "Antigen-binding myeloma proteins in mice" Ann N Y Acad Sci. 1971 Dec. 31, 190: 306-21), and *Aspergillus fumigatus* (Volanakis, "Human C-reactive protein: expression, structure, and function, "Molecular Immunology," 2001, 38(2-3): 189-197). Other PRR can be equally leveraged to recognize MAMPs such as NODs or PGRP.

The methods described herein can also be used for detecting microbes that can generally escape detection with PRR-based assays. Without wishing to be bound by theory, some microbes can escape detection by PRRs by masking their MAMPs with a capsule decorated with carbohydrates (e.g., expressed by eukaryotic cells) that are not generally recognized by PRRs. Therefore, these microbes can be easily missed by PRR-based assays during diagnosis. Surprisingly, the inventors have discovered that by disrupting the architectural integrity (e.g., outer layers of the cell wall) and/or fragmenting of these microbes to expose the hidden MAMPs that are not normally presented to the PRRs when the microbes are intact and live, these disrupted microbes and the exposed MAMPs can then be detected using the PRR-based assay (e.g., a lectin based assay). For example, the inventors were able to detect *Klebsiella oxytoca* isolates, *Salmonella typhimurium* isolates, *Acinetobacter* isolates, and *Listeria monocytogenes* isolates, which were otherwise undetectable as live or intact pathogens by FcMBL Sandwich ELLecSA, by using some embodiment of the assays or methods described herein. Thus, provided herein is also a method of detecting microbes which are undetectable as live or intact microbes by a PRR-based assay described herein. The sample suspected of having a microbe can be pretreated to expose, release or generate MAMPs from the suspected microbe prior to assaying for the microbes or components, MAMPs, or secretions thereof. In some embodiments, the suspected microbe can be lysed or killed by any art known methods or any methods described herein to expose, release or generate MAMPs. Accordingly, a method of expanding the microbial detection spectrum of a PRR-based assay by pretreating a sample to lyse or kill microbes present in a sample prior to subjecting the sample to a PRR-based assay for the presence or absence of microbes in the sample. As used herein, the term "microbial detection spectrum" refers to the number of microbe species and/or groups of microbes that can be captured and/or detected by an assay.

In some embodiments, by comparing the binding profile from a PRR-based assay with a pre-treatment step, relative to the binding profile from the PRR-based assay without the pre-treatment step, identification of the class of microbes (e.g., encapsulated microbes vs. "bare" or "noncapsulated" microbes, i.e., microbes without a capsule masking MAMPs) can be determined. Accordingly, a method for identifying encapsulated microbes in a sample is also provided herein. The method comprises (a) subjecting a sample to a pre-treatment as described herein; (b) assaying the pre-treated sample with a PRR-based assay for the presence or absence of microbes and/or MAMPs; (c) comparing the binding profile obtained from the PRR-based assay with a control sample that was assayed with a PRR-based assay without the pre-treatment; and (d) identifying the sample as containing encapsulated microbes, if MAMPs is detected by the PRR-based assay with the pre-treatment step, but not without the pre-treatment step.

In some embodiments of various aspects described herein, the PRR-based assay can comprise a lectin-based assay, which is described in detail in the section "Pattern recognition receptor (PRR)-based assay (e.g., a lectin based assay)" below.

Methods for Determining Antimicrobial Activity or Efficacy and Exemplary Applications Thereof As disclosed herein, the inventors have made the unexpected and surprising discovery of enhancing detection of microbes in a sample by physical or chemical disruption of the microbes in a sample before subjecting the sample to a PRR-based assay (e.g., a lectin-based assay). The inventors have further discovered in vivo applications of this unexpected, surprising discovery for use in methods and compositions for monitoring clinical efficacy of an antimicrobial regimen by measuring the destruction of microbes, a parameter that has eluded physicians since the first use of antimicrobial agents.

The in vivo release of MAMPs in the course of an infection generates a detectable ELLecSA signal in the bloodstream in the absence of circulating live pathogens. Without wishing to be bound by theory, the microbial metabolism and/or the immune response of the host is responsible for the release of MAMPs in the bloodstream from a remote location, thereby causing the symptoms associated with sepsis and the general response to the infection. The exacerbation of clinical signs of infection following the initiation of antimicrobial treatment or the restoration of the immune system in acquired immunodeficiency syndrome is known.

For example, endotoxin or lipopolysaccharide (LPS) is one of the outer membrane carbohydrates of Gram-negative bacteria that can replicate septic shock when experimentally administered to mammals including humans, and is believed to be a major actor in Gram-negative sepsis. The existing assays used to quantify LPS are the Limulus Amoebocyte Lysis (LAL) that has long been disproved as a plasmatic biomarker, and the Endotoxin Activity Assay test (EAA) that was developed to detect endotoxin in blood but is lacking in specificity and is not effective in neutropenic patients and is not automated.

In contrast, ELLecSA as described herein is capable of detecting such a release of MAMPs (e.g., LPS) following the initiation of antimicrobial therapy. It can be applied in vitro in susceptibility assays as a surrogate for bactericidal activity in microbes releasing MAMPs recognized by the chosen PRR coated surface or in vivo to test the efficacy of antibiotic treatment as a measurement of the systemic effect of the therapy, integrating microbiological susceptibility data and pharmacokinetic/pharmacodynamics (PK/PD) parameters for a true assay of overall efficacy and potency of a regimen. In some embodiments, the ELLecSA comprises use of at least one broad spectrum microbial binding molecule (e.g., FcMBL) engineered from a soluble Pattern Recognition Receptor (sPRR) human Mannose Binding Lectin (MBL). FcMBL was found to be capable of binding microbes and microbial products such as MAMPs in biological fluids including blood and plasma.

Without wishing to be bound by a theory, the serial determinations of FcMBL therapy provides a novel tool to establish the biological efficacy of an antimicrobial regimen in patients by measuring the release of microbial carbohydrates upon active therapy. Patients with an infection diagnosed without antibacterial susceptibility documentation (serological diagnosis, PCR diagnosis, previous antibiotic treatment) are numerous and the confirmation of the therapeutic activity of the probabilistic regimen is difficult to obtain. The disclosure provides a method for ascertaining the clinical activity of the antibiotic by providing previously unavailable data for such use.

Accordingly, in one aspect, the disclosure provides a method of determining efficacy of an antimicrobial treatment regimen in a subject. The method comprises providing a biological sample from a subject administered an antimicrobial treatment or undergoing an antimicrobial treatment regimen. The sample from the subject is assayed by a PRR-based assay. A treatment related change (e.g., increase, decrease, or spike) in a detectable signal level relative to a baseline level in the assay indicates that the antimicrobial regimen is effective. Thus, in some embodiments, the method can further comprise (a) determining the antimicrobial treatment to be effective if a treatment related change (e.g., increase, decrease, or spike) in a detectable signal level relative to a baseline level is detected by the PPR-based assay; or (b) determining the antimicrobial treatment to be ineffective if the treatment related change (e.g., increase, decrease, or spike) in a detectable signal level relative to the baseline level is insignificant or absent. When the antimicrobial treatment is determined to be ineffective, the subject can be administered a different antimicrobial treatment regimen and the efficacy of the new treatment can be determined by repeating the method described herein.

Without wishing to be bound by theory, the innate immune response can appear as an infection baseline. As used herein, the term "infection baseline" refers to level of MAMP signal detected by a PRR based assay described herein in a sample determined to be infected with at least one or microbes. In some embodiments, the infection baseline can also encompass a subject's innate immune response to the infection, depending on when the subject's sample is taken over the course of infection. After administration of an antimicrobial treatment, the level of MAMP signal can be changed relative to the baseline. The direction of the change can depend on, e.g., severity of infection when an antimicrobial treatment is initiated, nature of microbes and/or mode of action of antimicrobial treatment. Accordingly, the methods described herein can provide real-time measurement or monitoring of an antimicrobial treatment effect on a subject.

In some embodiments, an antimicrobial treatment is determined to be effective if there is a treatment related increase, or spike in a detectable signal level by at least about 30% or more (including, at least about 40%, at least about 50%, at least about 60%, at least about 70%, at least about 80%, at least about 90%, at least about 95% or more), relative to a baseline level in a PRR-based assay. In some embodiments, an antimicrobial treatment is determined to be effective if there is a treatment related increase or spike in a detectable signal level by at least about 1.1-fold or more (including, at least about 1.5-fold, at least about 2-fold, at least about 3-fold, at least about 4-fold, at least about 5-fold, at least about 6-fold, or more), relative to a baseline level in a PRR-based assay.

In some embodiments, an antimicrobial treatment is determined to be ineffective if a treatment related increase spike in a detectable signal level is less than 30% or lower (including, less than 25%, less than 20%, less than 15%, less than 10%, less than 5%, less than 3%, less than 1% or lower) relative to a baseline level in a PRR-based assay.

In some embodiments, an antimicrobial treatment is determined to be effective if there is a treatment related decrease in a detectable signal level by at least about 10%, at least about 20%, at least about 30% or more (including, at least about 40%, at least about 50%, at least about 60%, at least about 70%, at least about 80%, at least about 90%, at least about 95% or more), relative to a baseline level in a PRR-based assay.

In some embodiments, an antimicrobial treatment is determined to be ineffective if a treatment related decrease in a detectable signal level is less than 30% or lower (including, less than 25%, less than 20%, less than 15%, less than 10%, less than 5%, less than 3%, less than 1% or lower) relative to a baseline level in a PRR-based assay.

As used herein and throughout the specification, the term "antimicrobial treatment" refers to administering to a subject in need thereof a therapeutic composition comprising an antimicrobial agent described herein.

Based on the current clinical practices, some infections can be documented by a "therapeutical trial" when an infection is suspected without microbiological documentation. Generally, the therapeutical trial comprises testing the hypothesis of the bacterial etiology of a clinical disorder by providing antibiotics and monitoring the clinical improvement of the patient under the treatment. A clinical improvement indicates a diagnosis of infection. In the absence of improvement over the duration of the "trial", the treatment is changed to encompass different pathogens or the infectious etiology is ruled out.

Without wishing to be bound by a theory, inventors' unexpected, surprising discovery disclosed herein can be used for providing objective metrics for the "therapeutical trial" success or failure. Accordingly, in one aspect, the disclosure provides a method for diagnosing an infection in a subject. Generally, the method comprises providing a biological sample from a subject administered an antimicrobial treatment or undergoing an antimicrobial treatment regimen. The sample from the subject is assayed by a PRR-based assay. A treatment related change (e.g., increase, decrease, or spike) in a detectable signal level relative to a baseline level in the assay indicates infection with a microbe susceptible to the antimicrobial treatment. Thus, in some embodiments, the method can further comprise (a) identifying the microbe species or genus that is susceptible to the administered antimicrobial treatment if the PRR-based assay yields a treatment related change (e.g., increase, decrease, or spike) in a detectable signal level relative to a baseline level in the assay; or (b) performing additional assay and/or administering to the subject with a different antimicrobial treatment if a treatment related change (e.g., increase, decrease, or spike) in a detectable signal level relative to the baseline level is insignificant or absent. The early detection of the antimicrobial treatment regimen activity can allow for a faster evaluation of the trial success and faster explorations of microbial etiologies: bacterial, fungal, or mycobacterial.

In some embodiments, the subject is diagnosed with an infection (e.g., with microbes that are susceptible to the antimicrobial treatment) if there is a treatment related change (e.g., increase, decrease, or spike) in a detectable signal level by at least about 30% or more (including, at least about 40%, at least about 50%, at least about 60%, at least about 70%, at least about 80%, at least about 90%, at least about 95% or more), relative to a baseline level in a PRR-based assay. In some embodiments, the subject is diagnosed with an infection (e.g., with microbes that are susceptible to the antimicrobial treatment) if there is a treatment related increase or spike in a detectable signal level by at least about 1.1-fold or more (including, at least about 1.5-fold, at least about 2-fold, at least about 3-fold, at least about 4-fold, at least about 5-fold, at least about 6-fold, or more), relative to a baseline level in a PRR-based assay.

In some embodiments, if a treatment related change (e.g., increase, decrease, or spike) in a detectable signal level is less than 30% or lower (including, less than 25%, less than 20%, less than 15%, less than 10%, less than 5%, less than 3%, less than 1% or lower) relative to a baseline level in a PRR-based assay, the subject suspected of having an infection can be administered a different antimicrobial treatment.

The inventors' discovery can also be used for adapting, optimizing or selecting an antimicrobial treatment regimen in the absence of antimicrobial susceptibility testing. For example, following successful trial of a broad spectrum antimicrobial agent, iterations with narrow spectrum antimicrobial agents can be used for optimizing the treatment of the unknown infection agent.

Accordingly, in one aspect, the disclosure provides a method of adapting or optimizing an antimicrobial treatment regimen in a subject in need thereof. Generally, the method comprises providing a biological sample from a subject who is administered a broad spectrum antimicrobial treatment/agent or undergoing a broad spectrum antimicrobial treatment regimen. The sample from the subject is assayed by a PRR-based assay. If a treatment related change (e.g., increase, decrease, or spike) in a detectable signal level relative to a baseline level in the assay is seen, the subject can be administered a narrow spectrum antimicrobial agent/treatment. A sample obtained after onset of the narrow spectrum antimicrobial treatment regime can be assayed by a PRR-based assay. Absence of a change (e.g., increase, decrease, or spike) in a detectable signal level relative to a baseline level in the assay indicates that the narrow spectrum antimicrobial agent/treatment is ineffective. If the treatment is ineffective, the subject can be administered a different narrow spectrum antimicrobial agent/treatment and sample obtained after onset of the different narrow spectrum antimicrobial treatment regimen can be assayed by a PRR-based assay. Administering of different narrow spectrum antimicrobial agent/treatment and assaying of samples by a PRR-based assay can be repeated until the assay shows a change (e.g., increase, decrease, or spike) in a detectable signal level relative to a baseline level, indicating that the narrow or different spectrum antimicrobial agent/treatment is effective.

In some embodiments, a narrow or different spectrum antimicrobial treatment is determined to be effective if a treatment related change (e.g., increase, decrease, or spike) in a detectable signal level is by at least about 30% or more (including, at least about 40%, at least about 50%, at least about 60%, at least about 70%, at least about 80%, at least about 90%, at least about 95% or more), relative to a baseline level in a PRR-based assay. In some embodiments, a narrow spectrum antimicrobial treatment is determined to be effective if a treatment related increase or spike in a detectable signal level is by at least about 1.1-fold or more (including, at least about 1.5-fold, at least about 2-fold, at least about 3-fold, at least about 4-fold, at least about 5-fold, at least about 6-fold, or more), relative to a baseline level in a PRR-based assay.

In some embodiments, a narrow spectrum antimicrobial treatment is determined to be ineffective if a treatment related change (e.g., increase, decrease, or spike) in a detectable signal level is less than 30% or lower (including, less than 25%, less than 20%, less than 15%, less than 10%, less than 5%, less than 3%, less than 1% or lower) relative to a baseline level in a PRR-based assay.

The inventors' discovery can also be used for optimizing an antimicrobial regimen. In many cases, the clinical improvement following the implementation of an antimicrobial regimen does not meet expectations. There are currently no methods other than measuring serum level adequacy to document the treatment. This procedure in no way reflects the true activity of the agent at the site of infection. Using the methods disclosed herein allows determination of true efficacy, and allows the evaluation of combination therapy, posology or administrations schemes.

Accordingly, in another aspect, provided herein is a method of optimizing an antimicrobial treatment regimen in a subject in need thereof. Generally, the method comprises providing a biological sample from a subject who is administered a first antimicrobial treatment regimen or undergoing a first antimicrobial treatment regimen. The sample from the subject is assayed by a PRR-based assay. If a treatment related change (e.g., increase, decrease, or spike) in a detectable signal level relative to a baseline level in the assay is seen, the first antimicrobial treatment regimen is effective. On the other hand, absence of a change (e.g., increase, decrease, or spike) in a detectable signal level relative to a baseline level in the assay indicates that the first antimicrobial treatment regimen is ineffective. If the treatment is ineffective, the subject can be administered a different antimicrobial treatment regimen (e.g., a different antimicrobial agent, or a combination therapy, or the same antimicrobial agent/treatment at a different dosage and/or administration schedule). The efficacy of the new antimicrobial treatment regimen can be determined by assaying a sample obtained after onset of the new treatment. Thus, an antimicrobial treatment regimen can be optimized or personalized for a subject by administering of different antimicrobial treatment regimen and assaying of samples by a PRR-based assay until the assay shows a change (e.g., increase, decrease, or spike) in a detectable signal level relative to a baseline level, indicating that the new treatment is effective.

In some embodiments, an antimicrobial treatment regimen is determined to be effective if a treatment related change (e.g., increase, decrease) or spike in a detectable signal level is by at least about 30% or more (including, at least about 40%, at least about 50%, at least about 60%, at least about 70%, at least about 80%, at least about 90%, at least about 95% or more), relative to a baseline level in a PRR-based assay. In some embodiments, an antimicrobial treatment regimen is determined to be effective if a treatment related increase or spike in a detectable signal level is by at least about 1.1-fold or more (including, at least about 1.5-fold, at least about 2-fold, at least about 3-fold, at least about 4-fold, at least about 5-fold, at least about 6-fold, or more), relative to a baseline level in a PRR-based assay.

In some embodiments, an antimicrobial treatment regimen is determined to be ineffective if a treatment related change (e.g., increase, decrease, or spike) in a detectable signal level is less than 30% or lower (including, less than 25%, less than 20%, less than 15%, less than 10%, less than 5%, less than 3%, less than 1% or lower) relative to a baseline level in a PRR-based assay.

In some embodiments, the methods of various aspects disclosed herein comprise initiating or administering an antimicrobial treatment to the subject.

In some embodiments where an effective antimicrobial treatment is determined or selected, the subject can be administered the selected antimicrobial treatment for a period of time, depending on life cycles of microbes infecting the subject. The period of time can range from about 1 week to 1 month or longer.

A method of screening for an effective antimicrobial agent is also provided herein. The method comprises: (a) contacting a sample comprising microbes to be treated or studied, with a candidate antimicrobial agent for varying amount of times; subjecting the sample treated for the varying amount of times to a PRR-based assay for detecting release of microbe-associated molecular patterns (MAMPs) induced by the candidate antimicrobial agent; and either (a) identifying the candidate antimicrobial agent to be effective if the kinetics profile of the MAMP release indicates a change (e.g., an increase, decrease, or spike) in a detectable signal relative to a baseline level upon contact with the candidate antimicrobial agent; or (b) identifying the candidate antimicrobial agent to be ineffective if the kinetics profile of the MAMP release does not indicate a change (e.g., increase, decrease, or spike) relative to the baseline level upon contact with the candidate antimicrobial agent.

The pharmaceutical screen for antimicrobial agents can be performed in vitro or in vivo. In some embodiments, the pharmaceutical screen for antimicrobial agents can be performed in animal models. For example, animal models of infection (e.g., pneumonia, urinary tract infection, endocarditis, osteomyelitis, meningitis, peritonitis, or any other infection of interest) can be setup by infecting animals with microbes that induce symptoms of infection to be studied.

The infected animals are then randomized to treatment groups to undergo treatment with a reference agent if there is one, with a placebo, and with a candidate antimicrobial agent to be evaluated in this indication.

A time course of a PRR-based assay (e.g., ELLecSA) can be measured in all animals in the course of treatment. Combination therapies or associations of immunomodulators or antivirulence agents can be assayed. The kinetics of the release of MAMPs recognized by the PRR in the assay can be determined and compared with the release obtained with the reference agent and the placebo. The candidate antimicrobial agent can be determined to be effective if the kinetics profile of the MAMP release indicates a change (e.g., increase, decrease, or spike) in a detectable signal relative to a baseline level (e.g., corresponding to the placebo upon contact with the candidate antimicrobial agent), or the candidate antimicrobial agent can be determined to be ineffective if the kinetics profile of the MAMP release does not indicate a change (e.g., increase, decrease, or spike) relative to the baseline level (e.g., corresponding to the placebo, such as without a candidate molecule or with an ineffective antimicrobial agent) upon contact with the candidate antimicrobial agent.

Time-course assay profiles can be interpreted according to different goals. For example, in some embodiments, microbicidal or bactericidal lysis activity of a test agent or an antimicrobial agent can be determined from area under a time course curve. In some embodiments, absence of lysis in conditions where therapeutic exacerbations by the antimicrobial agent can worsen the prognosis. In some embodiments, kinetics of the return of MAW release level to baseline can be determined from the time-course assay. With approved drugs, comparison of the efficacy of treatment can be undertaken in populations with challenging pharmacokinetic/pharmacodynamics (PK/PD) parameters.

In some embodiments, the methods of various aspects disclosed herein can comprise assaying a plurality of (e.g., at least two or more) samples obtained over a period of time from the subject for detecting treatment related change (e.g., increases, decrease, or spikes) in the detectable signal levels by a PRR-based assay. For example, in some embodiments, a sample can be obtained from the subject prior to an antimicrobial treatment, and at least one or more (including, e.g., at least two, at least three or more) another samples can be obtained from the subject over the course of the antimicrobial treatment.

Accordingly, in some embodiments, the method can further comprise generating a time course profile that indicates the amount of microbes or microbial matter (e.g., MAMPs) present in the sample before and after onset of the antimicrobial treatment. In some embodiments, the time course profile can comprise at least 2 time points, including at least one time point before onset of an antimicrobial treatment and at least one time point taken after the onset of the antimicrobial treatment. In some embodiments, the time course profile can comprise at least 3 time points, including at least one time point before onset of an antimicrobial treatment and a plurality of (e.g., at least 2 or more, including, e.g., at least two, at least three, at least four, at least five, at least six, at least seven, at least eight, at least nine, at least ten or more) time points taken after the onset of the antimicrobial treatment.

In some embodiments, the time course profile can comprise about 4-10 time points to show (i) initial baseline (i.e., before onset of an antimicrobial treatment), and (ii) effects of antimicrobial treatment. An effective antimicrobial treatment can lyse or kill the microbes to expose or release MAMPs, which generate an increase or spike in a detectable signal level relative to the initial baseline. In some embodiments where an increase or spike in a detectable signal level, relative to the initial baseline, is observed, the time course profile can further show a treatment plateau after the increase or spike. This indicates an effective antimicrobial treatment. For example, FIG. 12A shows a 24-hr time course profile where an increase or spike in a detectable signal level over time (corresponding to an increase in MAMPs over time), relative to the initial baseline, is observed with ceftriaxone (CRO), not cefazoline (CF), indicating that the CRO treatment is effective but CF treatment is ineffective. As an antibiotic becomes more effective over time, more MAMPs are released, resulting in a higher signal.

Relevant breakpoints for changes in assay levels can be determined by clinical practice for relevant presentations of clinical infections.

In some embodiments when the subject has a high baseline of MAMP level, the antimicrobial treatment can be identified to be effective if a treatment related decrease in the detectable signal level relative to the baseline level is present. In some embodiments, the subject previously underwent an ineffective antimicrobial treatment before the onset of a different antimicrobial treatment. In these embodiments the subject's infection can progress such that microbes proliferate and shed high levels of MAMPs, resulting in a high MAMP baseline. When a different antimicrobial treatment administered to a subject is effective, the MAMP detectable signal level can decrease relative to the high MAMP baseline (e.g., due to the MAMPs being cleared and no new MAMPs are generated). In some embodiments where an antimicrobial treatment is effective, the MAMP detectable signal level can increase relative to the high MAMP baseline for a period of time before the decrease (e.g., due to lysis and/or killing of microbes followed by MAMPs being cleared and no new MAMPs are generated). Accordingly, depending on when a sample is taken from a subject during the course of an antimicrobial treatment, the direction of change in MAMP detectable signal level can change accordingly.

In some embodiments when the subject has a low baseline of MAMP level, the antimicrobial treatment can be identified to be effective if a treatment related increase in the detectable signal level related to the baseline level is present. Without wishing to be bound by theory, the treatment related increase in the detectable signal level can be induced by MAMPs released or exposed by microbes after contact with the antimicrobial treatment. In some embodiments, the subject, who initially shows a low MAMP baseline, is diagnosed for having an infection at the early stage, or having a risk of developing an infection.

Accordingly, the time course of obtaining samples from a subject for the assay can be guided by pharmacokinetic-pharmacodynamics properties of the subject/antimicrobial agent combination.

The methods disclosed herein can also be used to monitor infection progression or treatment effectiveness. One can monitor the progression of infection and/or treatment effectiveness by using the methods disclosed herein to detect increases and/or decreases (e.g. spikes) in detectable signal levels over a period of time by serial sampling. The monitoring can continue until the detectable signal level returns to a background level.

Thus, the method disclosed herein provide for monitoring of in vivo activity of the antimicrobial agent as the antibiotic clears the infection decreasing, as well as determining the change (e.g., increase, decrease, or "spike") in the detectable signal level (e.g., MBL ELLecSA signal) as a result of antimicrobial treatment. Further one can monitor the progression of infection and treatment effectiveness (increases and decreases in the detectable signal level (e.g., FcMBL ELLecSA signal)) by serial sampling until the signal returns to background.

Treatment Related Change (e.g., Increase, Decrease, or Spike) in a Detectable Signal Level Relative to a Baseline Level Without wishing to be bound by a theory, treatment related change (e.g., increases, decrease, or spikes) in detectable signal level can correspond to a change (e.g., an increase or a decrease) in the level of MAMPs derived from microbes treated with at least one or more antimicrobial agents. In some embodiments, an antimicrobial agent can lyse or kill microbes to expose, release or generate MAMPs, resulting in an increase in MAMPs in blood of a subject. As the concentration/amount of the antimicrobial agent decreases in vivo (e.g., due to metabolism, clearance, degradation, etc. . . . ), and/or the levels of exposed or released MAMPs decreases in vivo (e.g., due to clearance or phagocytosis) and/or no new MAMPs are generated, the detectable signal level can decrease. Thus, by assaying the MAMP level in samples obtained over a period of time, treatment related change (e.g., increases, decrease, and/or spikes) in the detectable signal levels in the assay can be determined. For example, the assay step can comprise assaying two or more different samples from the subject obtained at different time points after the onset or administration of the treatment regimen. The time course of obtaining the samples from the subject for the assay can be guided by the pharmacokinetic-pharmacodynamics properties of the subject/antimicrobial agent combination. For example, if an antimicrobial agent is fast-acting, a sample can be taken at an earlier time point than when a slow-acting antimicrobial agent is used.

In some embodiments, the time course or time points of obtaining the samples from the subject for the assay can be selected based on, e.g., the kinetics of the expected microbe proliferation and/or pharmacokinetics/pharmacodynamics (PK/PD) of an antimicrobial agent, e.g., kinetics of MAMPs released by the microbes upon contact with the antimicrobial agent. In some embodiments, the time points can be selected such that the treatment-related effect of MAMP release dominates over the microbe proliferation and shedding. In some embodiments, the time point can be a time point at which the subject has been administered with an antimicrobial treatment for no longer than 3 days, no longer than 2 days, no longer than 1 day. In some embodiments, the time point can be a time point at which the subject has been administered with an antimicrobial treatment for no longer than 24 hours, no longer than 18 hours, no longer than 12 hours, no longer than 9 hours, no longer than 6 hours, no longer than 5 hours, no longer than 4 hours, no longer than 3 hours, no longer than 2 hours, no longer than 1 hour, no longer than 30 minutes or less. For example, fast-acting antibiotics (e.g., but not limited to Amikacin) can produce a treatment-related effect of MAMP release in less than 4 hours, less than 2 hours, or less than 1 hour. In contrast, slow-acting antibiotics would require longer time to produce a treatment-related effect of MAMP release; thus, a longer pre-determined period of time can be selected.

By "treatment related increase in a detectable signal level" is meant that a detectable signal level increases within a period of time after administering of an antimicrobial treatment. Thus, the increase in the detectable signal level is due to the therapeutic action of the antimicrobial treatment (e.g., lysing or killing the microbes to expose or release MAMPs).

The term "spike" as used herein refers to a sharp change in a detectable signal level within a period of time after administering of an antimicrobial treatment. The sharp change can be a sharp increase or a sharp decrease. In some embodiments, the term "treatment related spike in a detectable signal level" as used herein refers to a sharp increase in a detectable signal level, followed by a sharp decrease in a detectable signal level, within a period of time after administering of an antimicrobial treatment. Thus, the increase and decrease in the detectable signal level is due to the therapeutic action of the antimicrobial treatment (e.g., lysing or killing the microbes to expose or release MAMPs, which are then phagocytosed or cleared from blood).

By "treatment related decrease in a detectable signal level" is meant that a detectable signal level decrease within a period of time after administering of an antimicrobial treatment. The decrease in the detectable signal level can be due to the clearance of MAMPs and/or no more new MAMPs being generated.

As used herein and throughout the specification, the term "detectable signal level" generally refers to a target molecule being present at a level that is detected in a sample by an assay. In the context of the disclosure described herein, the term "detectable signal level" refers to microbes, or components, MAMPs, and/or secretion thereof being present at a level that is detected in a sample by an assay (e.g., a PRR-based assay). In some embodiments, a detectable signal level is indicative of the presence of MAMPs at a level that is detected in sample by a PRR-based assay. A detectable signal level can be detected by spectroscopic, photochemical, biochemical, immunochemical, electrical, optical, enzymatic, magnetic, or chemical means. Accordingly, detectable signals can include, but are not limited to, color, fluorescence, chemiluminescence, radiation, and the like.

Generally, a detectable signal can be produced by a detectable label in the assay. As used herein, the term "detectable label" refers to a molecule/composition capable of producing a detectable signal indicative of the presence of a target molecule. Suitable labels include fluorescent molecules, radioisotopes, nucleotide chromophores, enzymes, substrates, chemiluminescent moieties, magnetic particles, bioluminescent moieties, and the like. As such, a detectable label is any molecule/composition detectable by spectroscopic, photochemical, biochemical, immunochemical, electrical, optical, enzymatic, magnetic, or chemical means. The label can bind directly with the target or can bind a molecule/composition which binds to the target. By way of example only, in some embodiments, a detectable label is a horseradish peroxidase (HRP)-conjugated PRR molecule (e.g., but not limited to MBL-HRP, or CRP-HRP).

In some embodiments, the treatment-related change (e.g., increase, decrease, or spike, e.g., due to destruction of microbes and/or release of MAMPs (e.g., microbe carbohydrates), and/or clearance of MAMPs upon administration of an effective antimicrobial therapy) relative to the baseline can occur in a different time scale than that of an expected change (e.g., increase, decrease, or spike) in the signal, e.g., due to proliferation of microbes (if the treatment is ineffective). However, in some embodiments, the treatment-related change (e.g., increase, decrease, or spike) can occur in a comparable time scale as that of an expected change (e.g., increase, decrease or spike) in signal, e.g., due to microbial proliferation. In these embodiments, the treatment-related change (e.g., increase, decrease, or spike) relative to the baseline level can be greater than the expected change (e.g., increase, decrease, or spike) in the signal due to proliferation of microbes (if the treatment is ineffective) by at least about 5%, at least about 10%, at least about 15%, at least about 20%, at least about 25%, at least about 30%, at least about 40%, at least about 50%, at least about 60%, at least about 70%, at least about 80%, at least about 90%, at least about 95% or more. In some embodiments, the treatment-related change (e.g., increase, decrease, or spike) relative to the baseline can be greater than the expected increase in the signal due to proliferation of microbes (if the treatment is ineffective) by at least about 1.1-fold, at least about 1.5-fold, at least about 2-fold, at least about 3-fold, at least about 4-fold or more. In some embodiments, the expected increase in the signal due to microbial proliferation can be determined or estimated based on, e.g., the time point at which the measurement is taken, cell proliferation rate, the baseline measured from the subject, and any combinations thereof.

The methods disclosed herein call for comparing detection signal levels to a baseline level. In some embodiments, the baseline level can be a detection signal level from assaying a sample obtained from the subject before onset of the antimicrobial treatment regimen. For example, a sample from the subject can be obtained before onset of antimicrobial treatment. The sample can be assayed by a PRR-based assay described herein to establish a baseline level for the detectable signal. Alternatively, or in addition, a baseline level can be established by assaying a sample obtained after onset of treatment is assayed. In either case, a change (e.g., increase, decrease, or spike) in the detectable signal level in the treatment sample indicates diagnosis of infection and/or efficacy of the treatment regimen.

Depending on applications, the baseline level can vary in the methods of various aspects described herein. In some embodiments of various methods described herein, a detectable signal level can be compared to more than one baseline levels. In some embodiments of some aspects described herein, a baseline level can correspond to a signal resulted from assaying the same sample with a PRR-based assay (e.g., a lectin based assay) without pre-treating the sample to lyse or kill microbes. In some embodiments of some aspects described herein, a baseline level can correspond to a signal resulted from assaying a sample collected from a subject prior to administration of an antimicrobial treatment, with a PRR-based assay (e.g., a lectin based assay). In some embodiments of some aspects described herein, a baseline level can correspond to a signal resulted from assaying a sample collected from a subject at a first time point after administration of an antimicrobial treatment, with a PRR-based assay (e.g., a lectin based assay). In some embodiments of some aspects described herein, a baseline level can correspond to a signal resulted from a PRR-based assay (e.g., a lectin based assay) of a sample that was collected from a subject prior to administration of an antimicrobial treatment and has subsequently been cultured in vitro under a physiological condition for substantially the same amount of time after the subject has been given the antimicrobial treatment. In some embodiments of some aspects described herein, the baseline level can be a level from assaying sample which does not have microbe therein. For example, the baseline level can be established based on a sample from a normal healthy person (e.g., without infection). In some embodiments of some aspects described herein, a baseline level can correspond to an infection baseline as defined herein.

In some embodiments of various aspects described herein, the treatment related change in detectable MAMP signal level can refer to degree or extent of change in detectable MAMP signal level relative to a baseline level. For example, the treatment related change in detectable MAMP signal level can refer to a degree or extent of increase or decrease in detectable MAMP relative to a baseline level.

In some embodiments of various aspects described herein, the treatment related change in detectable MAMP signal level can also refer to the rate of change in detectable MAMP signal level relative to a baseline level. In some embodiments, the treatment related change in detectable MAMP signal level can refer to the rate of increase in detectable MAMP signal level being higher than the rate of increase in a control sample (e.g., a sample without an antimicrobial treatment or a sample with an ineffective antimicrobial treatment). In some embodiments, the treatment related change in detectable MAMP signal level can refer to the rate of decrease in detectable MAMP signal level being higher than the rate of decrease in a control sample (e.g., a sample without an antimicrobial treatment or a sample with an ineffective antimicrobial treatment). In some embodiments, the treatment related change in detectable MAMP signal level can refer to the rate of increase in detectable MAMP signal level being smaller than the rate of increase in a control sample. In some embodiments, the treatment related change in detectable MAMP signal level can refer to the rate of decrease in detectable MAMP signal level being lower than the rate of decrease in a control sample.

Pattern Recognition Receptor (PRR)-Based Assay (e.g., a Lectin Based Assay)

As defined earlier, the term "pattern recognition receptor-based assay" or "PRR-based assay" refers to a method/assay and/or composition used to bind a microbe and/or microbial matter (e.g., MAMPs) comprising use of at least one or more PRRs, where the term "PRR" is defined earlier. In some embodiments, a PRR-based assay can refer to capture of a microbe and/or microbial matter (e.g., MAMPs) comprising use of at least one or more PRRs. In some embodiments, a PRR-based assay can refer to use of at least one or more PRRs to provide a detectable signal in the presence of a microbe and/or microbial matter (e.g., MAMPs). In some embodiments, a PRR-based assay can refer to use of at least one or more PRRs to capture a microbe and/or microbial matter (e.g., MAMPs) and also to provide a detectable signal in the presence of the microbe and/or microbial matter (e.g., MAMPs). In these embodiments, the same or different PRRs can be used in both the capture and signal detection steps.

In some embodiments, a PRR-based assay (e.g., lectin based assay) can comprise use of at least one PRR such as lectin (e.g., a mannan binding lectin or molecule) bound to a solid substrate for capturing or isolating the microbe or microbial matter from the sample for subsequent detection. Examples of solid substrate can include, but are not limited to, beads or particles (including nanoparticles, microparticles, polymer microbeads, magnetic microbeads, and the like), filters, fibers, screens, mesh, tubes, hollow fibers, scaffolds, plates, channels, gold particles, magnetic materials, medical apparatuses (e.g., needles or catheters) or implants, dipsticks or test strips, filtration devices or membranes, hollow fiber cartridges, microfluidic devices, mixing elements (e.g., spiral mixers), extracorporeal devices, and other substrates commonly utilized in assay formats, and any combinations thereof. In some embodiments, the solid substrate can be a magnetic particle or bead.

In some embodiments, the PRR-based assay (e.g., lectin based assay) can comprise use of at least one PRR such as lectin (e.g., a mannan binding lectin or molecule) conjugated with a detectable label for detecting the microbe or microbial matter in the sample or isolated from the sample.

In some embodiments, the PRR used in the PRR-based assay can comprise at least a portion of a pentraxin family protein, such as C-reactive protein (CRP). In some embodiments, the CRP can be a recombinant CRP, such as CRP-Fc. CRP is described in, for example, U.S. Provisional patent application No. 61/917,705, filed Dec. 18, 2013, the content of which is incorporated herein by reference in its entirety.

In some embodiments, the PRR(s) used in a PRR-based assay can comprise a lectin-based molecule. As used herein, the term "lectin-based molecule" refers to a molecule comprising a microbe-binding domain derived from at least a portion of lectin. The term "lectin" as used herein refers to any molecules including proteins, natural or genetically modified (e.g., recombinant), that interact specifically with saccharides (e.g., carbohydrates). The term "lectin" as used herein can also refer to lectins derived from any species, including, but not limited to, plants, animals, insects and microorganisms, having a desired carbohydrate binding specificity. Examples of plant lectins include, but are not limited to, the Leguminosae lectin family, such as ConA, soybean agglutinin, peanut lectin, lentil lectin, and *Galanthus nivalis* agglutinin (GNA) from the *Galanthus* (snowdrop) plant. Other examples of plant lectins are the Gramineae and Solanaceae families of lectins. Examples of animal lectins include, but are not limited to, any known lectin of the major groups S-type lectins, C-type lectins, P-type lectins, and I-type lectins, and galectins. In some embodiments, the carbohydrate recognition domain can be derived from a C-type lectin, or a fragment thereof. C-type lectin can include any carbohydrate-binding protein that requires calcium for binding (e.g., MBL). In some embodiments, the C-type lectin can include, but are not limited to, collectin, DC-SIGN, and fragments thereof. Without wishing to be bound by theory, DC-SIGN can generally bind various microbes by recognizing high-mannose-containing glycoproteins on their envelopes and/or function as a receptor for several viruses such as HIV and Hepatitis C.

Accordingly, in some embodiments, the PRR-based assay is a lectin based assay.

In some embodiments, the lectin used in the lectin based assay is a mannose binding lectin (MBL). In some embodiments, the lectin is a recombinant lectin such as FcMBL. FcMBL is a fusion protein comprising a carbohydrate recognition domain (CRD) of MBL and a portion of immunoglobulin. In some embodiments, the FcMBL further comprises a neck region of MBL. In some embodiments, the N-terminus of FcMBL can comprise an oligopeptide adapted to bind a solid substrate and orient the CRD of MBL away from the solid substrate surface. Various genetically engineered versions of MBL (e.g., FcMBL) are described in International Application Nos. WO 2011/090954 and WO 2013/012924, the contents of each of which are incorporated herein by reference in their entireties. Lectins and other mannan binding molecules are also described in, for example, U.S. patent application Ser. No. 13/574,191 (now U.S. Pat. No. 9,150,631); PCT application no. PCT/US2011/021603, PCT/US2012/047201, and PCT/US2013/028409; and U.S. Provisional application No. 61/691,983 filed Aug. 22, 2012, content of all of which are incorporated herein by reference in their entireties. Thus, in some embodiments, the lectin based assay is an FcMBL based assay. As used herein, the terms "FcMBL based detection," "FcMBL based assay," "FcMBL based detection method," and variants thereof refer to target molecule capture/detection methods and compositions comprising use of a FcMBL or variants thereof for capturing microbes and/or microbial matter (e.g., MAMPs) and/or providing a detectable signal in the presence of microbes and/or microbial matter (e.g., MAMPs).

Exemplary lectin (e.g., FcMBL) based microbe detection assays and compositions are described in, for example, PCT application no. PCT/US2012/047201, no. PCT/US2013/028409, and no. PCT/US14/28683, filed Mar. 14, 2014, and U.S. Provisional application No. 61/691,983 filed Aug. 22, 2012, No. 61/788,570 filed Mar. 15, 2013, No. 61/772,436 filed Mar. 4, 2013, No. 61/772,360 filed Mar. 4, 2013, content of all of which are incorporated herein by reference in their entireties.

In some embodiments, the lectin based assay generally relies on the capture of microbes/microbial components (e.g., MAMPs) from a sample using lectin molecules bound to a solid substrate (e.g., polymeric or magnetic particles or beads), followed by detection of the materials captured from the sample. Without wishing to be bound by a theory, particles (e.g., magnetic particles) of different sizes can be used for capturing/detecting different microbes intact vs disrupted/lysed material. For example, inventors have shown that particles of smaller size (e.g., 128 nm) have a higher efficiency for capturing intact microbes. On the other hand, particles of larger size (e.g., 1 µm) have a higher efficiency for capturing microbial disrupted/lysed materials, e.g., MAMPs.

Accordingly, in some embodiments, particles of larger size can be better suited, e.g., for used for capturing and/or detecting the absence or presence of the microbial matter (e.g., MAMPs) and the particles of smaller size can be used for capture of intact bacteria, e.g., for further testing such as antibiotic susceptibility. Particles of other sizes and/or alternative chemistry can also be used, e.g., depending on the types of microbes/microbial matter to be captured/detected.

While, in some embodiments, microbes and/microbial matter (e.g., MAMPs) can be captured by PRR-coated solid substrates prior to detection, in other embodiments, microbes and/or microbial matter (e.g., MAMPs) can also be detected by PRR-coated detectable label as defined herein, e.g., PRR-coated fluorescent molecule, without prior capture. In these embodiments, the microbes and/or microbial matter (e.g., MAMPs) can be bound, mounted or blotted onto a solid surface, e.g., a tissue surface, and a membrane surface.

The microbes and/or microbial matter (e.g., MAMPs) bound to PRR-coated (e.g., lectin-coated) solid substrates (e.g., polymeric or magnetic particles or beads) or a solid surface can be detected by any methods known in the art or as described herein. Examples of detection methods can include, but are not limited to, spectroscopy, electrochemical detection, polynucleotide detection, fluorescence anisotropy, fluorescence resonance energy transfer, electron transfer, enzyme assay, magnetism, electrical conductivity, isoelectric focusing, chromatography, immunoprecipitation, immunoseparation, aptamer binding, filtration, electrophoresis, use of a CCD camera, immunoassay, ELISA, Gram staining, immunostaining, microscopy, immunofluorescence, western blot, polymerase chain reaction (PCR), RT-PCR, fluorescence in situ hybridization, sequencing, mass spectroscopy, or substantially any combination thereof. The captured microbe can remain bound on the PRR-coated solid substrates during detection and/or analysis, or be isolated form the PRR-coated solid substrates prior to detection and/or analysis.

ELISA: In some embodiments, the microbes and/or microbial matter (e.g., MAMPs) bound to PRR-coated (e.g., lectin-coated) solid substrates (e.g., polymeric or magnetic particles or beads) can be detected by ELLecSA as defined herein, an example which is described in detail in the section "An exemplary enzyme-linked lectin sorbent assay (ELLecSA)" below. Additional information various embodiments of FcMBL based assays can be found, e.g., in PCT application no. PCT/US2012/047201, no. PCT/US2013/028409, and no. PCT/US14/28683, the contents of all of which are incorporated herein by reference in their entireties.

Immunoassay: In some embodiments, the microbes and/or microbial matter (e.g., MAMPs) bound to PRR-coated (e.g., lectin-coated) solid substrates (e.g., polymeric or magnetic particles or beads) can be detected by antibodies that bind to MAMPs. For example, antibodies can include, but are not limited to, anti-LPS antibodies, and anti-Staph antibodies. In some embodiments, the antibodies can be labeled with a detectable label such as HRP labeling reagents and/or fluorescent labeling reagents.

In some embodiments, the microbes and/or microbial matter (e.g., MAMPs) bound to PRR-coated (e.g., lectin-coated) solid substrates (e.g., polymeric or magnetic particles or beads) can be detected by non-labeling methods.

Polymerase chain reaction (PCR) or quantitative PCR: For example, in some embodiments, microbes and/or microbial matter (e.g., MAMPs) can be detected by polymerase chain reaction (PCR) or quantitative PCR (qPCR). Once microbes and/or MAMPs have been captured on PRR-coated solid substrates, the PRR-coated solid substrates with bound microbes and/or MAMPs can be removed from the sample matrix that can contain both inhibitory molecules that prevent effective gene amplification and excess host DNA that can compete with the primers used for specific microbial targets. The sensitivity of PCR and its specificity can be increased by the removal of unwanted host DNA that could generate a false positive signal.

Primers for gene amplification can either be specific for a given genus, species or clone of microorganism or generic of prokaryote, archeal or eukaryote phylum. Sequencing of an amplification fragment can allow the identification of the microbes in the sample using a database query system.

Sequencing: Alternatively or additionally, the DNA materials bound to the PRR-coated beads can be detected by high throughput sequencing or direct sequencing. Thus, identification, typing and/or detection of resistance determinants in a micro-organism can be determined.

Mass spectrometric methods: In some embodiments, microbes and/or microbial matter (e.g., MAMPs) captured on PRR-coated solid substrates can be detected by a mass spectrometric method. Exemplary mass spectrometric methods include, but are not limited to MALDI, LC-MS, GC-MS, and ESI-MS.

The chemical or physical analysis of the microbial material (e.g., MAMPs) bound to the PRR-coated solid substrate (e.g., polymeric or magnetic particles) by mass spectrometry using either MALDI or LC-MS or GC-MS or spectroscopy (raman or otherwise) can allow detection and/or identification of the bound material. In one embodiment, analysis of elute from the FcMBL-coated beads has shown different MALDI-TOF MS profile depending on the types of microbes captured on the FcMBL-coated beads (FIG. 14).

The analysis of the material eluted from the PRR-coated solid substrates (e.g., PRR-coated beads) can be identified to either a molecular level or a general pattern, which can be subsequently matched to a known database of profiles derived from previous isolates or patient samples. The construction of a profile database and the algorithms used to match a sample to a microbe or group of microbes can rely on scores determined according to the presence or absence of known or unknown characteristics of individual microbes or microbe classes.

Surface plasmon resonance: Alternatively or additionally, the kinetics of binding of MAMPs to the PRR-coated solid substrates can be detected in real time using surface plasmon resonance or similar detection technologies.

Phagocytosis assay: The inventors found that FcMBL-coated beads were mostly not phagocytized by THP-1 cells, while MAMP coating FcMBL-coated beads were phagocytized. Accordingly, in some embodiments, PRR-coated beads or particles with bound microbes and/or MAMPs can be detected by determining the number of immune cells that phagocytize the PRR-coated beads with bound microbes and/or MAMPs. In some embodiments, the immune cells used in the phagocytosis assay can be THP-1 cells, which is a human monocytic cell line derived from an acute monocytic leukemia patient.

Upon phagocytosis the THP-1 cells are laden with PRR-coated beads bound with microbes and/or microbial matter (e.g., MAMPs). In some embodiments, the PRR-coated beads can be superparamagnetic PRR-coated beads. In these embodiments, either the non-magnetic cells without phagocytosis activity or the cells that are susceptible to magnetic capture due to the phagocytosis of MAMP coating PRR-coated superparamagnetic microparticles, can be detected. The number or percentage of THP-1 cells associated to PRR microparticles can be a metric of the amount of MAMPs bound PRR-coated beads and therefore a quantitative or semi-quantitative measure of the amount of MAMP in the sample.

In some embodiments, the PRR-coated beads can be fluorescently labeled and the number or percentage of THP-1 cells associated to fluorescently labeled PRR tethered beads can be a metric of the amount of MAMPs bound PRR-coated beads.

In some embodiments, about $10^6$-$10^7$ THP-1 cells can be incubated with PRR-coated beads bound with microbes and/or microbial matter (e.g., MAMPs). The bead/cell mixture can then be gently pelleted and resuspended in a fixation buffer for flow cytometry detection of THP-1 cells that have phagocytosed fluorescently-labeled PRR-coated beads bound with microbes and/or microbial matter (e.g., MAMPs). In some embodiments where the PRR-coated beads are magnetic, the THP-1 cells that phagocytosed magnetic beads can be separated from other THP-1 cells without phagocytosis of magnetic beads. An exemplary protocol for phagocytosis assay is described in Example 11, and can be used to detect microbes and/or microbial matter (e.g., MAMPs) bound onto PRR-coated beads.

The cellular activation of the macrophages can be further studied by fluorescent staining of membrane clusters of differentiation (CD) markers, or of intracellular markers in the case of a flow cytometry analysis, or by studying the transcriptomic response to the beads, which can be used to discriminate between bacterial types according to the qualitative nature of the response.

In some embodiments, the quantitative detection of THP-1 cells can be achieved by detection of the amount of magnetically selected phagocytes either by quantitation of live cells (bactiter-glo assay (Promega) or by flow cytometry measuring the presence of Cy-3 positive beads and CD9+ and/or CD11a+ and/or CD18+ and/or CD31+ and/or CD36+ and/or CD45+ and/or other relevant THP-1 cell-surface markers.

Alternatively, a multiplex ELISA assay can detect both the PRRs such as MBL (quantification of the beads) and the THP-1 specific markers.

In some embodiments, a blood sample (e.g., whole blood) of a patient can be incubated with PRR-coated magnetic particles (e.g., FcMBL-coated superparamagnetic microparticles) at ~37° C. in the presence of calcium and a non-calcium chelating anticoagulant. Under these circumstances, the phagocytes present in the patient's blood would attach to PRR-coated magnetic particles that are bound with MAMPs, and engulf them. Upon magnetic capture the phagocytes laden with magnetic microparticles can be washed and quantified by immunophenotyping methods (CD45+ and CD15+ or CD14+ or other relevant CD markers). In some embodiments, it can be desirable to dilute the blood sample of the patient prior to the incubation with PRR-coated magnetic particles.

While this method has the advantage of minimizing the steps required to perform the assay it is dependent on the presence of active phagocyte within the patient's blood sample.

In some embodiments, the number of THP-1 cells that phagocytosed PRR-coated beads bound with MAMPs can be compared with a control. For example, a control can be the amount of leukocytes in the non-magnetically bound fraction and/or leukocytes in the total sample dilution. In addition, non-specific pathological phagocyte activation can be ruled out by assaying the amount of phagocytosis of non-PRR coated beads (i.e. beads coated with non-PRR proteins or PEG, also termed as "blocked beads").

Engineered reporter cells: In some embodiments, the biological detection of the MAMPs present on the PRR-coated beads can involve different reporter cells. For example, engineered cells with recombinant surface PRR can be placed in microfluidic chambers. An array of such chambers can be set up in a device such as any art-recognized microfluidic device for cell culture, or in a "farm" where microfluidic devices would be chained. The engineered cells can be further engineered to report the activation of the relevant early PRR pathways using fluorescent and/or luminescent and/or enzymatic beacons. In some embodiments, a microfluidic device can be adopted from an organ-on-chip device. As used herein, the term "organ-on-chip device" refers to a device (e.g., a cell culture device or a microfluidic device) that used to culture and/or support living cells (e.g., but not limited to, mammalian cells such as human cells) under fluid or gas flow in its chambers (including, e.g., microfluidic channels). In some embodiments, at least some cells can form functional tissues and tissue-tissue interfaces that can recapitulate those found in whole living organs. Mechanical forces can also be applied repetitively to the organ-on-chip devices in order to mimic the dynamic physical microenvironment of cells.

Such microfluidic devices or "farm" can allow the assay a broad range of cellular PRR reporters not readily ported to a single molecule format and benefitting from an intracellular amplification cascade.

The array of cellular detectors can be endocytic pathways not present at the surface of the plasmic membrane but selectively expressed on the endocytic compartment. The internalization of the MAMP-coated microparticle presented to the cell would be phagocytized and thus would trigger the endosomal detection and activation of the innate immune pathway (NF-kB in the case of Toll like receptors or other).

PRR-coated bead aggregation-based methods: Inventors have discovered that when microbes and/or microbial matter bound onto PRR-coated beads or particles, the beads or particles aggregate or clump and form superstructures. Without wishing to be bound by theory, many MAMPs harbor multiple PRR binding sites and engaging a PRR on one PRR-coated particle leaves other PRR binding sites available for detection with another PRR tethered to a reporter such as an enzyme in ELLecSA. The same mechanism leaves the second or N-th binding site available to engage a PRR attached to the surface of another particle. This cross linking between multiple PRR-coated particles does not interfere with the detection using ELLecSA since particle complexes leave multiple permeable tracts that the smaller detection molecules can access when particles are hindered mechanically.

Accordingly, the crosslinking or aggregation of PRR-coated particles can be used as a detection method to detect the presence of microbes and/or MAMPs in a subject's sample. For example, large PRR-coated microparticles (e.g., with a size ranging from about 50 nm to about 50 µm) can be used to visualize the crosslinking/agglutination step. In the presence of microbes and/or MAMPs, the PRR-coated microparticles will agglutinate providing a visually observable readout. Without wishing to be bound by theory, the crosslinking/agglutination between PRR-coated particles can work in a similar manner as an art known agglutination kit commonly used for the rapid detection of an antigen in blood group determination. Latex (common name for polystyrene in the diagnostic industry) beads coated with Fc and clumping factor and anti capsular antibody are thus frequently used to identify *Staphylococcus aureus* based on its surface determinants recognized by the antibodies present on the beads, or presumptive identification of streptococci based on the detection of Lancefield antigenic groups.

The microparticles for use in PRR-coated microparticles can be erythrocytes or synthetic micro particles, and agglutination can be detected using a naked eye. Accordingly, this PRR-coated bead aggregation-based method can be adapted for use in point of care diagnostic without other detection equipment.

In some embodiments, the use of magnetic microparticles (e.g., superparamagnetic microparticles) can allow for easier washing and recovery of the microparticles, for automating the time of incubation with the sample, and also for working with whole blood with no interference from the erythrocytes.

In some embodiments, the agglutination or crosslinking of the PRR-coated microparticles in the presence of microbes and/or microbial matter (e.g., MAMPs) can be quantified. For example, the detection of the clumping or crosslinking PRR-coated microparticles can be measured by the accelerated sedimentation rate of bead/particle clumps that settle in a capillary, thus measuring the microparticle sedimentation time, e.g., in a manner as erythrocyte sedimentation time is determined for anticoagulated blood.

In some embodiments, the detection of the clumping or crosslinking PRR-coated microparticles can be measured by a densitometer such as the ones commonly used in the industry for the determination of bacterial concentration in a suspension (McFarland scale). A decrease from the initial read determined by bead/microparticle density (e.g., target density can be about $10^8$ microparticles/ml) can be an indicator of clumping/agglutination of the PRR-coated microparticles. A control with non-PRR-coated microparticles or blocked beads (e.g., microparticles coated with non-PRR proteins or PEG) can be used to rule out non-specific loss of beads in the sample due to non-specific binding. The readout can be expressed as a ratio of McFarland reads on the microparticles prior to the incubation and after the incubation, with a control (e.g., non-PRR-coated microparticles or blocked beads) of a value approaching 1.

In some embodiments, a flow cytometer can be used to determine the size of the clumping or agglutination of PRR-coated microparticles in the presence of microbes and/or microbial matter (e.g., MAMPs) by SSC and FSC (side and forward scatter) of the microparticles after the washes. Using a combination of SSC, FSC and fluorescently labeled beads, the size and fluorescent intensity of a PRR coated microparticle clusters can be determined in whole blood with no need to perform any washes.

In some embodiments, detection of clumping or agglutination of PRR-coated microparticles or beads in the presence of microbes and/or microbial matter (e.g., MAMPs) by a flow cytometer can be performed as follows:

A sample is collected into a tube with an anticoagulant if the sample can potentially coagulate The sample is diluted appropriately. In some embodiments, the sample can be diluted in about 1:5 or 1:10 ratio. The diluting medium can comprise calcium (if the PRR is calcium dependent) or any other required supplement required by the MAMP to PRR binding kinetics. If the PRR is lectin based, glucose or mannose or any other sugar of adequate affinity below that of the MAMP to PRR binding can be used. See PCT/US14/28683—filed Mar. 14, 2014, the content of which is incorporated herein by reference, for additional information about addition of a sugar molecule into a sample for improved detection sensitivity.

The sample is incubated for about 10 to 20 minutes with PRR-coated beads fluorescently labeled with one dye and control beads (e.g., non-PRR-coated beads or blocked beads) labeled with another dye. The possible phagocytosis of beads by leucocytes is not a problem due to the frequent phagocytosis of clumps. The detection of a leucocyte with a single bead as a specific event can be reported as part of the test report. The use of control beads allows for the simultaneous measurement of the behavior of beads specifically or non specifically engaging MAMPs.

Use of different fluorescently labeled microparticles or beads with specific fluorescence spectra can allow the recognition of the engagement of a specific combination of MAMPs (multiplex detection of MAMPs) by an array or mixture of microparticles coated with different PRRs. In some embodiments, a multi-laser flow cytometer can be used for detection, and/or a dye mixture combination commonly used in multiplex assays can be used for labeling different PRR-coated microparticles. In some embodiments, different PRR-coated microparticles are selected or engineered to prevent PRR-PRR interactions during multiplex detection of MAMPs.

Nuclear magnetic resonance: The use of magnetic resonance relaxation time determination can also be used for detection of the MAMP binding to PRR-coated microparticles or beads. Such a methodology has been used by T2 systems to build a specific agglutination detector that can be used for MAMP-PRR coated microparticles clustering.

An Exemplary Enzyme-Linked Lectin Sorbent Assay (ELLecSA)

As defined earlier, the term "enzyme linked lectin sorbent assay" or "ELLecSA" refers to an assay that uses at least one lectin and color change to detect or determine the presence of a microbe or microbial matter, e.g., MAMPs, in a sample. The working principle of ELLecSA is similar to art known enzyme-linked immunosorbent assay (ELISA), except that lectins are used in ELLecSA, while antibodies are used in ELISA. Thus, in some embodiments, an ELLecSA assay can be a dual lectin sandwich ELLecSA, in which a lectin-based molecule is used to capture a microbe or microbial matter (e.g., MAMPs), and an enzyme-linked lectin-based molecule is used as a detection lectin that also binds to the captured microbe or microbial matter, wherein the enzyme converts a chemical substrate to be added into a color or fluorescent or electrochemical signal.

An exemplary process for capture/detection of microbes and/or microbial matter (e,g, MAMPs) from a sample is as follows. The sample or "suspension" to be tested can be diluted with a buffered solution containing Ca', optionally supplemented with a blocking agent, which can be added to enhance specificity and/or sensitivity of microbial capture (e.g., a 6-carbon oside such as glucose or mannose) as described in PCT Application Serial No. PCT/US14/28683, filed Mar. 13, 2014, content of which is incorporated herein by reference in its entirety. In the case of blood, plasma or serum, heparin can be added to the sample. Lectin-coated substrates (e.g., FcMBL-coated superparamagnetic beads) are added and microbial capture can be carried out optionally with agitation, e.g., for about 20 minutes. After capture, lectin-coated substrates are then separated accordingly from the sample. For example, magnetic separation can be used to separate lectin-coated magnetic beads from the sample. The separated lectin-coated substrates (e.g., FcMBL-coated magnetic beads) are then optionally washed (e.g., at least once, at least twice or more) in a buffer (optionally containing $Ca^{2+}$) and assayed for the presence or absence of microbe and/or MAMPs.

After the microbe and/or MAMPs is enriched by capture on the lectin-coated substrates (e.g., FcMBL-coated magnetic beads), the lectin-coated substrates can be contacted or incubated with a detectable label capable of producing a detectable signal indicative of the presence of microbe and/or MAMPs.

In some embodiments, the detectable label can be a PRR (e.g., a lectin molecule) conjugated with a molecule capable of producing a detectable signal, e.g., a fluorescent molecule, a radioactive isotope, and/or an enzyme that can produce a color change in the presence of an appropriate substrate.

In some embodiments, the detectable label can be a PRR (e.g., a lectin molecule) conjugated with an enzyme (e.g., horseradish peroxidase). In these embodiments, a substrate specific for the enzyme is added for colorimetric quantification. For example, when the detectable agent is labeled with a HRP, TMB can be added for colorimetric quantification where optical density can be measured around 450 nm. In some embodiments, the detectable label can be a lectin labeled with HRP, e.g., FcMBL-HRP (FcMBL labeled with horseradish peroxidase (HRP)). In another embodiment, the detectable agent can be rhMBL-HRP (recombinant MBL labeled with HRP).

In addition to HRP labeling reagents, fluorescent labeling reagents such as FluoSpheres® (Life Technologies) and DyLight Fluor labeling reagents (Thermo Fisher) can also be used as a detectable label.

Samples Amenable to the Methods of Various Aspects Described Herein

Without limitations a sample for use in the various aspects disclosed herein can be a liquid, supercritical fluid, solutions, suspensions, gases, gels, slurries, and combinations thereof. The test sample or fluid can be aqueous or non-aqueous. In some embodiments, the sample can be an aqueous fluid. As used herein, the term "aqueous fluid" refers to any flowable water-containing material that is suspected of comprising a pathogen.

The sample can be collected from any source, including, e.g., human, animal, plants, environment, or organic or inorganic materials, suspected of being infected or contaminated by microbe(s).

In some embodiments, the sample can be a biological sample. As used herein, the term "biological sample" denotes all materials that are produced by biological organisms or can be isolated or obtained from them. The term "biological sample" includes untreated or pretreated samples. Pretreated biological samples can be, for example, heat treated (frozen, dried, etc.) or chemically treated (e.g., fixed in suitable chemicals such as formalin, alcohol, etc.)

In some embodiments, the biological sample can be a biological fluid. Exemplary biological fluids can include, but are not limited to, blood (including whole blood, plasma, cord blood and serum), lactation products (e.g., milk), amniotic fluids, sputum, saliva, urine, semen, joint fluid, cerebrospinal fluid, bronchial aspirate, perspiration, mucus, liquefied feces, synovial fluid, lymphatic fluid, tears, tracheal aspirate, and fractions thereof. In some embodiments, a biological fluid can include a homogenate of a tissue specimen (e.g., biopsy) from a subject. In some embodiments, a sample can comprises a suspension obtained from homogenization of a solid sample obtained from a solid organ or a fragment thereof.

In some embodiments of the methods disclosed herein, the method comprises obtaining a sample from the subject. Methods of obtaining a sample from a subject are well known in the art and easily available to one of skill in the art.

In some embodiments, the sample can include a fluid or specimen obtained from an environmental source, e.g., but not limited to, food products or industrial food products, food produce, poultry, meat, fish, beverages, dairy products, water supplies (including wastewater), surfaces, ponds, rivers, reservoirs, swimming pools, soils, food processing and/or packaging plants, agricultural places, hydrocultures (including hydroponic food farms), pharmaceutical manufacturing plants, animal colony facilities, and any combinations thereof.

In some embodiments, the sample can include a fluid (e.g., culture medium) from a biological culture. Examples of a fluid (e.g., culture medium) obtained from a biological culture includes the one obtained from culturing or fermentation, for example, of single- or multi-cell organisms, including prokaryotes (e.g., bacteria) and eukaryotes (e.g., animal cells, plant cells, yeasts, fungi), and including fractions thereof. In some embodiments, the test sample can include a fluid from a blood culture. In some embodiments, the culture medium can be obtained from any source, e.g., without limitations, research laboratories, pharmaceutical manufacturing plants, hydrocultures (e.g., hydroponic food farms), diagnostic testing facilities, clinical settings, and any combinations thereof.

In some embodiments, the test sample can be a non-biological fluid. As used herein, the term "non-biological fluid" refers to any fluid that is not a biological fluid as the term is defined herein.

In some embodiments, the test sample can include a media or reagent solution used in a laboratory or clinical setting, such as for biomedical and molecular biology applications. As used herein, the term "media" refers to a medium for maintaining a tissue, an organism, or a cell population, or refers to a medium for culturing a tissue, an organism, or a cell population, which contains nutrients that maintain viability of the tissue, organism, or cell population, and support proliferation and growth. As used herein, the term "reagent" refers to any solution used in a laboratory or clinical setting for biomedical and molecular biology applications. Reagents include, but are not limited to, saline solutions; PBS solutions; buffered solutions, such as phosphate buffers, EDTA, Tris solutions; and any combinations thereof.

Exemplary Microbes or Pathogens

As used herein, the term "microbes" or "microbe" generally refers to microorganism(s), including bacteria, virus, fungi, parasites, protozoan, archaea, protists, e.g., algae, and a combination thereof. The term "microbes" encompasses both live and dead microbes. The term "microbes" also includes pathogenic microbes or pathogens, e.g., bacteria causing diseases such as plague, tuberculosis and anthrax; protozoa causing diseases such as malaria, sleeping sickness and toxoplasmosis; fungi causing diseases such as ringworm, candidiasis or histoplasmosis; and bacteria causing diseases such as sepsis.

Microbe-induced diseases: In some embodiments, the following microbes that causes diseases and/or associated microbial matter can be amendable to the methods of various aspects described herein: *Bartonella henselae, Borrelia burgdorferi, Campylobacter jejuni*, Campylobacterfetus, *Chlamydia trachomatis, Chlamydia pneumoniae, Chylamydia psittaci, Simkania negevensis, Escherichia coli* (e.g., O157:H7 and K88), *Ehrlichia chafeensis, Clostridium botulinum, Clostridium perfringens, Clostridium tetani, Enterococcus faecalis, Haemophilius influenzae, Haemophilius ducreyi, Coccidioides immitis, Bordetella pertussis, Coxiella burnetii, Ureaplasma urealyticum, Mycoplasma genitalium, Trichomatis vaginalis, Helicobacter pylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacterium fortuitum, Mycobacterium genavense, Mycobacterium haemophilum, Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii*, Arcanobacterium *haemolyticum, Bacillus anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis, Treponema pallidum*, Human rhinovirus, Human coronavirus, Dengue virus, Filoviruses (e.g., Marburg and Ebola viruses), Hantavirus, Rift Valley virus, Hepatitis B, C, and E, Human Immunodeficiency Virus (e.g., HIV-1, HIV-2), HHV-8, Human papillomavirus, Herpes virus (e.g., HV-I and HV-II), Human T-cell lymphotrophic viruses (e.g., HTLV-I and HTLV-II), Bovine leukemia virus, Influenza virus, Guanarito virus, Lassa virus, Measles virus, Rubella virus, Mumps virus, Chickenpox (Varicella virus), Monkey pox, Epstein Bahr virus, Norwalk (and Norwalk-like) viruses, Rotavirus, Parvovirus B19, Hantaan virus, Sin Nombre virus, Venezuelan equine encephalitis, Sabia virus, West Nile virus, Yellow Fever virus, causative agents of transmissible spongiform encephalopathies, Creutzfeldt-Jakob disease agent, variant Creutzfeldt-Jakob disease agent, *Candida, Cryptcooccus, Cryptosporidium, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi*, among other viruses, bacteria, archaea, protozoa, and fungi. Microbes disclosed in the Examples are also amenable to the methods of various aspects described herein.

Military and bioterrorism applications: In yet other embodiments, bioterror agents (e.g., B. *Anthracis*, and smallpox) can be amendable to the methods of various aspects described herein.

Embodiments of various aspects described herein can be defined in any of the following numbered paragraphs:

1. A method of determining efficacy of an antimicrobial treatment regimen in a subject, the method comprising:
   (i) assaying at least one biological sample with a pattern recognition receptor (PRR)-based assay for the presence of microbe associated molecular patterns (MAMPs), wherein the biological sample is collected from the subject who has been administered the antimicrobial treatment for no longer than 24 hours;
   (ii) comparing the detectable signal level of MAMPs obtained from (i) to a baseline level; and
   (iii) identifying the antimicrobial treatment to be effective if a treatment related change in the detectable signal level relative to the baseline level is present; or identifying the antimicrobial treatment to be ineffective if the treatment related change in the detectable signal level relative to the baseline level is absent.
2. The method of paragraph 1, wherein the biological sample is collected from the subject who has been administered the antimicrobial treatment for no longer than 12 hour, no longer than 8 hours, no longer than 6 hours, no longer than 4 hours, no longer than 2 hours, no longer than 1 hour or less.
3. The method of paragraph 1 or 2, wherein the baseline corresponds to the level of MAMPs before the administration of the antimicrobial treatment.
4. The method of any of paragraphs 1-3, wherein the treatment related change is at least 1.5 fold from the baseline level.
5. The method of any of paragraphs 1-4, wherein when the subject has a high baseline of MAMP level, the antimicrobial treatment is identified to be effective if a treatment related decrease in the detectable signal level relative to the baseline level is present.
6. The method of paragraph 5, wherein the subject underwent an ineffective antimicrobial treatment before the onset of the present antimicrobial treatment.
7. The method of any of paragraphs 1-4, wherein when the subject has a low baseline of MAMP level, the antimicrobial treatment is identified to be effective if a treatment related increase in the detectable signal level related to the baseline level is present.
8. The method of paragraph 7, wherein the subject has an early diagnosis of an infection.
9. A method of determining efficacy of an antimicrobial treatment regimen in a subject, the method comprising:
   (i) assaying a biological sample for the presence of MAMPs with a PRR-based assay, wherein the biological sample is collected from the subject who has been administered the antimicrobial treatment for no longer than 24 hours;
   (ii) comparing the detectable signal level of MAMPs obtained from (i) to a baseline level; and
   (iii) identifying the antimicrobial treatment to be effective if a treatment related rate of change in the detectable signal level differs from the baseline level.

identifying the antimicrobial treatment to be ineffective if the treatment related rate of change in the detectable signal level does not differ from the baseline level.

10. The method of paragraph 9, wherein the treatment related rate of change in the detectable signal level is increased relative to the baseline level.

11. The method of paragraph 9, wherein the treatment related rate of change in the detectable signal level is decreased relative to the baseline level.

12. A method of diagnosing a microbial infection in a subject, the method comprising:
(i) assaying a biological sample from a subject for the presence of MAMPs with a PRR-based assay; and
(ii) comparing the detectable signal level of MAMPs obtained from (i) to a reference level; and
(iii) identifying the subject to be likely infected with at least one microbe if the detectable signal level of MAMPs is higher than the reference level; or
identifying the subject to be unlikely infected with microbes if the detectable signal level is not higher than the reference level.

13. The method of paragraph 12, wherein the method provides a diagnosis of the likelihood of the subject having a microbial infection in a shorter period of time than an assay in which whole microbes are detected.

14. The method of paragraph 12 or 13, wherein the reference level corresponds to the level of MAMPs in a non-infected subject.

15. The method of any of paragraphs 12-14, wherein the microbial infection signal or the detectable signal level of MAMPs is not induced by trauma.

16. The method of any of paragraphs 12-15, wherein said at least one microbe has a masking capsule (encapsulated)

17. The method of any of paragraphs 12-15, wherein said at least one microbe is non-capsulated.

18. The method of any of paragraphs 12-17, wherein said at least one microbe is selected from the genus of *Acineobacter, Aeromonas, Burkholderia, Candida, Citrobacter, Enterobacter, Enterococcus, Escherichia, Klebsiella, Morganella, Mycobacterium, Proteus, Providencia, Psuedomonas, Salmonella, Serratia, Shigella, Staphylococcus, Stenotrophomonas, Streptococcus, Yersinia*, or any combinations thereof.

19. The method of any of paragraphs 12-17, wherein said at least one microbe is resistant to at least one antimicrobial agent.

20. The method of any of paragraphs 12-19, further comprising administering an antimicrobial treatment to the subject.

21. The method of paragraph 20, further comprising identifying the microbe species or genus that is susceptible to the administered antimicrobial treatment if there is a treatment related change in the detectable signal level relative to a baseline level.

22. The method of paragraph 21, wherein the baseline level corresponds to a time point before the administration of the antimicrobial treatment.

23. The method of paragraph 21, wherein the baseline level corresponds to a time point after the administration of the antimicrobial treatment.

24. A method of screening for an antimicrobial agent comprising:
(a) contacting a sample comprising microbes with a candidate antimicrobial agent;
(b) subjecting the sample from (a) to a PRR-based assay for detecting release of microbe-associated molecular patterns (MAMPs) induced by the candidate antimicrobial agent; and
(c) identifying the candidate antimicrobial agent to be effective if the kinetics profile of the MAMP release indicates a change comprising an increase or decrease in a detectable signal, within a pre-determined period of time, relative to a baseline level upon the contact of the microbes with the candidate antimicrobial agent; or
identifying the candidate antimicrobial agent to be ineffective if the kinetics profile of the MAMP release does not indicate a change, within the pre-determined period of time, relative to the baseline level upon the contact of the microbes with the candidate antimicrobial agent.

25. A method of identifying an effective antimicrobial agent against a specific microbe comprising:
(a) contacting a sample infected with the specific microbe with a candidate antimicrobial agent;
(b) subjecting the sample from (a) to a PRR-based assay for detecting release of microbe-associated molecular patterns (MAMPs) induced by the candidate antimicrobial agent; and
(c) identifying the candidate antimicrobial agent to be effective if the kinetics profile of the MAMP release indicates a change comprising an increase or decrease in a detectable signal, within a pre-determined period of time, relative to a baseline level upon the contact of the specific microbe with the candidate antimicrobial agent; or identifying the candidate antimicrobial agent to be ineffective if the kinetics profile of the MAMP release does not indicate a change, within the pre-determined period of time, relative to the baseline level upon the contact of the specific microbe with the candidate antimicrobial agent.

26. The method of paragraph 24 or 25, wherein the sample is collected from a cell culture.

27. The method of paragraph 24 or 25, wherein the sample is collected from an animal model of an infection.

28. The method of any of paragraphs 1-27, wherein the PRR-based assay comprises binding of the MAMPs to a PRR-tethered surface or a PRR-coated solid substrate surface.

29. The method of paragraph 28, wherein the surface or solid substrate surface is a surface of a bead or particle (including microparticle and nanoparticle), a hollow fiber, a fiber, a porous solid substrate, a filter, a screen, a mesh, a tube, a scaffold, a plates, a channel, a gold particle, a magnetic material, a medical apparatus (e.g., needles or catheters) or implant, a dipsticks or test strip, a filtration devices or membrane, a hollow fiber cartridge, a microfluidic device, a mixing element (e.g., spiral mixers), a extracorporeal device, or any combinations thereof.

30. The method of any of paragraphs 1-29, wherein the PRR-based assay comprises detection of the MAMPs using a PRR molecule.

31. The method of paragraph 30, wherein the PRR molecule is the same molecules as tethered to the surface or coated onto the solid substrate surface.

32. The method of paragraph 30, wherein the PRR molecule is different from the PRR molecule tethered to the surface or coated onto the solid substrate surface.

33. The method of any of paragraphs 30-32, wherein the PRR molecule is tagged with detectable label.

34. The method of any of paragraph 33, wherein the detectable label comprises a reporter enzyme.

35. The method of any of paragraph 33, wherein the PRR based assay comprises detection of the MAMPs by enzyme linked lectin sorbent assay (ELLecSA).
36. The method of any of paragraphs 33-35, wherein the detectable label comprises a reporter fluorophore.
37. The method of any of paragraphs 1-29, wherein when the PRR-based assay comprises binding of the MAMPs to a PRR-coated bead or microparticle, the bound MAMPs are detected by an increase of phagocytosis when the PRR-coated bead or microparticle bound with the MAMPs is in contact with an immune cell.
38. The method of paragraph 37, wherein the immune cell is a THP-1.
39. The method of paragraph 37, wherein the immune cell is present in the subject's blood sample.
40. The method of any of paragraphs 37-39, wherein the PRR-coated bead or microparticle comprises a magnetic material.
41. The method of paragraph 40, wherein the immune cell phagocytizing the magnetic PRR-coated bead or microparticle bound with the MAMPs is separated from an immune cell without the magnetic PRR-coated bead or microparticle bound with the MAMPs by magnetic separation.
42. The method of any of paragraphs 1-36, wherein when the PRR-based assay comprises binding of the MAMPs to a PRR-coated bead or particle, the bound MAMPs are detected by detecting or quantifying the agglutination (crosslinking) of the beads or particles that are bound with the MAMPs.
43. The method of any of paragraphs 1-36, wherein when the PRR-based assay comprises binding of the MAMPs to the PRR-tethered surface or the PRR-coated solid substrate surface, the bound MAMPs are detected by surface plasmon resonance, polymerase chain reaction, mass spectrometric methods, sequencing, and any combinations thereof.
44. The method of any of paragraphs 1-36, wherein when the PRR-based assay comprises binding of the MAMPs to a PRR-coated bead or particle, the bound MAMPs are detected by an engineered reporter cell.
45. The method of paragraph 44, wherein the engineered reporter cell is place in a microfluidic device.
46. The method of any of paragraphs 1-45, wherein the baseline level is a level of at least one MAMP before the onset of the antimicrobial treatment.
47. The method of any of paragraphs 1-46, wherein the baseline level is a level of at least one MAMP subsequent to the onset of the antimicrobial treatment.
48. The method of any of paragraphs 1-47, wherein the PRR based assay comprises assaying two or more biological samples obtained at different times (e.g., from the subject) after administering of the antimicrobial treatment.
49. A method of enhancing microbe detection in a sample by FcMBL based microbe capture/detection assay, the method comprising pre-treating the sample to lyse or kill the microbe before assaying with the FcMBL based assay.
50. The method of paragraph 49, wherein said pre-treatment is physical, mechanical, chemical, biological, or any combinations thereof.
51. The method of paragraph 49 or 50, wherein said pre-treatment comprises incubating the sample with an antimicrobial agent.
52. The method of any of paragraphs 49-51, wherein said pre-treatment comprises sonication; agitation; vortexing; milling including beadmilling, grinding, french press, cryofracture; and any combinations thereof.
53. A method of determining efficacy of an antimicrobial treatment regimen in a subject, the method comprising:
(i) providing a biological sample from a subject, wherein the subject is administered an antimicrobial treatment;
(ii) assaying the biological sample with a FcMBL based microbe capture/detection assay for at least one component derived from, originated from, or secreted from a microbe, wherein an increase in level of the at least one component in the biological sample relative to a baseline level indicates said antimicrobial treatment regimen is effective.
54. A method of diagnosing an infection in a subject, the method comprising:
(i) providing a biological sample from a subject, wherein the subject is administered an antimicrobial treatment;
(ii) assaying the biological sample with a FcMBL based microbe capture/detection assay for at least one component derived from, originated from, or secreted from a microbe, wherein an increase in level of the at least one component in the biological sample relative to a baseline level indicates infection with a microbe susceptible to the antimicrobial treatment.
55. A method of adapting an antimicrobial treatment regime in a subject, the method comprising:
(i) providing a first biological sample from a subject, wherein the subject is administered a broad spectrum antimicrobial treatment;
(ii) assaying the first biological sample with a FcMBL based microbe capture/detection assay for at least one component derived from, originated from, or secreted from a microbe;
(iii) administering a first narrow spectrum antimicrobial treatment to the subject if assaying in step (ii) shows an increase in level of the at least one component in the biological sample relative to a baseline;
(iv) assaying a second biological sample with a FcMBL based microbe capture/detection assay, wherein the second biological assay is obtained from the subject after administering of the first narrow spectrum antimicrobial treatment;
(v) administering a second narrow spectrum antimicrobial treatment to the subject if assaying in step (iv) shows little or no change in level of the at least one component in the second biological sample relative to the baseline;
(vi) assaying a third biological sample with a FcMBL based microbe capture/detection assay, wherein the third biological assay is obtained from the subject after administering of the second narrow spectrum antimicrobial treatment;
(vii) repeating steps (v) and (vi) with a different second narrow spectrum antimicrobial treatment until the assay of step (vi)) shows an increase in level of the at least one component in the third biological sample relative to a baseline.
56. A method of monitoring in vivo activity of an antimicrobial agent in a subject suspected of having an infection, the method comprising:
(i) providing a biological sample from a subject, wherein the subject is undergoing or had previously undergone an antimicrobial treatment with the antimicrobial agent;
(ii) assaying the biological sample for at least one component derived from, originated from, or secreted from a microbe, said assay comprising a FcMBL based microbe capture/detection assay,
wherein an initial increase followed by a decrease over a period of time in level of the at least one component in the biological sample relative to a baseline level indicates the antimicrobial agent is active against the suspected infection.

57. The method of any of paragraphs 53-56, wherein said baseline level of the at least one component is a level before onset of said antimicrobial treatment.

58. The method of any of paragraphs 53-57, wherein said assay step comprises assaying two or more biological samples obtained at different times from the subject after administering of the antimicrobial treatment.

59. The method of any of paragraphs 53-58, wherein said increase in level is a spike in the level.

60. The method of any of paragraphs 53-59, wherein said FcMBL based assay is ELISA.

61. A method of adapting an antimicrobial treatment regimen in a subject, the method comprising:
(i) providing a first biological sample from a subject, wherein the subject is administered an antimicrobial treatment, wherein the antimicrobial treatment is presumed to be ineffective;
(ii) assaying the first biological sample with a PRR based MAMP capture/detection assay for at least one MAMP derived from, originated from, or secreted from a microbe;
(iii) administering a first antimicrobial treatment with a different spectrum from the one previously ineffective to the subject if assaying in step (ii) shows little or no change in level of the at least one MAMP in the biological sample relative to a baseline;
(iv) assaying a second biological sample with a PRR based microbe capture/detection assay, wherein the second biological assay is obtained from the subject after administering of the first different antimicrobial treatment in (iii);
(v) administering a second antimicrobial treatment different from the first antimicrobial treatment to the subject if assaying in step (iv) shows little or no change in level of the at least one MAMP in the second biological sample relative to the baseline;
(vi) assaying a third biological sample with a PRR based MAMP capture/detection assay, wherein the third biological assay is obtained from the subject after administering of the second different antimicrobial treatment in (v);
(vii) repeating steps (v) and (vi) with a different antimicrobial treatment until the assay of step (vi) shows a change (e.g., an increase or decrease) in level of the at least one MAMP in the third biological sample relative to a baseline.

62. A method of monitoring in vivo activity of an antimicrobial agent in a subject suspected of having an infection, the method comprising:
(i) providing a biological sample from a subject, wherein the subject is undergoing or had previously undergone an antimicrobial treatment with the antimicrobial agent;
(ii) assaying the biological sample for at least one MAMP, said assay comprising a PRR based MAMP capture/detection assay,
wherein an initial increase followed by a decrease over a period of time in level of the at least one MAMP (as determined by the assay signal) in the biological sample relative to a baseline level indicates the antimicrobial agent is active against the suspected infection.

63. The method of any of paragraphs 61-62, wherein said baseline level of the at least one component is a level before onset of said antimicrobial treatment.

64. The method of any of paragraphs 61-63, wherein said baseline level is a level subsequent to the onset of antimicrobial treatment.

65. The method of any of paragraphs 61-64, wherein said assay step comprises assaying two or more biological samples obtained at different times from the subject after administering of the antimicrobial treatment.

66. The method of any of paragraphs 61-65, wherein said increase in level is a spike in the level.

67. The method of any of paragraphs 61-66, wherein the decrease is the decrease in level of the spike.

68. The method of any of paragraphs 61-67, wherein said PRR based assay is ELLecSA.

69. A method of enhancing detection of a microbe in a sample by a pattern recognition receptor (PRR)-based microbe capture/detection assay, the method comprising pre-treating the sample to lyse or kill the microbe, and assaying the pre-treated sample for the presence of microbe associated molecular patterns (MAMPs) with a PRR-based assay.

70. The method of paragraph 69, wherein the microbe has a masking capsule.

71. The method of paragraph 70, wherein the microbe is selected from the group consisting of *Acineobacter, Aeromonas, Burkholderia, Candida, Citrobacter, Enterobacter, Enterococcus, Escherichia, Klebsiella, Morganella, Mycobacterium, Proteus, Providencia, Psuedomonas, Salmonella, Serratia, Shigella, Staphylococcus, Stenotrophomonas, Streptococcus, Yersinia, Klebsiella oxytoca, E. aeorgenes, E. cloacae, S. typhimurium, Acinetobacter, L. monocytogenes, K pneumoniae, S. epidermidis, S. paratyphi*, any microbes listed in Table 1, Table 2A, and Table 3, and any combinations thereof.

72. The method of paragraph 70 or 71, wherein the method expands the microbial detection spectrum of the PRR-based assay.

73. The method of any of paragraphs 69-72, wherein said pre-treatment comprises sonication; agitation; vortexing; milling including beadmilling, grinding, french press, cryofracture; and any combinations thereof.

74. The method of any of paragraphs 69-73, wherein the MAMPs comprise lipopolysaccharide (LPS).

75. The method of any of paragraphs 69-74, wherein the PRR-based assay is a lectin based assay.

76. The method of paragraph 75, wherein the lectin based assay comprises enzyme-linked lectin sorbent assay (EL-LecSA).

77. The method of paragraph 76, wherein the ELLecSA is FcMBL ELLEcSA.

78. A method of determining efficacy of an antimicrobial treatment regimen in a subject, the method comprising:
(i) assaying a biological sample from a subject who is administered an antimicrobial treatment for the presence of MAMPs with a PRR-based assay;
(ii) comparing the detectable signal level of MAMPs obtained from (i) to a baseline level; and
(iii) identifying the antimicrobial treatment to be effective if a treatment related increase or spike in the detectable signal level relative to a baseline level is present; or identifying the antimicrobial treatment to be ineffective if the treatment related increase or spike in the detectable signal level relative to the baseline level is absent.

79. A method of diagnosing an infection in a subject, the method comprising:
(i) assaying a biological sample from a subject who is administered an antimicrobial treatment for the presence of MAMPs with a PRR-based assay;

(ii) comparing the detectable signal level of MAMPs obtained from (i) to a baseline level; and
(iii) identifying the microbe species or genus that is susceptible to the administered antimicrobial treatment if a treatment related increase or spike in the detectable signal level relative to a baseline level; or
performing an additional assay and/or administering to the subject with a different antimicrobial treatment if the treatment related increase or spike in the detectable signal level relative to the baseline level is absent.

80. A method of optimizing an antimicrobial treatment regime in a subject, the method comprising:
(i) assaying a biological sample from a subject administered with a first antimicrobial treatment, for the presence of MAMPs with a PRR-based assay;
(ii) comparing the detectable signal level of MAMPs obtained from (i) to a baseline level; and
(iii) continuing administration of the first antimicrobial treatment if a treatment related increase or spike in the detectable signal level relative to the baseline level is present; or administering a second antimicrobial treatment to the subject if the treatment related increase or spike in the detectable signal level relative to the baseline level is absent.

81. The method of paragraph 80, wherein when the second antimicrobial treatment is administered to the subject, the method further comprises repeating steps (i)-(iii) until a treatment related increase or spike in the detectable signal level relative to the baseline level is present.

82. A method of monitoring in vivo activity of an antimicrobial agent in a subject suspected of having an infection, the method comprising:
(i) assaying a biological sample from a subject who is undergoing or was administered previously with the antimicrobial agent, for the presence of MAMPs with a PRR-based assay;
(ii) comparing the detectable signal level of MAMPs obtained from (i) to a baseline level; and
(iii) identifying the antimicrobial agent as active against the suspected infection if there is a change in level of at least one of the MAMPs relative to the baseline level; or identifying the antimicrobial agent as inactive against the suspected infection if the initial increase or the decrease is absent.

83. The method of any of paragraphs 78-82, wherein said baseline level of said at least one of the MAMPs is a level before onset of said antimicrobial treatment.

84. The method of any of paragraphs 78-83, wherein said baseline level of said at least one of the MAMPs is a level at a first time point after the onset of said antimicrobial treatment, wherein the first time point is before the time point when the biological sample was obtained.

85. The method of any of paragraphs 69-84, wherein said PRR-based assay comprises assaying two or more biological samples obtained at different times from the subject after administering of the antimicrobial treatment.

86. The method of any of paragraphs 82-85, wherein said change in level is an increase in level.

87. The method of any of paragraphs 82-86, wherein said change in level is a decrease in level.

88. The method of any of paragraphs 69-87, wherein the MAMPs comprise lipopolysaccharide (LPS).

89. The method of any of paragraphs 69-88, wherein the PRR-based assay is a lectin based assay.

90. The method of paragraph 89, wherein the lectin based assay comprises enzyme-linked lectin sorbent assay (ELLecSA).

91. The method of paragraph 90, wherein the ELLecSA is FcMBL ELLEcSA.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

In one aspect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "increased", "increase" or "enhance" are all used herein to generally mean an increase by a statically significant amount; for the avoidance of any doubt, the terms "increased", "increase" or "enhance" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein and throughout the specification, the terms "administering," or "administration" refer to the placement of an agent (e.g., an antimicrobial agent) into a subject by a method or route which results in at least partial localization of such agents at a desired site, such as a site of infection, such that a desired effect(s) is produced. Examples of administration routes can include, but are not limited to, oral administration and parenteral administration. The phrase "parenteral administration" as used herein refers to modes of administration other than enteral and topical administration, usually by injection.

As used herein and throughout the specification, the terms "treat," "treatment," "treating," refer to therapeutic treatments, wherein the object is to reverse, alleviate, ameliorate, inhibit, slow down or stop the progression or severity of a condition associated with a disease or disorder. The term "treating" or "treatment" includes reducing or alleviating at least one adverse effect or symptom of a condition, disease or disorder, such as microbial infection. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female. Additionally, a subject can be an infant or a child.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with auto-immune disease or inflammation. In addition, the methods and compositions described herein can be used for domesticated animals and/or pets. A human subject can be of any age, gender, race or ethnic group, e.g., Caucasian (white), Asian, African, black, African American, African European, Hispanic, Mideastern, etc. . . . . In some embodiments, the subject can be a patient or other subject in a clinical setting. In some embodiments, the subject can already be undergoing antimicrobial treatment. In some embodiments, the subjected can be a subject suspected of having an infection. In some embodiments, the subject can be subject in need of diagnosis for infection.

The disclosure is further illustrated by the following examples which should not be construed as limiting. The examples are illustrative only, and are not intended to limit, in any manner, any of the aspects described herein. Further, various changes and modifications to the disclosed embodiments, which will be apparent to those of skill in the art, can be made without departing from the spirit and scope of the present invention. The following examples do not in any way limit the invention.

EXAMPLES

Example 1. An Ultra-Rapid, High Sensitivity, Sepsis Diagnostic

To develop an "Ultra-Rapid, High Sensitivity, Sepsis Diagnostic," a previously-developed genetically engineered version of the natural human opsonin—Mannose Binding Lectin (MBL) can be employed. See, e.g., International Appl. Nos. PCT/US2011/021603 filed Jan. 19, 2011 and PCT/US2012/047201 filed Jul. 18, 2012, the content of each of which is incorporated herein by reference in its entirety, for description of the genetically engineered versions of the natural human MBL, e.g., MBL fusion proteins such as FcMBL. Both the natural molecule and the engineered version bind to microbial cell wall molecules (e.g., branched high mannose oligosaccharides) that are found on a wide variety of different Gram positive and negative bacteria, fungi and parasites (>90 targets identified so far) but not to mammalian cells (3). This is in contrast to other pathogen capture and identification approaches that rely on use of ligands (e.g., antibodies, synthetic chemicals) that bind to a microbe-specific target. Thus, MBL molecules (natural or engineered) can be used to bind and capture pathogens that cause sepsis from blood samples, without having to first identify the pathogen type. Moreover, in accordance with some embodiments of various aspects described herein, MBL can bind both live pathogens and microbial compounds released upon pathogens lysis, which permits detection of infection even when cultures are negative.

The natural Mannose Binding Lectin (MBL) is a highly conserved component of the innate immune system that is capable of binding microbial carbohydrate moieties and target complement activation and phagocytosis of its substrate. MBL is a complex 18-mer "tulip bundle" protein with collagen-like stems connecting via a neck to a carbohydrate binding domain (CRD) that recognizes a broad range of pathogens including major bacteria, viruses such as CMV, Ebola, HIV, HSV, HBV, H5N1 or Marburg, fungi, protozoa and helminths as well as toxins.

One of the potential limitations of the use of natural human MBL is that it can activate complement through the lectin pathway and coagulation through a thrombin-like function. Therefore, a genetically engineered MBL (termed as FcMBL herein) was developed, for example, including removal of the sequences responsible for complement activation and coagulation, and fusion of the MBL carbohydrate binding domains (optionally including the neck region) to the Fc domain of IgG1 (e.g., human IgG1), which can greatly increase the efficiency of its expression and purification. In addition, the FcMBL is modified with a C-terminal amino-oxy-biotin (AOB) that provides biotinylation sites at the N-terminal portion (Alanine-Lysine-Threonine, AKT) of FcMBL, and thus allows orientated attachment to a solid substrate (e.g., superparamagnetic beads). In one embodiment, AOB-AKT-FcMBL has a single biotinylation site at the N-terminal portion (e.g., AKT) of FcMBL. When bound to the beads, FcMBL can be oriented radially, with MBL component pointed outward from beads. The labeling of FcMBL with biotin provides a capability of immobilizing the FcMBL onto the surfaces of streptavidin-coated substrate, e.g., superparamagnetic beads, in its correct orientation, resulting in coverage with a high density of closely packed, multivalent, carbohydrate recognition domains of MBL that are responsible for its naturally high avidity. As shown below, FcMBL can retain the same broad binding specificity as native MBL, but with higher efficiencies when immobilized on ~128 nm magnetic beads (Adamtech). FcMBL can bind at least 30 species of highly clinically relevant bacteria (e.g. but not limited to Gram positive bacteria such as *Staphylococcus aureus* including MRSA, *Streptococcus pyogenes, Clostridium* sp.; Gram negative bacteria such as *Pseudomonas aeruginosa, Escherichia coli, Klebsiella* sp., and fungi such as *Candida, Aspergillus*), in addition to molecular toxins that can be relevant to detection of sepsis—Lipopolysaccharide (bacterial endotoxin) when assessed in vitro. The FcMBL magnetic beads were also used in combination with a biospleen blood cleansing device, for example, as described in International Application No. PCT/US2012/031864 filed Apr. 2, 2012 and PCT/US2011/021718 filed Jan. 19, 2011, the contents of which are incorporated herein by reference, to detect in vivo different clinically relevant bacteria in at least three different rat sepsis models (caused by injection of *S. aureus*, LPS-endotoxin or a complex mixture of cecal contents)(6).

Development of an FcMBL ELLecSA assay: To evaluate the binding efficacy of FcMBL, a magnetic bead-based ELLecSA assay using a ~1 μm superparamagnetic bead (Dynal) coated with FcMBL was developed. The magnetic FcMBL beads and/or the process of magnetic bead-based ELLecSA assay (FIG. 1) are also described in the International Appl. Nos. PCT/US2011/021603 filed Jan. 19, 2011 and PCT/US2012/047201 filed Jul. 18, 2012, the contents of which are incorporated herein by reference in their entireties. In one embodiment, a ~200 μl of blood sample (or ~100 μl of a buffered sample) can be mixed with about 5 μl of FcMBL magnetic beads and diluted with TBS-Tween containing about 5 mM calcium ($Ca^{2+}$), ~4 mg/ml Heparin and a blocking agent (e.g., ~10 mM glucose) (final concentrations). Samples are incubated and agitated (e.g., on a benchtop shaker) for about 20 min at ~950 rpm at room temperature. Then, the FcMBL magnetic beads are separated from the sample for analysis, for example, by loading the sample onto a Kingfisher instrument for magnetic separation, automated washing and processing of the magnetic beads. The microbial components or microbial matter bound to the FcMBL bead can be detected by any methods known in art, e.g., but not limited to ELISA such as a sandwich assay using horseradish peroxidase-labeled recombinant human MBL (rhMBL) and the Pierce 1-Step TMB Substrate (Thermo Scientific), which can be read at 450 nm after addition of a sulphuric acid stop solution. This ELLecSA assay is designed so that it can be easily integrated into any conventional clinical microbiological laboratory in which commercial ELISA assays are commonly carried out on a daily basis.

Figure 1:
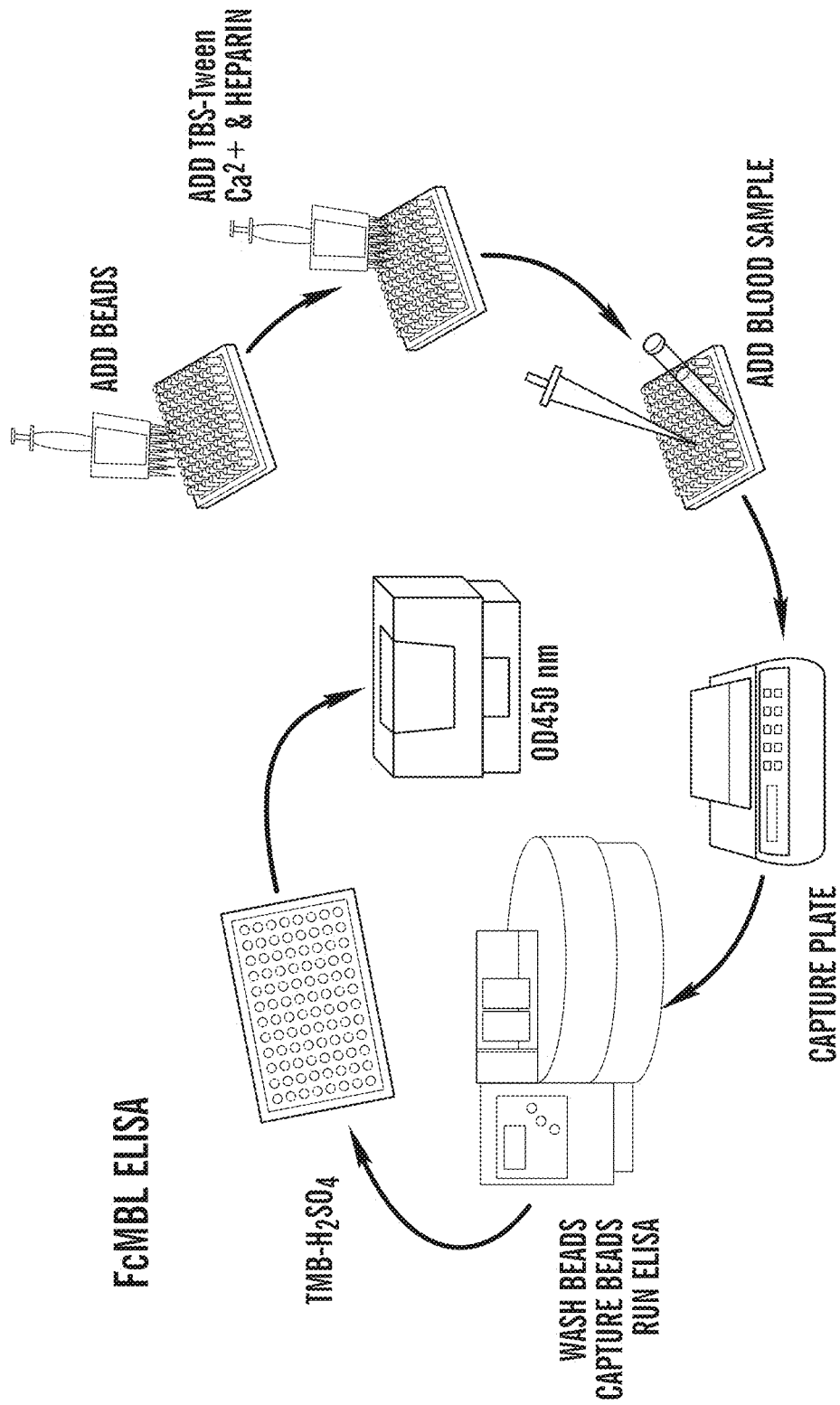
FIG. 1 outlines the workflow of FcMBL ELLecSA. First, 100 µL of sample is added to desired well of 96-well plate containing FcMBL-coated beads, buffer, and FBS. The material is captured for 20 min by shaking. After capture, the beads are washed using a KingFisher magnetic bead handling automation and captured microbial compounds are detected using HRP-labeled MBL. TMB is added for colorimetric quantification and optical density is measured at 450 nm. In this embodiment, at least 40 different samples can be measured in duplicate and compared with a mannan standard curve. Each assay can take about 52 minutes.

Using the FcMBL ELLecSA assay as shown in FIG. 1, inventors can rapidly (<1 hr) and reliably detect the presence of different intact microbes and/or MAMPs, e.g., mannan surface carbohydrates isolated from *Saccharomyces cerevisiae* (FIG. 2A), LPS-endotoxin from *E. coli* (FIG. 2B), and lipoarabinomannan and PIM6 from *Mycobacterium tuberculosis* (FIG. 3D), as well as multiple living pathogens, including *E. coli* (FIG. 2C), *Pseudomonas aeruginosa, Staphylococcus aureus, Mycobacterium tuberculosis* and *Candida albicans*.

The ELLecSA was validated using mannan, the prototypic MBL ligand. This assay was determined to have a detection range of 200 pg/ml mannan in buffer and to be remarkably effective in a variety of biological matrices such as blood, plasma or serum (e.g., FIG. 13A and FIG. 15B). FIGS. 13A and 15B show the detection of mannan by the ELLecSA using FcMBL coated beads and detected by rhMBL hrp. FIG. 13B shows the detection of LPS by the ELLecSA using FcMBL coated beads, with a detection limit range of 7-15 ng/mL, in TBST-Ca++. Other PRR coated beads, such as CRP, are able to detect pathogen associated molecular patterns (MAMPs) such as phosphocholin, LPS and Mannan using the ELLecSA. FIG. 13D shows CRP coated beads binding titers of *Enterococcus faecalis*.

Figure 2A:
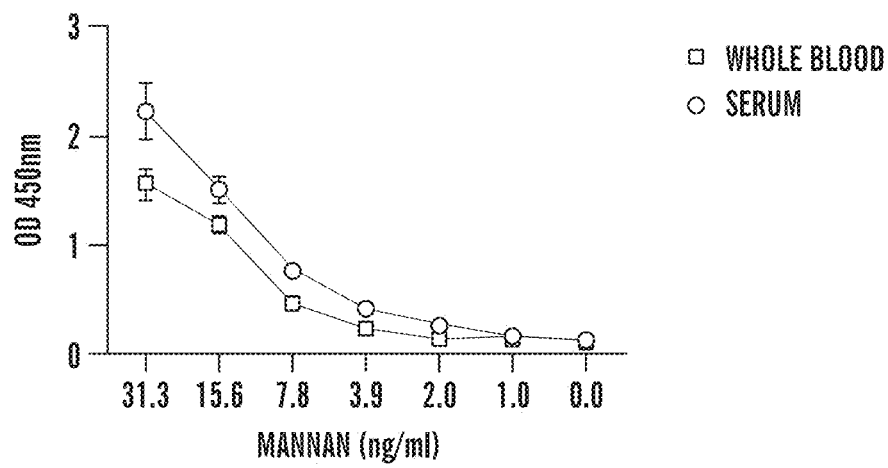
FIGS. 2A-2C show that FcMBL ELLecSA can detect bacterial and/or bacterial antigens in biological fluids. For example, FcMBL ELLecSA can detect mannan, lipopolysaccharide (LPS), and *E. coli* in serum and blood. Serial dilutions of mannan (FIG. 2A), LPS from *E. coli* O111:B4 (FIG. 2B) or *E. coli* (FIG. 2C) were spiked into either serum or whole EDTA blood, captured by FcMBL-coated superparamagnetic beads and detected by FcMBL ELLecSA. Biotin blocked beads were used as negative capture controls and anti-LPS immunoassay as positive control for LPS capture (data not shown).
Figure 2B:
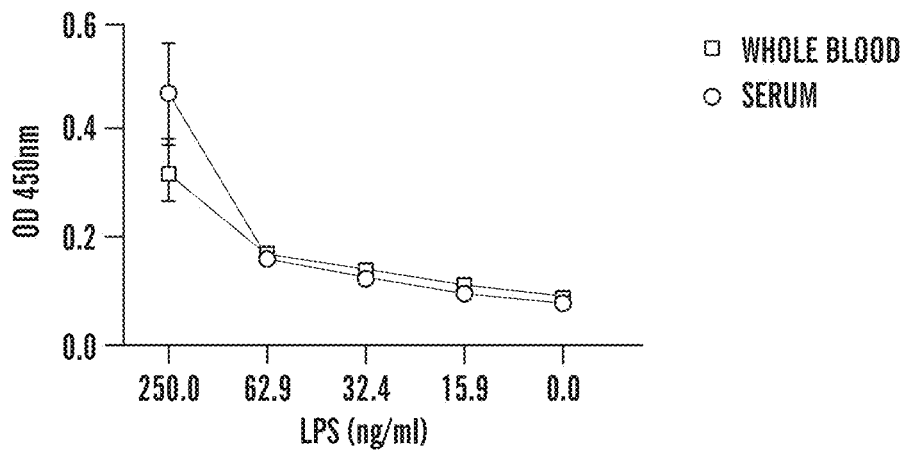
Figure 2C:
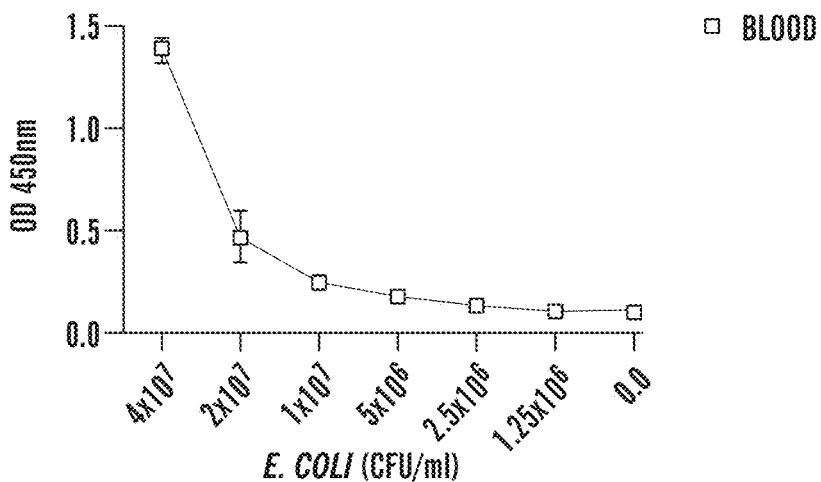
Figure 3B:
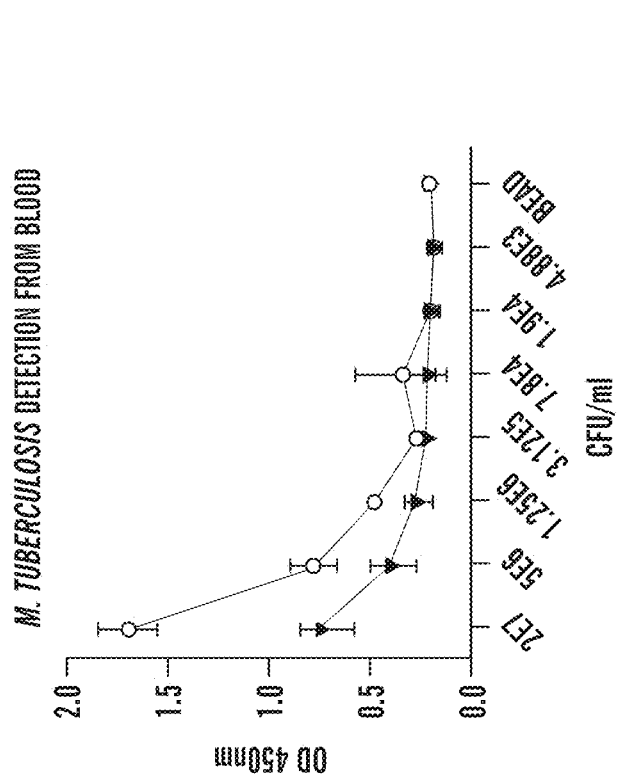
FIGS. 3A-3D show that FcMBL captures and detects *M. tuberculosis* via the cell wall antigens in a calcium dependent manner. Serial dilutions of *M. tuberculosis* irradiated strains H37Rv and HN878 were spiked into serum (FBS-TBST Ca++5 mM) (FIG. 3A) or whole EDTA blood (FIG. 3B), captured by FcMBL-coated superparamagnetic beads and detected by ELLecSA. Specificity of FcMBL detection and capture was determined by repeating capture of H37Rv with either FcMBL-coated beads in EDTA buffer (Ca++ free) or with biotin blocked beads in TBST Ca++5 mM (FIG. 3C). Serial dilutions of *M. tuberculosis* mannosylated cell wall antigens [Lipoarabinomannan (LAM), Phosphatidylinositol Mannosides (PIM 1, 2 and PIM 6)] were screened for binding and detection by FcMBL capture and ELLecSA (FIG. 3D).
Figure 3A:
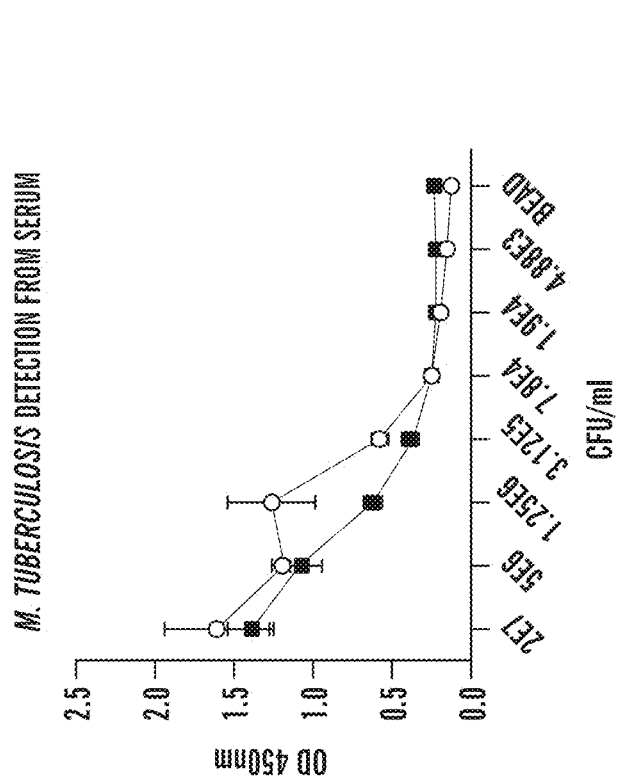
Figure 3D:
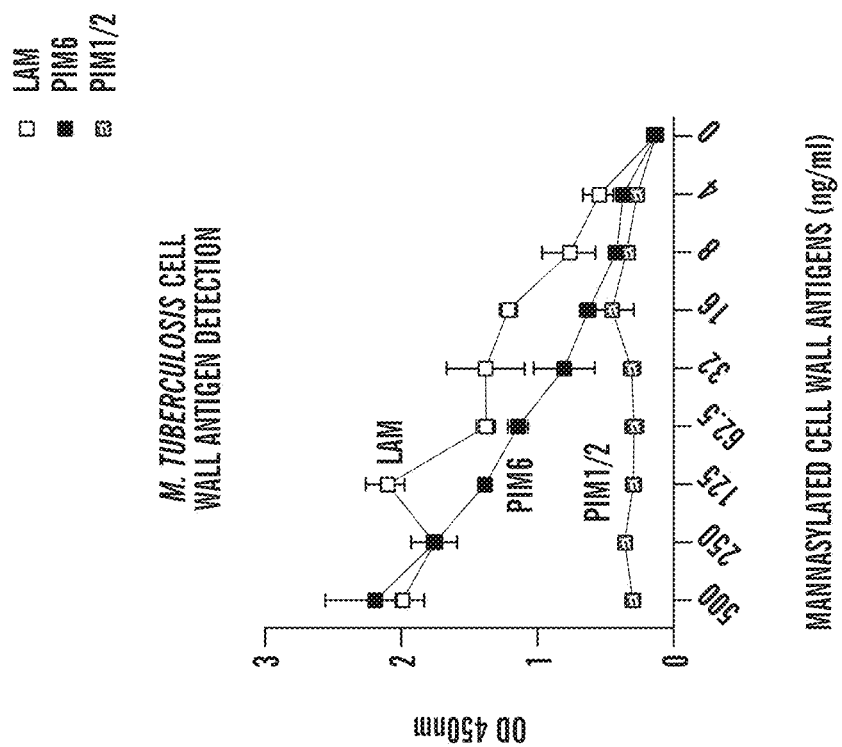

Without wishing to be bound by theory, the binding is mediated by calcium-dependent MBL as it can be inhibited by addition of EDTA or high concentrations of mannose. In addition, the presence of whole blood did not impair detection of intact microbes and/or MAMPs (FIGS. 2A-2C).

Further, clinical isolates of 33 different relevant pathogens were assessed using the FcMBL ELLecSA. When these pathogens were mechanically lysed (e.g., by sonication) to mimic the presence of dead pathogens or their debris as might occur in vivo, for example, due to antibiotic therapy or immune responses, the detection sensitivity was increased to 78% (59 of 75 isolates) over detection of live clinical isolates. See Table 1 for a list of microbes releasing MAMPs (e.g., produced by mechanical lysis such as sonication) detected by FcMBL ELLecSA or CRP ELLecSA. An even greater increase in detection sensitivity was detected when pathogens were killed in vitro using bactericidal antibiotics (e.g., Cefepime+Gentamycin) as compared to mechanical lysis produced by, e.g., bead milling, regardless of whether it was measured in buffer or in blood (FIGS. 4A-4B).

TABLE 1

List of microbes assessed by FcMBL ELLecSA and CRP ELLecSA. Positive signal is indicated by H (strong signal) or L (weak signal). Negative binders (no binding detected) indicated by N (negative). Microbes are grown in a cell cultured medium containing a blocking agent (e.g., RPMI media supplemented with 10% glucose) to 0.5 MacFarland (~$10^8$ CFU/ml). About 1 ml of bacteria are sonicated (100% pulse 5 min) then beadmilled for 7 mins. Serial dilutions are used for the ELLecSA. The term "BSE" in the table corresponds to beadmill or antibiotic treated sample ELLecSA." The term "WBE" in the table corresponds to whole bug or microbe ELLecSA.

| Genus | Species | Isolate | WBE High/Low/No | BSE High/Low/No |
|---|---|---|---|---|
| *Acinetobacter* | *baumannii* | BD | N | N |
| *Acinetobacter* | 1 | Crimson | N | N |
| *Acinetobacter* | 2 | Crimson | L | N |
| *Aeromonas* | *sobria* | Crimson | H | L |
| *Burkholderia* | *cepacia* | Crimson | L | L |

TABLE 1-continued

List of microbes assessed by FcMBL ELLecSA and CRP ELLecSA. Positive signal is indicated by H (strong signal) or L (weak signal). Negative binders (no binding detected) indicated by N (negative). Microbes are grown in a cell cultured medium containing a blocking agent (e.g., RPMI media supplemented with 10% glucose) to 0.5 MacFarland (~$10^8$ CFU/ml). About 1 ml of bacteria are sonicated (100% pulse 5 min) then beadmilled for 7 mins. Serial dilutions are used for the ELLecSA. The term "BSE" in the table corresponds to beadmill or antibiotic treated sample ELLecSA." The term "WBE" in the table corresponds to whole bug or microbe ELLecSA.

| Genus | Species | Isolate | WBE High/Low/No | BSE High/Low/No |
|---|---|---|---|---|
| Candida | albicans | BCH 868 #2 | H | H |
| Citrobacter | | HER | H | L |
| Enterobacter | aerogenes | BD | H | H |
| Enterobacter | aerogenes | Crimson | L | L |
| Enterobacter | aerogenes | Crimson | N | L |
| Enterobacter | aerogenes | DAV | N | H |
| Enterobacter | cloacae | BCH 474 | L | H |
| Enterobacter | cloacae | BCH 474 | L | H |
| Enterobacter | cloacae | BD | N | H |
| Enterobacter | cloacae | CQI | L | H |
| Enterobacter | cloacae | Crimson | L | H |
| Enterobacter | cloacae | Crimson | L | L |
| Enterobacter | cloacae | DOS | L | L |
| Enterobacter | cloacae | EST | L | H |
| Enterobacter | cloacae | LAC | L | H |
| Enterococcus | faecalis | BCH 1580 | N | N |
| Enterococcus | faecalis | BD | N | N |
| Enterococcus | faecium | BD | N | N |
| Enterococcus | gallinarum | BCH 32 | N | N |
| Escherichia | coli | ATCC | H | H |
| Escherichia | coli | ATCC 8739 | H | H |
| Escherichia | coli | ATCC 8739 | H | H |
| Escherichia | coli | AUS | L | H |
| Escherichia | coli | BCH 2276 | H | H |
| Escherichia | coli | BD | N | H |
| Escherichia | coli | BEI 0157:H7 | H | H |
| Escherichia | coli | BIM | N | L |
| Escherichia | coli | BLA | N | L |
| Escherichia | coli | BUR | N | L |
| Escherichia | coli | EMK | N | L |
| Escherichia | coli | FAB | L | H |
| Escherichia | coli | HAW | H | H |
| Escherichia | coli | LAH | L | L |
| Escherichia | coli | MAD | N | N |
| Escherichia | coli | MHA | N | L |
| Escherichia | coli | POL | H | H |
| Escherichia | coli | REN | H | H |
| Klebsiella | oxytoca | BCH 1130 #1 | L | H |
| Klebsiella | oxytoca | BCH 1131 #2 | L | H |
| Klebsiella | oxytoca | Crimson | H | H |
| Klebsiella | oxytoca | LAF | N | H |
| Klebsiella | oxytoca | LEP | N | L |
| Klebsiella | oxytoca | POL | N | L |
| Klebsiella | pneumoniae | BCH 1434 B | H | H |
| Klebsiella | pneumoniae | BCH 631 | L | H |
| Klebsiella | pneumoniae | BCH 631 | H | H |
| Klebsiella | pneumoniae | BCH 631 #2 | H | H |
| Klebsiella | pneumoniae | BCH 704 #2 | L | H |
| Klebsiella | pneumoniae | BD | H | H |
| Klebsiella | pneumoniae | CHO | L | H |
| Klebsiella | pneumoniae | PAZ | L | H |
| Morganella | morganii | DAV | L | L |
| Mycobacterium | leprae | BEI 19326 | H | |
| Mycobacterium | leprae | BEI 19327 | L | |
| Mycobacterium | tuberculosis | BEI HN878 | H | H |
| Mycobacterium | tuberculosis | H37RV | H | H |
| Proteus | mirabilis | BD | N | N |
| Proteus | mirabilis | BES | N | N |
| Proteus | mirabilis | BOUL | N | N |
| Proteus | mirabilis | LEC | N | N |
| Proteus | mirabilis | LEC | N | N |
| Proteus | vulgaris | SAN | N | N |
| Providencia | rettgeri | MAT | N | N |
| Pseudomonas | aeruginosa | BD | H | H |
| Salmonella | enteriditis | MGH | L | H |
| Salmonella | enteriditis | MGH | N | H |
| Salmonella | paratyphi A | MGH | L | H |

TABLE 1-continued

List of microbes assessed by FcMBL ELLecSA and CRP ELLecSA. Positive signal is indicated by H (strong signal) or L (weak signal). Negative binders (no binding detected) indicated by N (negative). Microbes are grown in a cell cultured medium containing a blocking agent (e.g., RPMI media supplemented with 10% glucose) to 0.5 MacFarland (~10$^8$ CFU/ml). About 1 ml of bacteria are sonicated (100% pulse 5 min) then beadmilled for 7 mins. Serial dilutions are used for the ELLecSA. The term "BSE" in the table corresponds to beadmill or antibiotic treated sample ELLecSA." The term "WBE" in the table corresponds to whole bug or microbe ELLecSA.

| Genus | Species | Isolate | WBE High/Low/No | BSE High/Low/No |
|---|---|---|---|---|
| Salmonella | paratyphi A | MGH | N | H |
| Salmonella | typhimurium | BD | N | L |
| Salmonella | typhimurium | Crimson | L | H |
| Salmonella | typhimurium | MGH (LT18) | L | H |
| Salmonella | typhimurium | MGH (LT2) | N | H |
| Salmonella | typhimurium | MGH 14028 | L | H |
| Salmonella | typhimurium | MGH 14028 | L | H |
| Serratia | marcescens | BCH 1851 | N | L |
| Serratia | marcescens | BD | N | L |
| Serratia | marcescens | BOUM | L | N |
| Serratia | marcescens | CAS | N | N |
| Serratia | marcescens | MAR | H | N |
| Shigella | flexneri | Crimson | L | H |
| Staphylococcus | aureus | BCH 1211 | H | H |
| Staphylococcus | aureus | BCH 1365 B | L | L |
| Staphylococcus | aureus | BCH 615 | H | H |
| Staphylococcus | aureus | BCH 783 | H | H |
| Staphylococcus | aureus | BCH 793 #1 | N | L |
| Staphylococcus | aureus | BH 938 | H | L |
| Staphylococcus | aureus (MRSA) | BD | H | H |
| Staphylococcus | aureus (MRSA) | BD | H | H |
| Staphylococcus | aureus (MSSA) | BD | H | H |
| Staphylococcus | aureus (MSSA) | COM | | |
| Staphylococcus | aureus (MSSA) | MAR | H | H |
| Staphylococcus | aureus (MSSA) | RAN | H | |
| Staphylococcus | aureus (MSSA) | | N | N |
| Staphylococcus | capitis | JUA | N | L |
| Staphylococcus | epidermidis | BD | H | N |
| Staphylococcus | epidermidis | CAT | N | N |
| Staphylococcus | epidermidis | LAR | N | H |
| Staphylococcus | epidermidis | MAR | N | N |
| Staphylococcus | epidermidis | SAL | L | L |
| Staphylococcus | hominis | JOL | L | H |
| Staphylococcus | lugdunensis | BD | N | N |
| Staphylococcus | lugdunensis | HER | N | |
| Staphylococcus | lugdunensis | LAB | L | |
| Staphylococcus | lugdunensis | MAT | N | |
| Staphylococcus | lugdunensis | PER1 | N | |
| Staphylococcus | lugdunensis | PER2 | N | |
| Staphylococcus | simulans | DAV | L | N |
| Stenotrophomonas | maltophilia | BD | L | N |
| Streptococcus | agalactiae | BD | N | L |
| Streptococcus | Group B | Crimson | N | H |
| Streptococcus | mitis | BD | N | N |
| Streptococcus | pneumoniae | BCH 577 | H | N |
| Streptococcus | pneumoniae | BCH 577 | N | N |
| Streptococcus | pneumoniae | BD | N | N |
| Streptococcus | pneumoniae | Crimson | N | L |
| Streptococcus | pyogenes | Crimson | H | H |
| Streptococcus | viridans | BCH 1283 | L | H |
| Streptococcus | viridans | BCH 53 | H | H |
| Yersinia | pseudotuberculosis | BEI 2515 | L | H |
| Yersinia | pseudotuberculosis | BEI 2666 | L | H |
| Yersinia | pseudotuberculosis | BEI 2775 | N | H |
| Yersinia | pseudotuberculosis | BEI 2777 | L | H |
| Yersinia | pseudotuberculosis | BEI 2790 | N | H |
| Yersinia | pseudotuberculosis | BEI III P+ | L | H |

MBL can bind a great variety of microbes. CRP can also bind a variety of microbes, including both gram positive and gram negative microbes. Table 2A provides a list of example microbes bound by MBL and/or CRP.

| Bacteria | Clinical Isolates | | | | | | | |
|---|---|---|---|---|---|---|---|---|
| | Whole Bug | | Beadmill | | ABX | | Binding | |
| | FcMBL | CRP | FcMBL | CRP | FcMBL | CRP | FcMBL | CRP |
| *Acinetobacter baumanii* | N | N | N | N | YH | N | YES | NO |
| *Acinetobacter*-01 | YL | N | YL | N | YL | N | YES | NO |
| *Acinetobacter*-02 | YL | N | N | N | YH | YH | YES | YES |
| *Aeromonas sobria* | N | N | N | N | N | YH | NO | YES |
| *E. aerogenes* | N | YL | N | N | YL | YH | YES | YES |
| *E. aerogenes* | YH | N | YH | N | YH | YH | YES | YES |
| *E. cloacae* | N | YH | YL | YL | YH | YH | YES | YES |
| *E. cloacae* | N | N | YH | N | YH | YH | YES | YES |
| *E. coli* | N | YL | YL | N | N | YH | YES | YES |
| *E. coli* | N | YL | N | N | YL | YH | YES | YES |
| *E. faecalis* | N | YH | N | YH | N | YH | NO | YES |
| *E. faecium* | N | YH | N | YH | N | YH | NO | YES |
| *K. pneumoniae* | N | N | YL | N | N | N | YES | NO |
| *K. pneumoniae* | N | YL | N | N | YL | YL | YES | YES |
| *L. monocytpgenes* | YH | N | N | YH | YL | YH | YES | YES |
| MRSA | YH | YH | YH | YH | YH | YH | YES | YES |
| MRSA | YH | YH | YH | YH | YH | YH | YES | YES |
| MRSA | YH | YH | YH | YH | YH | YH | YES | YES |
| MSSA | YH | YH | YH | YH | YH | YH | YES | YES |
| *P. aeruginosa* | YL | N | YL | N | YL | N | YES | NO |
| *P. aeruginosa* | YH | YL | YH | YL | YH | YL | YES | YES |
| *P. mirabilis* | N | N | N | N | N | N | NO | NO |
| *S. agalactiae* | N | N | N | YH | YL | YL | YES | YES |
| *S. epidermidis* | N | N | N | YH | N | YL | YES | YES |
| *S. epidermidis* | N | N | N | N | N | N | NO | NO |
| *S. lugdunensis* | N | YH | N | YH | YL | YH | YES | YES |
| *S. lugdunensis* | N | N | N | YH | YL | N | YES | YES |
| *S. maltophilia* | N | N | N | N | N | N | NO | NO |
| *S. marcensens* | YL | YL | YH | YH | YH | YH | YES | YES |
| *S. mitis* | N | N | N | YH | YL | YL | YES | YES |
| *S. pneumoniae* | N | YH | N | YH | YL | YH | YES | YES |
| *S. typhimurium* | YL | N | YL | N | YL | YH | YES | YES |
| *S. typhimurium* | N | YL | N | N | N | YH | YES | YES |
| Strep Group. B | N | N | N | YH | N | N | NO | YES |

The ability of the ELLecSA to detect a broad range of pathogenic bacteria using FcMBL or wild-type (wt) CRP-coated beads was accessed. Pathogens could be stratified as high binders, low binders and non-binders based on the ELLecSA signal generated by serially diluted suspensions. As shown in Table 2A above, YH=Yes binding, at a high level; N=no binding; YL=yes binding at a low level.

Table 2B is a summary result showing that disruption of microbes can increase detection of microbes using a PRR for ELLecSA detection of MAMPs. The clinical *E. coli* isolates can be disrupted by either beadmill or antibiotic (ABX) treatment.

| | Clinical *E. coli* isolates | | |
|---|---|---|---|
| | Total Tested | Whole Bug Bound | Bead Mill/ABX |
| Number | 25 | 9 | 24 |
| Percent | 100 | 36 | 96 |

Further, the inventors tested about 140 bacterial isolates from 38 species, and showed that the methods described herein can beind 36 species, e.g., using FcMBL or CRP ELLecSA.

There are previous reports of wild type MBL binding being impaired by polysaccharidic capsules in the case of *Cryptococcus neoformans*. In order to determine if encapsulation precluded the attachment of FcMBL to the bacterial cell wall, the bacteria were processed using a beadmill to disrupt the cell wall structure and make underlying carbohydrates accessible to the carbohydrate recognition domain (CRD) or pattern recognition receptor (PRR). It was found that the detection of commonly encapsulated pathogens such as *Klebsiella* sp. and *Enterobacter aerogenes* is greatly increased with beadmilling. Some of the low binders generated a significantly higher signal and the detection spectrum of the assay was significantly expanded by mechanical disruption of the cells. Therefore, PRR-coated beads can be used to bind both whole/live pathogens and their associated MAMPs. Further, FIG. 13C shows ELLecSA detection of titers of intact/viable *S. aureus* and *E. coli*. Furthermore, CRP coated beads were also used to bind a wide variety of bacteria that are subsequently detected by the ELLecSA. FIG. 13D shows the ability of CRP coated beads to bind *Enterococcus faecalis*.

The innate immune system is geared to recognize pathogens by engaging Microbe Associated Molecular Patterns (MAMPs) with receptors called Pattern Recognition Receptors (PRRs). To escape detection and destruction by the innate immune system pathogens mask their signature molecular domains by presenting to the host molecular patterns associated with self. The synthesis of a capsule decorated with carbohydrates expressed by eukaryotic cells is one of the best known strategies to survive within a host.

The use of mechanical treatment (e.g., a beadmill) allows the disruption of the outer layers of the cell wall and exposes MAMPs that would be hidden in vivo to the innate immune system. The use of, e.g., ultrasound waves, also allows the fragmentation of bacteria and can release or expose MAMPs normally not presented to the PRRs. The use of enzymes cleaving some of the cell wall carbohydrates can also restore the detection of carbohydrates otherwise not recognized by PRRs. The treatment of microbes (e.g., bacteria) with enzymes such as lysozyme or lysostaphin can cause cell wall degradation and release or exposure of MAMPs otherwise unable to bind to the PRRs. Other enzymatic treatment can involve proteases, lipases such as phospholipases, neuraminidase, and/or sialidase, or any other enzyme modifying the presentation of any MAMP to any PRR leveraged for detection of the MAMP. For instance, MBL or recombinant human MBL or engineered FcMBL binds mannose containing carbohydrates such as the core of LPS, the Wall Teichoic Acid from *Staphylococcus aureus*, PIM6 or Mannose-capped LipoArabinoMannan from *M. tuberculosis* whereas CRP binds phosphocholine found in *Streptococcus pneumoniae*, (Brundish and Baddiley, "Pneumococcal C-substance, a ribitol teichoic acid containing choline phosphate" Biochem J. 1968 December, 110(3): 573-82), *Haemophilus influenzae* (Weiser et al., Decoration of lipopolysaccharide with phosphorylcholine: a phase-variable characteristic of *Haemophilus influenzae*" Infect Immun. 1997 March; 65(3): 943-950), *Pseudomonas aeruginosa*, *Neisseria meningitides* and *Neisseria gonorrhoeae* (Serino and Virji, "Phosphorylcholine decoration of lipopolysaccharide differentiates commensal Neisseriae from pathogenic strains: identification of licA-type genes in commensal Neisseriae" Mol Microbiol. 2000 March, 35(6): 1550-9), *Morganella morganii* (Potter, "Antigen-binding myeloma proteins in mice" Ann N Y Acad Sci. 1971 Dec. 31, 190: 306-21), and *Aspergillus fumigatus* (Volanakis, "Human C-reactive protein: expression, structure, and function, "Molecular Immunology" 2001, 38(2-3): 189-197). Other PRR can be equally leveraged to recognize MAMPs such as NODs or PGRP. The PRR binding profile of a microorganism can provide presumptive identification of the class of said pathogen.

Table 3 provides binding ability of various bacteria to FcMBL or wt CRP upon mechanical treatment (e.g., using a beadmill), chemical treatment (e.g., with antibiotics) or no treatment. Clinical isolates were assayed on the ELLecSA for binding as either whole/live microbes, beadmilled, or antibiotic treated. Whole/live microbes were grown to a 0.5 McFarland and captured by FcMBL or wt CRP as either whole or beadmilled or antibiotic treated (clinically relevant doses were used). YH=Yes binding, at a high level; N=no binding; YL=yes binding at a low level.

|  |  | Whole Bug | | Beadmill | | ABX | | BINDING? | |
|---|---|---|---|---|---|---|---|---|---|
|  |  | FcMBL | CRP | FcMBL | CRP | FcMBL | CRP | FcMBL | CRP |
| Crimson | Acinetobacter-02 | N | N | N | N | YH | YH | YES | YES |
| Crimson | E. coli | N | YL | YL | N | N | YH | YES | YES |
| Crimson | K. pneumoniae | N | N | YL | N | N | N | YES | NO |
| Crimson | L. monocytpgenes | YH | YL | N | YH | YL | YH | YES | YES |
| Crimson | MRSA | YH | YH | YH | YH | YH | YH | YES | YES |
| Crimson | P. aeruginosa | YL | N | YL | N | YL | N | YES | NO |
| Crimson | S. epidermidis | N | N | N | YH | N | YL | YES | YES |
| Crimson | S. lugdunensis | N | YH | N | YH | YL | YH | YES | YES |
| Crimson | S. typhimurium | YL | N | YL | N | YL | YH | YES | YES |
| Crimson | Strep Group. B | N | N | N | YH | N | N | NO | YES |
| Crimson | E. aerogenes | N | N | N | YL | YN | N | YES | YES |
| Crimson | MRSA | YH | YH | YH | YH | YH | YH | YES | YES |
| Crimson | E. cloacae | N | YH | YH | YL | YH | YH | YES | YES |
| Crimson | Acinetobacter-01 | YL | N | YL | N | YL | N | YES | NO |
| Crimson | Aeromonas sobria | N | N | N | N | N | YH | NO | YES |
| BD | E. cloacae | N | N | YL | YL | YH | YH | YES | YES |
| BD | MRSA | YH | YH | YH | YH | YH | YH | YES | YES |
| BD | E. aerogenes | YH | N | YH | YL | YH | YH | YES | YES |
| BD | S. typhimurium | N | YL | N | YL | YL | YH | YES | YES |
| BD | P. mirabilis | N | N | N | N | N | N | NO | NO |
| BD | E. faecium | YL | YH | YL | YH | YL | YH | YES | YES |
| BD | S. maltophilia | N | N | YL | N | N | N | YES | NO |
| BD | S. lugdunensis | N | N | N | YH | YL | H | YES | YES |
| BD | S. mitis | N | N | N | YH | YL | YL | YES | YES |
| BD | S. agalactiae | N | N | N | YH | N | N | NO | YES |
| BD | S. marcensens | YL | N | YH | YL | YL | YH | YES | YES |
| BD | S. epidermidis | N | N | N | N | N | N | NO | NO |
| BD | P. aeruginosa | YH | YL | YH | YL | YH | YL | YES | YES |
| BD | A. baumanii | N | N | N | N | YH | N | YES | NO |
| BD | S. pneumoniae | N | YH | N | YH | YL | YH | YES | YES |
| BD | E. coli | N | YL | N | N | YL | YH | YES | YES |
| BD | K. pneumoniae | YL | YL | N | N | N | YL | YES | YES |
| BD | E. faecalis | N | YH | N | YL | N | YHH | NO | YES |
| BD | MSSA | YH | YH | YH | YH | YH | YH | YES | YES |

This finding indicates that sustained release and accumulation of microbial materials in the bloodstream, either from systemic infection or by release from an occult nidus of infection, can represent novel biomarkers of early infection, which can be detected in small samples of blood using the FcMBL ELLecSA assay.

To show the ability of the FcMBL ELLecSA to detect early infection, results of a pilot institutional review board (IRB)-approved study involving 41 adult (>18 yrs) patients with unstable vital signs (heart rate >130; systolic blood pressure <90 mm Hg; respiratory rate >30; lactic acid level >4.0 mmol/L) of any etiology over a 1 month period in the emergency department of a hospital indicated that mean FcMBL ELLecSA levels were significantly higher in septic patients compared to other disease etiologies, and there appeared to be a trend towards higher levels in patients with clinical decompensation. In addition, 74% (14 of 19) of the patients who had sepsis clinically documented were identified using the FcMBL ELLecSA, even though few of these patients had a positive blood culture (See Table 4 below).

Table 4 shows data for a prospective study of ELLecSA as a Sepsis Diagnostic. About 74% of clinically determined sepsis patients are ELLecSA positive (only 20% of the patients were blood culture positive). IRB approved blood samples were collected and screened by FcMBL ELLecSA. Data was scored as +(OD450 nm 0.2-0.3), ++(OD450 nm 0.3-0.5), +++(OD450 nm>0.5) and −(OD450 nm<0.2).

range of about 15 ng/ml. While the LAL assay can detect picograms of LPS, it is extremely susceptible to interferences from blood products and proteins, and has not provided reliable results compared to ELLecSA, in part because the ELLecSA signal is generated independent of blood clot assays. Whole blood can be used for ELLecSA assay.

| Patient | FcMBL | CRP | Culture | Sepsis Syndrome (Draw) | SOFA (Draw) | SOFA (Max) |
|---|---|---|---|---|---|---|
| 813 | +++ | ND | − | Severe Sepsis | 3-Feb | 3 |
| 814 | ++ | ND | − | Severe Sepsis | 4 | 7 |
| 815 | − | ND | − | Severe Sepsis | 3 | 3 |
| 817 | ++ | − | − | Sepsis (shock) | February 2000 | 2 |
| 818 | − | − | − | Sepsis (shock) | 1-Feb | 2 |
| 819 | +++ | + | +S. epidermidis | Sepsis (shock) | 7 | 7 |
| 820 | ++ | − | − | Severe Sepsis | 8-Mar | 8 |
| 821 | + | + | − | Severe Sepsis | 2-Jun | 6 |
| 822 | − | − | +C. difficile | Severe Sepsis (no SIRS) | 2-Mar | 3 |
| 823 | + | + | − | Sepsis (shock) | 6 | 6 |
| 824 | − | − | − | Severe Sepsis | 1 | 1 |
| 825 | ++ | − | − | Infection, no SIRS | 1-Apr | 4 |
| 826 | + | − | − | Sepsis (shock-severe) | 5 | 5 |
| 827 | + | − | − | Septic Shock | 8 | 8 |
| 828 | − | − | +K. pneumoniae | Septic Shock | 9 | 18 |
| 829 | + | ++ | − | Septic Shock | 3 | 5 |
| 830 | +++ | + | Multiple | Sepsis (shock-severe) | 7-May | 7 |
| 831 | +++ | +++ | − | Septic Shock | May 2000 | 5 |
| 832 | + | − | − | Septic Shock | 0 | 5 |

Example 2. Use of the FcMBL Opsonin in Serological Detection of Infections Such as Sepsis The FcMBL opsonin can be used as the basis for development of an ultra-rapid (<1 hr) ELLecSA-based diagnostic for the serological detection of severe infections, including sepsis. To develop such diagnostic, for example, a binding spectrum of the FcMBL ELLecSA assay can be determined by detection of multiple clinically relevant bacterial and fungal strains when spiked into human blood. Based on FcMBL ELLecSA performed on clinical samples drawn from patients from target populations, Receiver Operator Characteristic curves can be generated, from which an optimum threshold to define sensitivity and specificity of FcMBL ELLecSA in each target population is determined. In addition, the FcMBL ELLecSA for infection diagnosis can be validated, e.g., in high infective risk ICU and trauma patients Determining the binding spectrum of the FcMBL ELLecSA assay for detection of multiple clinically relevant bacterial and fungal strains when spiked into human blood: Microbial strains can be collected from different sources, including ATCC, and the BEI Resources repository.

To minimize epigenetic changes to the bacteria assayed, isolates from human clinical samples are used. For example, a single colony from an 8-24 hr agar plate culture is seeded in cell culture medium (e.g., RPMI 1640) containing a blocking agent (e.g., ~20 mM glucose) and the medium adjusted to 0.5 McFarland (~$10^8$ CFU/ml). The suspension can be assayed directly (for whole bacteria) and/or following mechanical (e.g., by Sonication-Beadmill) and/or antibiotic (e.g., Carbapenem-Aminoglycoside) lysis. Dilutions (e.g., four-fold dilutions) are then prepared for the FcMBL assay in the presence of serum and whole blood using clinically relevant sample sizes (e.g., ~1-5 mL). The table generated can then provide an indication of the in vitro diagnostic spectrum of the assay.

In some embodiments, the lowest amount of LPS that could be detected by ELLecSA was determined to be in the It was determined that the high avidity FcMBL-coated microparticles were not sensitive to matrix effects, and there were consistent reads in buffer, serum, plasma from healthy donors (e.g., FIGS. 15A-15B). However, differences in signal with whole blood samples were observed. Without wishing to be bound by theory, this was, at least in part, due to MBL-specific, low affinity binding to sugar moieties, for example, Lewis antigens on red blood cells (RBCs). In order to reduce or inhibit binding of interfering molecules (e.g., sugar moieties) to microbe-binding molecules described herein, a blocking agent or a competitive inhibitor, e.g., glucose, can be added in a blood sample. For example, glucose can displace the Lewis antigens and prevent microbe-binding molecules binding to RBCs, while microbial carbohydrates, including, e.g., mannan, LPS, can easily displace the glucose bound on the microbe-binding molecules. See, e.g., International Patent Application No. PCT/US14/28683 filed Mar. 14, 2014 entitled "METHODS AND COMPOSITIONS FOR IMPROVING DETECTION AND/OR CAPTURE OF A TARGET ENTITY," the content of which is incorporated herein by reference. This modification can decrease a signal from anti-Lewis antigen ELISA in samples of Lew+ patients in the presence of glucose.

Figure 3C:
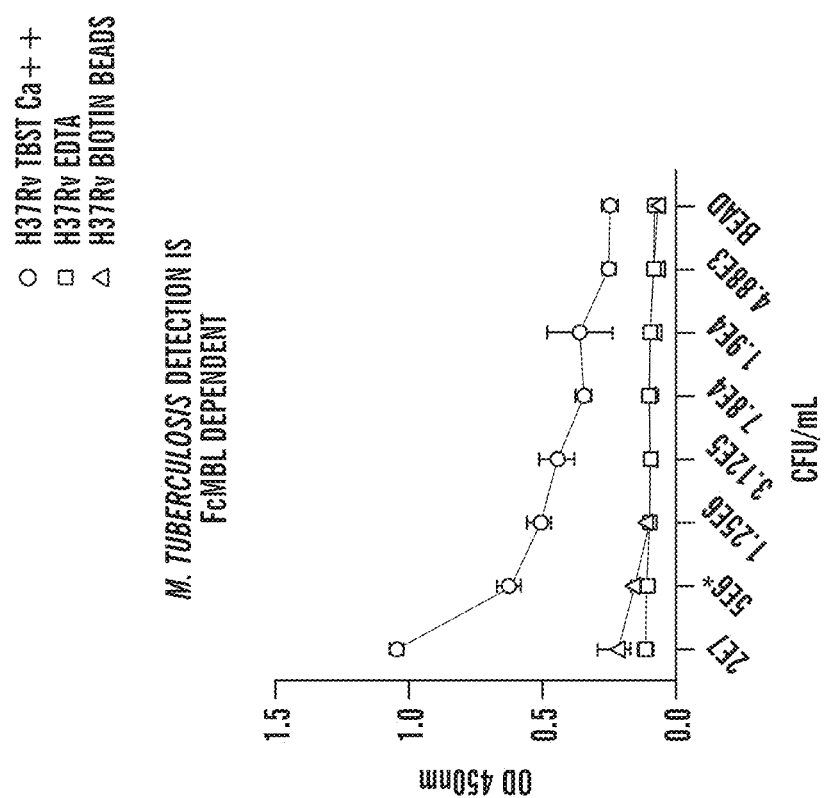

The CRD specific binding of blood cells being reduced or abolished by higher amounts of LPS indicated that the interference of low affinity carbohydrate groups was displaced by the higher affinity LPS. The incubation of the microbe-binding molecules with varying concentrations of glucose was used to determine the optimum concentration sufficient to abolish this interference. In some embodiments, 10 mM glucose can be used to reduce or abolish the interference of low affinity carbohydrate groups. See International Patent Appl. No. PCT/US14/28683 for additional information. PRR-coated (e.g., FcMBL- or CRP-coated) beads can be used in the ELLecSA to detect MAMPs in buffer or whole blood. FIGS. 15A-15B show ELLecSA detection of LPS and mannan in whole EDTA blood and TBST-Ca++. ELLecSA detection of whole pathogens in healthy human blood is inhibited and/or interfered by immune factors and therefore the ELLecSA signals is reduced or quenched as compared to buffer or serum, as seen in FIG. 15C. Even while quenched, the ELLecSA can detect the presence of whole intact pathogenic cells in whole human blood, as seen in FIG. 3C where titers of irradiated strains of *M. tuberculosis* was detected and quantified by the ELLecSA.

Bacterial lysis amplifies the microbe-binding molecules (e.g., FcMBL) ELLecSA signal. For example, beadmill treatment of bacteria showed that mechanical disruption allowed FcMBL to broaden its binding profile. In order to disperse the microbial or bacterial carbohydrates and enhance exposure of CRD-binding motifs, microbes or bacteria can be treated with microbicidal or bactericidal antibiotics. Inventors discovered that, in some embodiments, treating microbes or bacteria for about 1 to 4 hours with a broad spectrum antibiotic (e.g., beta-lactam targeting PBP3), which causes the bacteria to shed large amounts of LPS, transfers the active fraction to the supernatant.

Furthermore, detection of MAMPs by surface tethered PRRs can be increased by the physical disruption of the microbes. The in vivo release of MAMPs in the course of an infection generates a detectable ELLecSA signal in the bloodstream in the absence of circulating live pathogens. Without wishing to be bound by theory, the microbial metabolism and/or the immune response of the host is responsible for the release of MAMPs in the bloodstream from a remote location, thereby causing the symptoms associated with sepsis and the general response to the infection. The exacerbation of clinical signs of infection following the initiation of antimicrobial treatment or the restoration of the immune system in acquired immunodeficiency syndrome is well known, and ELLecSA is capable of detecting such a release of MAMPs following the initiation of antimicrobial therapy. It can be applied in vitro in susceptibility assays as a surrogate for bactericidal activity in microbes releasing MAMPs recognized by the chosen PRR coated surface or in vivo to test the efficacy of antibiotic treatment as a measurement of the systemic effect of the therapy, integrating microbiological susceptibility data and PK/PD parameters for a true assay of overall efficacy and potency of a regimen.

Using the ELLecSA, FcMBL, CRP, or any PRR coated bead can be used as a capture method for MAMPs post lysis of the cell. FIGS. 12A-12B, 18A-18E, and 19A-19D describe the use of antibiotics as a treatment to help shed and expose the MAMPs for PRR binding (e.g., FcMBL or CRP). FIG. 16E describes a time course experiment where a 0.5 McFarland culture of an amp-C mutant *Enterobacter clocae* was exposed to 100 ug/mL cefazolin, ceftazidime and cefepime for 4 hours. The control was a freshly grown 0.5 McFarland culture. The mutant *E. cloacae* was resistant to cefazolin and ceftazidime but susceptible to cefepime. The FcMBL coated beads do not bind *E. cloacae* as a whole bug culture, as seen in FIG. 16E. After being exposed to cefepime for 4 hours at 37 degrees, the susceptible pathogen began to shed MAMPs (which were not shed at the 2 hour incubation mark) which were subsequently bound by the FcMBL beads and detected on the ELLecSA by rhMBL hrp.

Additionally or alternatively, mechanic disruption of the cell wall can yield to the exposure of different MAMPs on the cell wall of pathogen. FIGS. 18A-18B and 21A-21C describe the use of beadmill for MAMP exposure for FcMBL or CRP binding. Table 3 shown earlier provides binding data of pathogens bound by FcMBL or CRP by ELLecSA either as intact whole pathogen, beadmilled, or antibiotic treated. 30 of 32 pathogens tested were bound by either FcMBL or CRP via ELLecSA detection.

To determine the in-vivo relevance of ELLecSA to detect bacterial lysis in vivo, about $10^9$ CFU of *Escherichia coli* was injected in the peritoneal cavity of wistar rats. Four hours after infection, meropenem and cefepime or a sham treatment was administered and a terminal blood draw was performed after another four hours. ELLecSA was performed and a significant increase was observed in the meropenem and cefepime treated group (FIG. 22A).

Generating Receiver Operator Characteristic curves using FcMBL ELLecSA performed on clinical samples drawn from patients from target populations: Existing biomarkers used for the diagnosis of sepsis, such as C-Reactive Protein or Procalcitonin, have limited relevance in trauma patients because physical injury alone can be sufficient to raise their levels in blood. In contrast, the FcMBL ELLecSA assay does not rely on elevated host proteins, and instead directly measures the concentration of blood-borne microbial cell surface materials released from a wide range of different live and dead pathogens. These released microbial materials can accumulate to much higher levels in blood over time, even when the number of live circulating cells remain low (as evidenced by their detection in blood of patients with negative blood cultures), and FcMBL binding to these materials is also not impaired by antibiotic therapy.

To determine the sensitivity and specificity of FcMBL ELLecSA for the diagnosis of severe infections and sepsis, control blood samples from healthy blood donors as well as trauma and surgical patients who are believed to be free of infection (e.g., closed fracture patients and post-operative Altmeyer class I elective surgery patients) are evaluated. Time course samples are drawn to establish intra-individual and inter-individual variation. These results are compared with those obtained with samples from an infected patient population, e.g., including that including ICU patients with sepsis and microbiologically documented infection, and/or trauma or surgical patients with documented sepsis and/or soft tissue, bone or joint infections. FcMBL assays are performed on serial whole blood and plasma samples drawn regularly during antimicrobial therapy (e.g., every other day during the first week of antimicrobial therapy and weekly thereafter). A Receiver Operator Characteristic analysis is performed for each patient subset population and the optimal threshold set accordingly, with definition of sensitivity and specificity in each of the target populations.

Validating the FcMBL ELLecSA for infection diagnosis, e.g., in high infective risk ICU and trauma patients: To validate use of the FcMBL ELLecSA assay for infection diagnosis, a study of critically ill patients admitted to an ICU was undertaken. Patients were excluded from the cohort, for example, if they are undergoing plasmapheresis, have received more than 2 units of blood products during the preceding 6 h, or are enrolled in a clinical trial of an anti-endotoxin therapy.

50+ sepsis patients from the Beth-Israel Deaconess Medical Center emergency department and aged matched non-infected control patients, as well as healthy blood donors and post-operative non-infected SIRS patients, were prospectively enrolled. Serial determination of ELLecSA levels on admission and every 24 hour for 72 hours showed that MBL based ELLecSA allowed the diagnosis of sepsis with a sensitivity of about 76%. Thresholds were established by ROC curve analysis. 74% of clinically determined sepsis patients are ELLecSA positive (only 20% of the patients were blood culture positive). IRB approved blood samples were collected and screened by FcMBL ELLecSA.

Baseline determination of the FcMBL ELLecSA assay is determined upon enrollment in the study and upon discharge from the unit. Daily clinical evaluation for sepsis is performed according to the Centers for Disease Control and Prevention (CDC) criteria (8). Episodes of infection can be diagnosed, e.g., by microbiologic, laboratory, radiologic, and/or operative data, according to local practices. Further determinations of FcMBL-binding material levels are performed using the ELLecSA, e.g., upon modification of the clinical status. Severe sepsis is generally considered to be present when criteria for sepsis syndrome (9, 10) are met. Shock is defined as a mean arterial pressure <60 mm Hg or the use of vasopressor therapy (other than dopamine at a dose of >5 µg/kg). Baseline severity of illness can be quantified using the APACHE II score (11); the degree of baseline organ dysfunction can be quantified using the Multiple Organ Dysfunction (MOD) (12) and/or Sequential Organ Failure Assessment (SOFA) (13) scores. The 2-sample Student's t test or Wilcoxon-Mann-Whitney U test can be used to compare continuous variables. Categorical variables can be evaluated by use of Pearson's $Chi^2$ test, Fisher's exact test, or the Mantel-Haenzel $Chi^2$ test, as appropriate. The association between adverse outcome and FcMBL ELLecSA level can be modeled using logistic regression analysis and be reported as an estimated odds ratio and 95% confidence interval (CI). A multivariate logistic regression model can be used to estimate the association between FcMBL levels and severe sepsis, adjusting for covariates (e.g., age, sex, presence of systemic inflammatory response syndrome [SIRS], and/or APACHE II score).

Example 3. An Exemplary FcMBL ELLecSA Assay on EDTA Clinical Blood Samples

The following are the materials and protocols used to perform a FcMBL assay in accordance with one embodiment described herein. Modifications of the materials and protocols that are within the knowledge of one of skill in the art in light of the disclosure herein and/or immaterial to the inventions are also encompassed by the scope of the inventions described herein. For example, substitution of the following materials with any other functionally equivalent materials and thus modification of the implementation procedure accordingly are encompassed by the scope of the inventions described herein. Concentrations and/or volume of regents added and/or process duration can be varied, for example, depending on the sample volume. As one of skill in the art will appreciate, it is not necessary to perform all the steps in the following order as indicated, for example, some reagents can be added into their respective reservoirs later or earlier than as indicated.

In brief, one embodiment of the FcMBL ELLecSA assay can be described as follows: about 100 µL of sample is added to a desired well of 96-well plate containing FcMBL capture beads, buffer, and FBS. The microbe and/or MAMPs are captured in the presence of the FcMBL capture beads for 20 min by shaking. After capture, the beads are washed using a KingFisher magnetic bead handling automate and captured compounds detected using HRP-labeled MBL (e.g., FcMBL and/or rhMBL). TMB is added for colorimetric quantification and optical density is measured at 450 nm.

In some embodiments, an FcMBL ELLecSA can be performed from blood using ~1 µm super-paramagnetic beads on a magnetic particle processor, e.g., KingFisher™ Flex Magnetic Particle Processor with 96 Deep Well Magnetic Head (Thermo Scientific, Cat #5400620, #5400630) using the following protocol below. Modifications (e.g., addition, deletion, combination, and/or substitution of steps) to the protocol that are within one of skill in the art are also permitted. For example, the protocol can be adapted for use with other microbe-binding molecules than FcMBL. In addition, the order of the steps shown in the protocol below can be changed, e.g., according to a user's preference.

Exemplary Procedures (1) Preparing Mannan Standard Curve solution: Make a serial dilution of a stock solution. The final concentrations of Mannan can be, e.g., as follows: 625 ng/mL, 312.5 ng/mL, 156.2 ng/mL, 78.0 ng/mL, 39.0 ng/mL, 19.5 ng/mL, 9.7 ng/mL and 0 ng/mL Plate Map: "C" stands for mannan controls; while "S" stands for sample

| Row | Mannan Dilutions ng/mL | 1 | 2 | 3 | 4 | 5 | 6 | 7 | 8 | 9 | 10 | 11 | 12 |
|---|---|---|---|---|---|---|---|---|---|---|---|---|---|
| A | 625   | C-1 | C-1 | S-1 | S-1 | S-9  | S-9  | S-17 | S-17 | S-25 | S-25 | S-33 | S-33 |
| B | 312.5 | C-2 | C-2 | S-2 | S-2 | S-10 | S-10 | S-18 | S-18 | S-26 | S-26 | S-34 | S-34 |
| C | 156.2 | C-3 | C-3 | S-3 | S-3 | S-11 | S-11 | S-19 | S-19 | S-27 | S-27 | S-35 | S-35 |
| D | 78.0  | C-4 | C-4 | S-4 | S-4 | S-12 | S-12 | S-20 | S-20 | S-28 | S-28 | S-36 | S-36 |
| E | 39.0  | C-5 | C-5 | S-5 | S-5 | S-13 | S-13 | S-21 | S-21 | S-29 | S-29 | S-37 | S-37 |
| F | 19.5  | C-6 | C-6 | S-6 | S-6 | S-14 | S-14 | S-22 | S-22 | S-30 | S-30 | S-38 | S-38 |
| G | 9.7   | C-7 | C-7 | S-7 | S-7 | S-15 | S-15 | S-23 | S-23 | S-31 | S-31 | S-39 | S-39 |
| H | 00    | C-8 | C-8 | S-8 | S-8 | S-16 | S-16 | S-24 | S-24 | S-32 | S-32 | S-40 | S-40 |

(2) ~20 minute capture procedure:
   Add 500 µL of MyOne AOB-FcMBL conjugated beads to a solution containing 8.5 mL of TBST-5 mM Calcium Chloride and 1 mL of 1M glucose.
   Add 100 µl of the well-mixed bead solution to at least some or all of the wells (mannan control and sample wells—see plate map above)
   Add 800 µl TBST-5 mM Calcium Chloride to first 2 columns (#1 and 2) of capture plate (see plate map).
   Add 650 µl TBST-5 mM Calcium Chloride to the remaining sample columns of capture plate
   Add 50 µl sodium heparin TBST-5 mM into columns of "sample" wells in capture plate.
   Pipette in 1004 of mannan standard to standard wells (see plate map)
   Add 200 µl of blood sample to be tested, in duplicate (or more if desired), to desired wells.
   Shake on bench-top shaker for 20 min at 950 rpm at room temperature.

(3) Running the KingFisher
   After ~20 mM capture completion, the FcMBL conjugated beads are removed from the mannan standard or blood sample.
   The isolated FcMBL conjugated beads are washed at least twice with TBST-5 mM Calcium Chloride.

The washed FcMBL conjugated beads are incubated with 1:5000 dilution of rhMBL-HRP in 3% BSA TBST-5 mM Calcium Chloride After incubation, wash the rhMBL-HRP bound FcMBL conjugated beads at least three times with TBST-5 mM Calcium Chloride to remove excess or unbound rhMBL-HRP Add TMB to the rhMBL-HRP bound FcMBL conjugated beads Wash at least once with TBST-5 mM Calcium Chloride.

Immediately block the TMB colorimetric reaction by adding 50 µL of 1N sulfuric acid to each well of containing rhMBL-HRP bound FcMBL beads and TMB Read the absorbance at 450 nm using spectrophotometer (e.g., Synergy H1 Hybrid Reader) and export the optical density data to a spreadsheet for analysis.

Total Program time is about 52 min.

Example 4. Integration of the ELLecSA Diagnostic and Therapeutic Capabilities into a Blood Cleansing Device The diagnostic capabilities of FcMBL as described herein, e.g., in an ELLecSA-format as described herein, can be adapted for integration into a blood cleansing device, e.g., using FcMBL molecules, to selectively remove pathogens from blood in patients with systemic infections or sepsis. For example, the microfluidic-magnetic blood cleansing device, e.g., as described in International Application No. PCT/US2012/031864 filed Apr. 2, 2012 and PCT/US2011/021718 filed Jan. 19, 2011, can be used, in combination with superparamagnetic nanoparticles coated with a genetically engineered version of the natural blood opsonin, Mannose Binding Lectin (MBL), as a life-saving therapy in a small animal model (Data not shown). The microfluidic units can be scaled up to provide much higher and clinically relevant flow rates (Liters/hr). Disposable magnetic separator cartridges that can efficiently capture >90% of a broad range of pathogens, including Gram positive and Gram negative bacteria and fungi, as well as LPS-endotoxin from flowing blood were developed and described in Pat. App. No. 61/772,360 filed Mar. 4, 2013, the content of which is incorporated herein by reference in its entirety. A continuous mixing system that ensures rapid capture of pathogens while minimizing hemolysis and coagulation was also developed and used to remove bacteria, fungi and endotoxin from whole human blood flowing at >1 L/hr in vitro. See, e.g., U.S. application Ser. No. 13/918,193 filed Jun. 14, 2013 and International Patent App. No. PCT/US2013/050405 filed Jul. 12, 2013, the contents of which are incorporated herein by reference, for examples of the continuous mixing devices and/or systems. Using the microfluidic-magnetic blood cleansing device, in combination with the FcMBL magnetic beads and other modules/devices as described above, a clearance of >90% of S. aureus bacteria and >99% of LPS-endotoxin from blood, a reduction of pathogen and immune cell infiltration in multiple organs, a decrease in systemic inflammatory cytokine levels, and an significant increase in survival rates after 5 hours of continuous blood cleansing were achieved in rats.

By integrating the diagnostic capabilities of FcMBL as described herein, e.g., based on the principle of an sandwich assay such as ELISA, into the blood cleansing device, a single portable unit can be deployed in emergency field and/or hospital environments to rapidly test and treat blood-borne infectious diseases. Without wishing to be limiting, the platform technology described in the context of FcMBL for capture and/or detection of microbes, can be extended to selectively remove any endogenous or exogenous blood-borne components that can threaten human health, including, e.g., pathogens, toxins, inflammatory cytokines, hormones, and potentially cancer cells.

FIG. 22B shows the ELLecSA's ability to detect the presence of MAMPs released from an in vivo study involving the cleansing of blood using an FcMBL coated cleansing device. Cefepime treated rats infected with $10^9$ CFU E. coli were anesthetized and their blood was run through an FcMBL coated cleansing device. MAMPs collected from the FcMBL were analyzed. Time points were collected at 1 hour and 2 hours post FcMBL treatment. Results show a decrease in MAMPs in the blood post FcMBL treatment.

Example 5. Detection of Microbes and Microbial MAMPs/Products

Some embodiments of various aspects directed to culture-free diagnostic of infection as described herein are based on the ability of the FcMBL molecules and other lectins to capture not only intact microbes but also released MAMPs (e.g., LPS) with greater sensitivity, that are associated with infection and sepsis from biological matrices such as blood. The detection of bacteria or their released MAMPs using FcMBL molecules and other lectins, including rhMBL and CRP, can be used to test clinical samples, blood products or complex pharmacological matrices, and/or used in the food industry (e.g., rapid detection of bacteria or endotoxin or fungi in food products).

The diagnostic assay described herein generally relies on the capture of microbes and/or MAMPs from a sample using lectin molecules (e.g., FcMBL molecules, other Fc-lectin molecules, rhMBL, CRP, CRP-Fc, and other lectins), and detection of the materials captured from the sample. In some embodiments, the capture of intact microbes can employ smaller 128 nm FcMBL beads for higher efficiency. In some embodiments, the capture of MAMPs can employ larger 1 micron FcMBL beads for higher efficiency (FIGS. 5A-5B). Comparison of two FcMBL bead sizes (e.g., ~1 uM and ~128 nm in size) has shown that in some embodiments, the ~1 uM FcMBL beads preferentially capture bacterial MAMPs (e.g., LPS) and can be better suited, e.g., for use in the detection assay, whereas the ~128 nm beads can be better suited for capture of intact bacteria, e.g., for antibiotic susceptibility (FIGS. 5A-5B). Beads of other sizes and/or alternative chemistry can also be used, e.g., depending on the types of microbes to be captured. Without wishing to be limited, any lectin described in the International Patent App. No. PCT/US2012/047201 filed Jul. 18, 2012 can be used to form an Fc fusion protein, which can be used in an FcMBL diagnostic assay described herein but with FcMBL replaced.

An exemplary process for capture of microbes and/or MAMPs (e.g., bacteria/bacterial components) from a sample, e.g., blood of patients suspected of infection, is as follows. The sample or "suspension" to be tested (e.g., but not limited to anticoagulated blood) is diluted with a buffer containing $Ca^{2+}$ (e.g., in a dilution of about 1:5 with TBST 5 mM Ca++ buffer), optionally supplemented with a blocking agent, which can be added to enhance specificity and/or sensitivity of microbial capture (e.g., a 6-carbon oside such as glucose or mannose) as described in PCT Application Serial No. PCT/US14/28683 filed Mar. 13, 2014, and in the case of blood, plasma or serum heparin (e.g., ~4 mg/ml). FcMBL-coated substrates (e.g., FcMBL-coated superparamagnetic beads) are added and microbial capture is carried out, e.g., for about 20 minutes (with agitation at ~900 rpm on an orbital shaker). The FcMBL-coated substrates are then separated accordingly from the sample. For example, magnetic separation is used to separate FcMBL-coated magnetic beads from the sample. The separated FcMBL-coated substrates (e.g., FcMBL-coated magnetic beads) are then washed (e.g., at least once, at least twice or more) in TBST 5 mM Ca++ and assayed using one or any combinations of the following developed assays for microbe detection and identification.

FcMBL-HRP sandwich ELLecSA. The sandwich FcMBL-HRP ELLecSA (also known as an Enzyme Linked Lectin Sorbant Assay (ELLecSA)) can be used for generalized detection of microbes and/or microbial components, e.g., in clinical blood samples and other complex media (such as food sample and pharmacological products). The sandwich ELISA and modifications thereof is described in International Patent Application No. PCT/US2012/047201 filed Jul. 18, 2012, and PCT Application Serial No. PCT/US14/28683 filed Mar. 13, 2014, the contents of which are incorporated herein by reference in their entireties.

In some embodiments, the sandwich FcMBL-HRP ELLecSA can employ FcMBL beads, e.g., FcMBL magnetic beads, for microbe and/or MAMP capture, and FcMBL-HRP for detection.

In other embodiments, the sandwich FcMBL-HRP ELLecSA can employ FcMBL beads, e.g., FcMBL magnetic beads, for microbe/microbial fragment capture, and rhMBL-HRP for detection. FIG. 6 shows that FcMBL Bead capture—rhMBL-HRP detection can increase sensitivity of the FcMBL ELLecSA. Detection sensitivity of mannan captured from both buffer and whole blood by FcMBL superparamagnetic beads can be further reduced to below 1 ng/ml mannan by using the detection reagent recombinant MBL labeled with HRP (horse radish peroxidase) leveraging the increased avidity of the multimerized MBL (FIG. 6).

Dual Lectin sandwich ELLecSA. This sandwich ELLecSA can employ any Fc-lectin fusion protein instead of FcMBL. For example, any lectin expressed as an AKT-Fc-Lectin format (as described in International Patent Application No. PCT/US2012/047201 filed Jul. 18, 2012) can be bound to the capture bead. The same or different lectin can be used to detect the microbes and/or MAMPs or products captured by the first lectin-coated capture beads.

Example 6. Detection/Identification of *Mycobacterium tuberculosis* (MTB)

MTB infects approximately 30% of the world's population and kills in excess of about 1.5 million people annually. MBL capture beads can be used to capture both components of the MTB cell wall (e.g., cell wall antigens) as well as intact *M. tuberculosis* (in a calcium dependent manner) thereby creating a rapid <1 hour diagnostic of MTB. For example, *M. tuberculosis* mannosylated cell wall antigens (e.g., Phosphatidylinositol Mannosides (PIM 1,2 and PIM 6) & mannose-capped LipoArabinoMannan (LAM) and/or the irradiated MTB isolates H37Rv and HN878 can be captured by FcMBL superparamagnetic beads from a buffer, serum and/or whole blood containing about 5 mM $Ca^{2+}$, and detected by rhMBL-HRP (FIGS. 3A-3D) in a similar manner as described in Example 3 or 5.

Positive MBL ELLecSA in the context of negative cultures can indicate the possibility of *M. tuberculosis* infection. The capture of *M. tuberculosis* from complex matrices such as sputum using FcMBL magnetic beads can make it possible to perform downstream identification with greater sensitivity, e.g., by auramine direct examination, PCR, mass spectroscopy, sequencing, immunoassay, and any combinations thereof.

Example 7. Detection/Identification of Lipopolysaccharide (LPS)

FcMBL beads can capture LPS (a major component of the Gram-negative cell wall) in any sample, e.g., simple (buffer) and complex (blood, serum) matrices, with a sensitivity reaching at least about 60 ng/ml or higher (in blood) as detected by FcMBL ELLecSA (as described in Example 3 or 5) using about 5 µl of FcMBL beads with a ~1 ml testing volume. The capture and detection of LPS by FcMBL is calcium specific as demonstrated by LPS binding and detection loss in the presence of chelators (e.g., EDTA as shown in FIG. 7). The LPS captured by the FcMBL beads can be measured or detected using various assays, including but not limited to, FcMBL ELLecSA (FIG. 8A), anti-LPS ELISA such as anti-Lipid A ELISA (FIG. 8B), immunofluorescence, and limulus amebocyte lysate (LAL) assay (FDA approved measure of LPS) (FIG. 9A).

The detection range of LPS using FcMBL beads can cover at least 3 logs or more, for example, going from about 16,000 ng/ml to about 15 ng/ml in buffer whereas state of the art Endosafe™ LAL detection from Charles River Laboratories® have a 2 Log range. In addition, the Endosafe™ LAL detection product requires dilution of any complex matrices or detergent and performs poorly in blood products due to interference with coagulation cascade factors.

Example 8. Detection of Whole Bacteria by Physical and/or Chemical and/or Biological Release of Compounds Detectable by PRRs (MAMPs)

Bacteria that escape the detection of lectin-bound compounds, for example, by production of a masking capsule and/or modification of the exposed terminal sugars, can be made detectable by disruption of their architectural integrity by physical means (e.g., but not limited to, sonication, bead milling, centrifugation, and/or flash-freezing) or chemical means (e.g., but not limited to, addition of an antimicrobial molecule/substance and/or cell lysis agents. For example, *Klebsiella oxytoca* isolates not detected by the FcMBL Sandwich ELLecSA can be rendered detectable by exposure to ultrasonic disruption (FIG. 10). Other examples of enhanced detection of bacteria by mechanical disruption followed by ELLecSA are shown in FIG. 11, FIGS. 18A-18B, and FIGS. 19A-19C, and FIG. 20.

In some embodiments, the addition of bactericidal antibiotics (e.g., but not limited to, beta-lactams, aminoglycosides) can enhance the ELLecSA signal to an even greater extent than mechanical disruption. FIGS. 12A-12B, FIGS. 16A-16E, and FIGS. 17A-17D show that efficacy of antibiotic treatment can be tracked by ELLecSA detection of MAMPs of *E. cloacae* and other bacteria species. Accordingly, the ELLecSA diagnostic can allow the detection of circulating pathogen compounds in complex matrices such as blood and can be used to monitor the in vivo clinical efficacy of antibiotic regimens by quantifying the release of bacterial antigens.

Example 9. Use of a Combination of FcMBL ELLecSA and Anti-LPA ELISA Assays to Distinguish Between Gram-Negative Bacterial Infection and Other Etiologic Agents in Clinical Samples As shown earlier, FcMBL beads can capture and detect pathogens (including *E. coli* and *M. tuberculosis*) as well as microbial carbohydrates including LPS (as low as 15 ng/ml as limit of detection) and *M. tuberculosis* cell wall antigens (as low as 1 ng/ml mannan as limit of detection) from complex biological fluids. In addition, pathogen-derived carbohydrates can be detected in blood samples from animal models of infection.

Infection can be diagnosed or identified by a positive readout from FcMBL ELLecSA following capture of microbes with FcMBL molecules. Etiology can be narrowed down by a follow-on anti-LPS immunoassay or ELISA assay. For example, the infection-positive (and optionally infection-negative) samples (determined based on readouts from FcMBL ELLecSA) can be further subjected to an anti-LPS ELISA or immunofluorescence. A positive readout from the anti-LPS ELISA can indicate possible gram-negative infection. If negative readout is obtained from the anti-LPS ELISA, the infection with be caused by non-Gram negative agents.

A case study was performed to illustrate this aspect. There were three patients: Patient A had an unknown condition; Patient B was suspected of having sepsis (e.g., caused by Respiratory Gram-negative rods); and Patient C was suspected of having sepsis after gut surgery. Their blood samples were assayed by a combination of FcMBL ELLecSA and anti-LPS ELISA to identify infection positive (FcMBL ELLecSA) clinical samples and those with possible gram-negative infection (anti-LPS ELISA).

Patient A shows negative readouts in both FcMBL ELLecSA and anti-LPS immunofluorescence, indicating that Patient A had no sepsis. Both Patient B and Patient C are positive for infection as evidenced by a positive readout from the FcMBL ELLecSA. However, only the sample of Patient B, not Patient C, showed a positive LPS staining from anti-LPS immunofluorescence, which indicates that Patient B was suffered from enterobacterial or pseudomonal sepsis, while Patient C was suffered from sepsis of other etiology.

Accordingly, use of FcMBL ELLecSA in combination with a specific secondary reagent (e.g., an anti-LPS assay) can allow for distinction between MBL bound Gram-negative LPS infection from other etiologic agents (e.g., non-Enterobacterial or Pseudomonal pathogens). The FcMBL diagnostic can not only allow the detection of circulating microbial compounds in complex matrices such as blood and be used for rapid detection of unknown biothreats such as pandemic flu or biowarfare agents, but can also allow distinction between classes of pathogens by subsequent characterization of the captured materials, e.g., using one or more reagents specific for each class of pathogens.

Example 10. FcMBL ELLecSA Monitoring of Antimicrobial Activity in Patients

Inventors have shown in vitro that lysis of bacteria by mechanical disruption (e.g., Beadmill, Sonication) of bacteria enhances the detection of bacteria by the FcMBL ELLecSA. Inventors have also discovered that the addition of bactericidal antibiotics (beta-lactams, aminoglycosides) and incubation for 30 minutes to 24 hours, depending on the pathogen and the antibiotic, at 37° C. can enhance the FcMBL ELLecSA signal even more.

The in vivo application of this observation allows the use of FcMBL ELLecSA to monitor the clinical efficacy of an antimicrobial regimen by measuring the destruction of pathogens, a parameter that has eluded physicians since the first use of antimicrobial agents The serial determinations of FcMBL therapy provide a novel tool to establish the biological efficacy of an antimicrobial regimen in patients by measuring the release of microbial carbohydrates upon active therapy. Patients with an infection diagnosed without antibacterial susceptibility documentation (serological diagnosis, PCR diagnosis, previous antibiotic treatment) are numerous and the confirmation of the therapeutic activity of the probabilistic regimen is difficult to obtain. The following exemplary strategy can provide previously unavailable data to ascertain the clinical activity of the antibiotic:

A baseline FcMBL ELLecSA level is determined from a blood sample

The antibiotic treatment is initiated

Serial FcMBL ELLecSA levels are determined in a time course that is guided by the pharmacokinetic-pharmacodynamic properties of the patient/antibiotic combination Treatment related spikes in FcMBL levels are diagnostic of adapted treatment.

It has been the clinical practice to document some infections by a "therapeutic trial": when suspecting an infection without microbiological documentation, Physicians have been testing the hypothesis of the bacterial etiology of a clinical disorder by providing antibiotics and monitoring the clinical improvement of the patient under the treatment. A clinical improvement equated a diagnosis of infection. In the absence of improvement over the duration of the "trial", the treatment was changed to encompass different pathogens or the infectious etiology was ruled out. The FcMBL ELLecSA can be applied to providing objective metrics for "trial" success or failure. In one embodiment the method can comprise:

A baseline FcMBL ELLecSA level is determined from a blood sample

The antibiotic treatment is initiated

Serial FcMBL ELLecSA levels are determined in a time course that is guided by the pharmacokinetic-pharmacodynamic properties of the patient/antibiotic combination Treatment related spikes in FcMBL levels are diagnostic of an infection within a susceptible organism The early detection of the antibiotic regimen activity allows a faster evaluation of the trial success and faster explorations of microbial etiologies: bacterial, fungal, mycobacterial.

The use of serial determinations of FcMBL ELLecSA allows adapting an antimicrobial regimen in the absence of antimicrobial susceptibility testing. Following the successful trial of a broad spectrum agent, iterations with narrow spectrum agents allows optimizing the treatment of the unknown agent. In one embodiments, the method can comprise:

A baseline FcMBL ELLecSA level is determined from a blood sample

The broad spectrum antibiotic treatment is initiated

Serial FcMBL ELLecSA levels are determined, efficacy proven

A narrow spectrum agent is used: if there is no FcMBL spike, the treatment is ineffective.

A different narrow spectrum agent is then administered. The appearance of the spike confirms treatment efficacy Serial determinations of FcMBL ELLecSA allows to optimize an antimicrobial regimen. In many cases, the clinical improvement following the implementation of an antimicrobial regimen does not meet expectations. There are currently no methods other than measuring serum level adequacy to document the treatment. This procedure in no way reflects the true activity of the agent at the site of infection. The use of FcMBL serial determinations allows the determination of true efficacy, and allows the evaluation of combination therapy, posology or administrations schemes.

Example 11. Additional Exemplary Methods to Detect and/or Quantify MAMPs Bound to Microbe-Binding Molecules Described Herein (e.g., FcMBL)

In addition to HRP labeled reagents, detection of PPRs after capture of MAMPs with microbe-binding molecules can include but is not limited to fluorescent labeling reagents such as FluoSpheres® (Life Technologies) and DyLight Fluor labeling reagents (Thermo Fisher).

In some embodiments, microbial materials or MAMPs bound to microbe-binding molecules described herein can be detected by antibodies that bind to MAMPs. For example, antibodies can include, but are not limited to, anti-LPS antibodies, and anti-Staph antibodies. In some embodiments, the antibodies can be labeled with a detectable label such as HRP labeling reagents and/or fluorescent labeling reagents.

In some embodiments, detection of PRRs after capture of microbial materials or MAMPs can be performed by non-labeling methods. For example, in some embodiments, microbial materials (e.g., MAMPs) can be detected by polymerase chain reaction (PCR) or quantitative PCR (qPCR). Once microbes and/or MAMPs have been captured on PRR-coated beads, the PRR-coated beads with bound microbes and/or MAMPs can be removed from the sample matrix that can contain both inhibitory molecules that prevent effective gene amplification and excess host DNA that can compete with the primers used for specific microbial targets. The sensitivity of PCR and its specificity can be increased by the removal of unwanted host DNA that could generate a false positive signal.

Primers for gene amplification can either be specific for a given genus, species or clone of microorganism or generic of prokaryote, archeal or eukaryote phylum. Sequencing of an amplification fragment can allow the identification of the microbes in the sample using a database query system.

Alternatively or additionally, the DNA materials bound to the PRR-coated beads can be detected by high throughput sequencing or direct sequencing. Thus, identification, typing and/or detection of resistance determinants in a microorganism can be determined.

In some embodiments, microbes and/or MAMPs captured on PRR-coated beads can be detected and quantified by a mass spectrometric method. Exemplary mass spectrometric methods include, but are not limited to time of flight (TOF), quadrupole, triple quadrupole, high resolution and other mass spectrometric methods. Additionally, exemplary ionization methods, prior to mass spectrometric analysis, include but are not limited to matrix assisted laser desorption ionization (MALDI), liquid chromatography (LC), gas chromatography (GC), and electro-spray ionization (ESI).

The chemical or physical analysis of the microbial material bound to the PRR-coated bead by mass spectrometry or spectroscopy (e.g., raman or otherwise) can allow detection, quantification and/or identification of the bound material. In one embodiment, analysis of the eluate from the FcMBL-coated beads has shown different MALDI-TOF MS profile depending on the types of microbes captured on the FcMBL-coated beads (FIG. 14). Analysis of the area under the MS profile curve can allow quantification of the microbial matter or MAMPs captured on the PRR-coated beads.

The analysis of the material eluted from the PRR-coated beads (e.g., FcMBL-coated beads) can be identified to either a molecular level or a general pattern, which can be subsequently matched to a known database of profiles derived from previous isolates or patient samples. The construction of a profile database and the algorithms used to match a sample to a microbe or group of microbes can rely on scores determined according to the presence or absence of known or unknown characteristics of individual microbes or microbe classes.

Alternatively or additionally, the kinetics of binding of MAMPs to the PRR-coated beads can be detected in real time using surface plasmon resonance or similar detection technologies.

In some embodiments, PRR-coated beads with bound microbes and/or MAMPs can be detected by determining the number of immune cells that phagocytize the PRR-coated beads with bound microbes and/or MAMPs. The inventors found that micrometer sized streptavidin coated beads were phagocytized by the THP-1 human monocyte cell line. The inventors also found that micrometer sized streptavidin coated beads conjugated to FcMBL-biotin were mostly not phagocytized by THP-1 cells. However, micrometer sized streptavidin coated beads conjugated to FcMBL-biotin incubated with MAMPs were phagocytized.

Accordingly, upon phagocytosis the THP-1 cells are laden with PRR-coated beads bound with microbes and/or MAMPs. In some embodiments, the PRR-coated beads can be superparamagnetic PRR-coated beads. In these embodiments, either the non-magnetic cells without phagocytosis activity or the cells that are susceptible to magnetic capture due to the phagocytosis of MAMP coated PRR tethered superparamagnetic microparticles, can be detected. The number or percentage of THP-1 cells associated to PRR microparticles can be a metric of the amount of MAMPs bound PRR-coated beads and therefore a quantitative or semi-quantitative measure of the amount of MAMP in the sample.

In some embodiments, the PRR-coated beads can be fluorescently labeled and the number or percentage of THP-1 cells associated to fluorescently labeled PRR tethered beads can be a metric of the amount of MAMPs bound PRR-coated beads.

An exemplary protocol for phagocytosis assay is described below. A liquid nitrogen ampule of $2\times10^6$ THP-1 human monocytic cell line was thawed and expanded in DMEM with 10% decomplemented FBS. In FIG. 24, AOB-FcMBL coated streptavidin myOne beads labeled with Cy3-biotin were incubated in 50% E. coli culture medium/50% TBST-Ca++ (E. coli beads) or TBST-Ca++ (control beads) for 30 minutes on a Hula shaker and the beads were subsequently washed three times in TBST-Ca++. Both sets of beads were then incubated with $10^6$ THP-1 cells in DMEM-10% FBS in an eppendorf tube for 60 minutes at 37° C. with a bead to THP-1 cell ratio of 10/1 and 100/1 (i.e. $10^7$ beads for $10^6$ THP-1 and $10^8$ beads for $10^6$ THP-1, respectively). The beads-challenged THP-1 cultures were then either studied directly or submitted to magnetic separation on a magnetic rack. The magnetically separated material was washed with TBST-Ca++ and then resuspended in the initial volume. The cells remaining in the non-magnetically bound suspension were also saved for analysis. The beads/cells were gently pelleted and resuspended in PBS-4% paraformaldehyde for fixation and delayed analysis. Cells were then imaged on a confocal microscope or analyzed using a flow cytometer, counting the cells (identified by FSC/SSC) that had phagocytized beads (Cy3+) or had not phagocytized the beads (Cy3−). Overall the results showed that bead uptake by THP-1 monocytic cells was greater (e.g., 10-20 times greater) for beads exposed to bacterial culture medium than for control beads. This can be measured by the determination of the fluorescent labeled (bead-associated) THP-1 to non labeled THP-1 or to the number of THP-1 remaining after magnetic separation that specifically remove THP-1 cells laden with superparamagnetic beads. The cellular activation of the macrophages can be further studied by fluorescent staining of membrane clusters of differentiation (CD) markers, or of intracellular markers in the case of a flow cytometry analysis, or by studying the transcriptomic response to the beads, which can be used to discriminate between bacterial types according to the qualitative nature of the response.

Example 12. Antibiotic Development Screening Assays

In one aspect, a PRR/MAMP assay (or a PRR base assay) can be applied to screen candidate molecules or compositions for antibiotic or antimicrobial properties. For example, in some embodiments, samples comprising microbes can be contacted or incubated with one or a panel of different candidate molecules, e.g., at various concentrations and/or for varying amounts of time. After incubation, the MAMP level released and/or exposed by the candidate molecule(s) in each sample can be measured and compared to a baseline level. The baseline level can correspond to the MAMP level present in the sample(s) prior to the incubation with the candidate molecule(s). Candidate molecule(s) that induce a change in MAMP level relative to the baseline level can indicate possible antibiotic or antimicrobial properties. In some embodiments, candidate molecule(s) that induce an increase in MAMP level, by at least about 50%, at least about 60%, at least about 70%, at least about 80%, at least about 90%, at least about 95%, or more, relative to the baseline level can indicate possible antibiotic or antimicrobial properties. In some embodiments, candidate molecule(s) that induce an increase in MAMP level, by at least about 1.1-fold, at least about about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 3-fold, at least about 4-fold, at least about 5-fold, or more, relative to the baseline level can indicate possible antibiotic or antimicrobial properties. In some embodiments, candidate molecule(s) that induce a decrease in MAMP level by at least about 10%, at least about 20%, at least about 30%, at least about 40%, at least about 50%, at least about 60%, at least about 70%, at least about 80%, at least about 90%, at least about 95%, at least about 97% or more, relative to the baseline level can indicate possible antibiotic or antimicrobial properties. In some embodiments, candidate molecule(s) having possible antibiotic or antimicrobial properties can decrease the MAMP detectable signal level to a non-detectable level. Further screen of probable candidate antibiotics against individual microbes can be performed to identify specific microbial targets for candidate molecule(s), e.g., by contacting different species or genus of microbes individually with candidate molecule(s).

In another aspect, a PRR/MAMP assay (e.g., a PRR based assay) can be applied to identify an effective or the most effective antimicrobial (e.g., antibacterial) candidate molecule or a combination or panel of candidate molecule(s) against a specific microbe species or genus, including against newly identified or newly resistant microbes. For example, in some embodiments, a sample comprising microbes to be assayed or targeted (e.g., a specific microbe species or genus) can be contacted or incubated with one or a panel or combination of different candidate molecules, e.g., at various concentrations and/or for varying amounts of time. After incubation, the MAMP level released and/or exposed by the candidate molecule(s) in each sample can be measured and compared to a baseline level. The baseline level can correspond to the MAMP level present in the sample(s) prior to the incubation with the candidate molecule(s). Candidate molecule(s) that induce a change in MAMP level relative to the baseline level, and/or induce the most significant change in MAMP level, when compared to changes in MAMP levels induced by other candidate molecule(s) can indicate possible therapeutic regimes against the specific microbe species or genus. In some embodiments, candidate molecule(s) that induce an increase in MAMP level, by at least about 50%, at least about 60%, at least about 70%, at least about 80%, at least about 90%, at least about 95%, or more, relative to the baseline level can indicate possible therapeutic regimes against the specific microbe species or genus. In some embodiments, candidate molecule(s) that induce an increase in MAMP level by at least about 1.1-fold, at least about about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 3-fold, at least about 4-fold, at least about 5-fold, or more, relative to the baseline level can indicate possible therapeutic regimes against the specific microbe species or genus. In some embodiments, candidate molecule(s) that induce a decrease in MAMP level by at least about 10%, at least about 20%, at least about 30%, at least about 40%, at least about 50%, at least about 60%, at least about 70%, at least about 80%, at least about 90%, at least about 95%, at least about 97% or more, relative to the baseline level can indicate possible therapeutic regimes against the specific microbe species or genus. In some embodiments, candidate molecule(s) having possible therapeutic regimes against the specific microbe species or genus can decrease the MAMP detectable signal level to a non-detectable level.

In both aspects described in this Example, the PRR based assays can be conducted either in vitro (e.g., in a cell culture) or in vivo (e.g., in an animal model of an infection to be treated).

REFERENCES

1. J. Garnacho-Montero et al., Timing of adequate antibiotic therapy is a greater determinant of outcome than are TNF and IL-10 polymorphisms in patients with sepsis. *Critical care* 10, R111 (2006).
2. P. R. Murray, H. Masur, Current approaches to the diagnosis of bacterial and fungal bloodstream infections in the intensive care unit. *Critical care medicine* 40, 3277 (December, 2012).
3. S. Sheriff, C. Y. Chang, R. A. Ezekowitz, Human mannose-binding protein carbohydrate recognition domain trimerizes through a triple alpha-helical coiled-coil. *Nature structural biology* 1, 789 (November, 1994).
4. R. Malhotra, J. Lu, U. Holmskov, R. B. Sim, Collectins, collectin receptors and the lectin pathway of complement activation. *Clinical and experimental immunology* 97 Suppl 2, 4 (August, 1994).

5. K. Takahashi et al., Mannose-binding lectin and its associated proteases (MASPs) mediate coagulation and its deficiency is a risk factor in developing complications from infection, including disseminated intravascular coagulation. *Immunobiology* 216, 96 (January-February, 2011).
6. Joo H. Kang, Michael Super, Ryan M. Cooper, Karel Domansky, Amanda Graveline, Tadanori Mammoto, Julia B. Berthet, Heather Tobin, Mark Cartwright, Alex Watters, Martin Rottman, Anna Waterhouse, Akiko Mammoto, Nazita Gamini, Amanda Jiang, Thomas M. Valentin, Alex Diaz, Chong Wing Yung, and Donald E. Ingber. An Extracorporeal Blood Cleansing Device for Sepsis Therapy. (in preparation).
7. W. M. Weinstein, A. B. Onderdonk, J. G. Bartlett, T. J. Louie, S. L. Gorbach, Antimicrobial therapy of experimental intraabdominal sepsis. *The Journal of infectious diseases* 132, 282 (September, 1975).
8. Garner J S, Jarvis W R, Emori T G, Horan T C, Hughes J M. CDC definitions for nosocomial infections, 1988. Am J Infect Control 1988; 16:128-40.
9. Sands K E, Bates D W, Lanken P N, et al. Epidemiology of sepsis syndrome in 8 academic medical centers. JAMA 1997; 278:234-40,
10. Bone R C, Fisher C J, Clemmer T P et al. Sepsis syndrome: a valid clinical entity. Crit Care Med 1989; 17:389-93
11. Knaus W A, Draper E A, Wagner D P, Zimmerman J E. APACHE II: a severity of disease classification system. Crit Care Med 1985; 13:818-29.
12. Marshall J C, Cook D J, Christou N V, Bernard G R, Sprung C L, Sibbald W J. Multiple organ dysfunction score: a reliable descriptor of a complex clinical outcome. Crit Care Med 1995; 23:1638-52.
13. Vincent J L, Moreno R, Takala J, et al. The sepsis-related organ failure assessment (SOFA) score to describe organ dysfunction/failure. Intensive Care Med 1996; 22:707-10.

To the extent not already indicated, it will be understood by those of ordinary skill in the art that any one of the various embodiments herein described and illustrated can be further modified to incorporate features shown in any of the other embodiments disclosed herein. Thus, other embodiments are within the scope and spirit of the invention. Further, while the description above refers to the invention, the description may include more than one invention.

All patents and other publications identified herein are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed herein is:

1. A method of enhancing microbe detection in a sample by a pattern recognition receptor (PRR)-based assay, the method comprising pre-treating the sample to lyse or kill at least one microbe before assaying with the PRR-based assay to detect the at least one microbe or a microbe-associated molecular pattern (MAMP) thereof, wherein the PRR-based assay comprises detection of the MAMPs using a PRR molecule that is tagged with a detectable label.

2. The method of claim 1, wherein said pre-treatment is physical, mechanical, chemical, biological, or any combinations thereof.

3. The method of claim 1, wherein said pre-treatment comprises incubating the sample with an antimicrobial agent.

4. The method of claim 3, wherein the antimicrobial agent can be selected from aminoglycosides, ansamycins, beta-lactams, bis-biguanides, carbacephems, carbapenems, cationic polypeptides, cephalosporins, fluoroquinolones, glycopeptides, iron-sequestering glycoproteins, linosamides, lipopeptides, macrolides, monobactams, nitrofurans, oxazolidinones, oxazolidinones, penicillins, polypeptides, quaternary ammonium compounds, quinolones, silver compounds, sulfonamides, tetracyclines, and any combinations thereof.

5. The method of claim 1, wherein said pre-treatment comprises sonication; agitation; vortexing; milling including beadmilling, grinding, french press, cryofracture; and any combinations thereof.

6. The method of claim 1, wherein said pre-treatment comprises pre-treatment with lysozyme or lysostaphin.

7. The method of claim 1, wherein said pre-treatment disrupts the architectural integrity of the at least one microbe.

8. The method of claim 1, wherein said pre-treatment exposes microbe-associated molecular patterns (MAMPs).

9. The method of claim 1, wherein said pre-treatment increases the sensitivity of the PRR-based assay.

10. The method of claim 1, wherein said pre-treatment increases the spectrum of microbes that are detected by the PRR-based assay.

11. The method of claim 1, wherein said at least one microbe has a masking capsule.

12. The method of claim 1, wherein said at least one microbe is non-capsulated.

13. The method of claim 1, wherein said at least one microbe is selected from the genus of *Acineobacter, Aeromonas, Burkholderia, Candida, Citrobacter, Enterobacter, Enterococcus, Escherichia, Klebsiella, Morganella, Mycobacterium, Proteus, Providencia, Pseudomonas, Salmonella, Serratia, Shigella, Staphylococcus, Stenotrophomonas, Streptococcus, Yersinia*, or any combinations thereof.

14. The method of claim 1, wherein said at least one microbe is resistant to at least one antimicrobial agent.

15. The method of claim 1, wherein the PRR-based assay comprises binding of the MAMPs to a PRR-tethered surface or a PRR-coated solid substrate surface.

16. The method of claim 15, wherein the surface or solid substrate surface is a surface of a bead; a particle; a microparticle; a nanoparticle; a hollow fiber; a fiber; a porous solid substrate; a filter; a screen; a mesh; a tube; a scaffold; a plate; a channel; a gold particle; a magnetic material; a medical apparatus; a needle; a catheter; an implant; a dipstick; a test strip; a filtration device; a membrane; a hollow fiber cartridge; a microfluidic device; a mixing element; a spiral mixer; an extracorporeal device; or any combinations thereof.

17. The method of claim 15, wherein the PRR-based assay comprises detection of the MAMPs using a PRR molecule and the PRR molecule is the same molecule as tethered to the surface or coated onto the solid substrate surface.

18. The method of claim 15, wherein the PRR-based assay comprises detection of the MAMPs using a PRR molecule and the PRR molecule is different from the PRR molecule tethered to the surface or coated onto the solid substrate surface.

19. The method of claim 1, wherein the PRR-based assay is Fc-mannose-binding lectin (FcMBL) based microbe capture and detection assay.

\* \* \* \* \*